US012807932B2

(12) United States Patent
Brouns et al.

(10) Patent No.: US 12,807,932 B2
(45) **Date of Patent: *Nov. 24, 2026**

(54) MODIFIED CASCADE RIBONUCLEOPROTEINS AND USES THEREOF

(71) Applicant: Caribou Biosciences, Inc., Berkeley, CA (US)

(72) Inventors: Stan Johan Jozef Brouns, Wageningen (NL); John van der Oost, Renkum (NL)

(73) Assignee: Caribou Biosciences, Inc., Berkeley, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 18/422,843

(22) Filed: Jan. 25, 2024

(65) Prior Publication Data

US 2024/0174998 A1 May 30, 2024

Related U.S. Application Data

(63) Continuation of application No. 17/179,215, filed on Feb. 18, 2021, now Pat. No. 11,939,604, which is a (Continued)

(51) Int. Cl.

| | |
|---|---|
| ***C12N 9/22*** | (2006.01) |
| ***A61K 38/00*** | (2006.01) |
| ***A61K 48/00*** | (2006.01) |
| ***C07K 14/245*** | (2006.01) |
| ***C07K 14/47*** | (2006.01) |
| ***C12N 9/16*** | (2006.01) |
| ***C12N 15/62*** | (2006.01) |
| ***C12N 15/66*** | (2006.01) |
| ***C12N 15/70*** | (2006.01) |
| ***C12N 15/74*** | (2006.01) |

(Continued)

(52) U.S. Cl.

CPC .............. *C12N 9/22* (2013.01); *A61K 48/005* (2013.01); *C07K 14/245* (2013.01); *C07K 14/47* (2013.01); *C12N 9/16* (2013.01); *C12N 15/62* (2013.01); *C12N 15/66* (2013.01); *C12N 15/70* (2013.01); *C12N 15/74* (2013.01); *C12N 15/81* (2013.01); *C12N 15/82* (2013.01); *C12N 15/86* (2013.01); *C12N 15/902* (2013.01); *C12N 15/907* (2013.01); *A61K 38/00* (2013.01); *C07K 2319/09* (2013.01); *C07K 2319/22* (2013.01); *C07K 2319/60* (2013.01); *C07K 2319/71* (2013.01); *C07K 2319/80* (2013.01); *C07K 2319/85* (2013.01); *C12N 2310/20* (2017.05); *C12Y 301/21004* (2013.01)

(58) Field of Classification Search

CPC . C12N 9/22; C12N 9/16; C12N 15/62; C12N 15/66; C12N 15/70; C12N 15/74; C12N 15/81; C12N 15/82; C12N 15/86; C12N 15/902; C12N 15/907; C12N 2310/20; A61K 48/005; A61K 38/00; C07K 14/245; C07K 14/47; C07K 2319/09; C07K 2319/22; C07K 2319/60; C07K 2319/71; C07K 2319/80; C07K 2319/85; C07K 14/195; C07K 19/00; C07K 2319/00; C12Y 301/21004; A61P 31/12

See application file for complete search history.

(56) References Cited

U.S. PATENT DOCUMENTS 5,034,506 A 7/1991 Summerton et al.
5,489,677 A 2/1996 Sanghvi et al.
(Continued)

FOREIGN PATENT DOCUMENTS

CN 103224947 A 7/2013
CN 103233028 A 8/2013
(Continued)

OTHER PUBLICATIONS

Sinkunas et. al. Cas3 is a single-stranded DNA nuclease and ATP-dependent helicase in the CRISPR/Cas immune system. The EMBO Journal. 2011. 30(7) 1335-1342 (Year: 2011).*
(Continued)

*Primary Examiner* — Jennifer Dunston
*Assistant Examiner* — Tiffany Nicole Grooms
(74) *Attorney, Agent, or Firm* — Barbara G. McClung; Euk Charlie Oh

(57) ABSTRACT

A clustered regularly interspaced short palindromic repeat (CRISPR)-associated complex for adaptive antiviral defence (Cascade); the Cascade protein complex comprising at least CRISPR-associated protein subunits Cas7, Cas5 and Cas6 which includes at least one subunit with an additional amino acid sequence possessing nucleic acid or chromatin modifying, visualising, transcription activating or transcription repressing activity. The Cascade complex with additional activity is combined with an RNA molecule to produce a ribonucleoprotein complex. The RNA molecule is selected to have substantial complementarity to a target sequence. Targeted ribonucleoproteins can be used as genetic engineering tools for precise cutting of nucleic acids in homologous recombination, non-homologous end joining, gene modification, gene integration, mutation repair or for their visualisation, transcriptional activation or repression. A pair of ribonucleotides fused to FokI dimers may be used to generate double-strand breakages in the DNA to facilitate these applications in a sequence-specific manner.

16 Claims, 25 Drawing Sheets

Specification includes a Sequence Listing.

Related U.S. Application Data continuation of application No. 16/914,203, filed on Jun. 26, 2020, now Pat. No. 10,954,498, which is a continuation of application No. 16/554,225, filed on Aug. 28, 2019, now Pat. No. 10,711,257, which is a continuation of application No. 15/802,413, filed on Nov. 2, 2017, now Pat. No. 10,435,678, which is a continuation of application No. 14/997,474, filed on Jan. 15, 2016, now Pat. No. 9,885,026, which is a continuation of application No. 14/326,099, filed on Jul. 8, 2014, now abandoned, which is a continuation of application No. 14/240,735, filed as application No. PCT/EP2012/076674 on Dec. 21, 2012, now abandoned.

(51) Int. Cl.

| | |
|---|---|
| ***C12N 15/81*** | (2006.01) |
| ***C12N 15/82*** | (2006.01) |
| ***C12N 15/86*** | (2006.01) |
| ***C12N 15/90*** | (2006.01) |

(56) References Cited

U.S. PATENT DOCUMENTS

| | | | |
|---|---|---|---|
| 5,602,240 | A | 2/1997 | De Mesmaeker et al. |
| 5,766,900 | A | 6/1998 | Shillito et al. |
| 5,767,367 | A | 6/1998 | Dudits et al. |
| 5,968,738 | A | 10/1999 | Anderson et al. |
| 6,066,476 | A | 5/2000 | Tsien et al. |
| 6,306,610 | B1 | 10/2001 | Bawendi et al. |
| 7,919,277 | B2 | 4/2011 | Russell et al. |
| 8,361,725 | B2 | 1/2013 | Russell et al. |
| 8,546,553 | B2 | 10/2013 | Terns et al. |
| 8,685,737 | B2 | 4/2014 | Serber et al. |
| 8,697,359 | B1 | 4/2014 | Zhang |
| 8,771,945 | B1 | 7/2014 | Zhang |
| 8,795,965 | B2 | 8/2014 | Zhang |
| 8,921,332 | B2 | 12/2014 | Choulika et al. |
| 9,885,026 | B2 | 2/2018 | Brouns |
| 10,227,576 | B1 | 3/2019 | Cameron et al. |
| 10,329,547 | B1 | 6/2019 | Cameron et al. |
| 10,435,678 | B2 | 10/2019 | Brouns et al. |
| 10,457,922 | B1 | 10/2019 | Cameron et al. |
| 10,597,648 | B2 | 3/2020 | Cameron et al. |
| 10,711,257 | B2 | 7/2020 | Brouns et al. |
| 10,781,432 | B1 | 9/2020 | Cameron et al. |
| 10,954,498 | B2 | 3/2021 | Brouns et al. |
| 11,555,181 | B2 | 1/2023 | Cameron et al. |
| 11,939,604 | B2 | 3/2024 | Brouns et al. |
| 12,227,776 | B2 | 2/2025 | Cameron et al. |
| 2002/0119570 | A1 | 8/2002 | Yoon et al. |
| 2002/0182673 | A1 | 12/2002 | Chen et al. |
| 2003/0232410 | A1 | 12/2003 | Liljedahl et al. |
| 2004/0111221 | A1 | 6/2004 | Beattie et al. |
| 2005/0026157 | A1 | 2/2005 | Baltimore et al. |
| 2005/0208489 | A1 | 9/2005 | Carroll et al. |
| 2006/0147980 | A1 | 7/2006 | Keene et al. |
| 2006/0199190 | A1 | 9/2006 | Russell et al. |
| 2006/0253913 | A1 | 11/2006 | Huang et al. |
| 2007/0016012 | A1 | 1/2007 | Hartlep et al. |
| 2007/0134796 | A1 | 6/2007 | Holmes et al. |
| 2007/0218528 | A1 | 9/2007 | Miller |
| 2008/0124725 | A1 | 5/2008 | Barrangou et al. |
| 2008/0159996 | A1 | 7/2008 | Ando et al. |
| 2009/0227029 | A1 | 9/2009 | Radman et al. |
| 2010/0034924 | A1 | 2/2010 | Fremaux et al. |
| 2010/0047805 | A1 | 2/2010 | Wang |
| 2010/0055728 | A1 | 3/2010 | Yang et al. |
| 2010/0076057 | A1 | 3/2010 | Sontheimer et al. |
| 2010/0093617 | A1 | 4/2010 | Barrangou et al. |
| 2010/0104690 | A1 | 4/2010 | Barrangou et al. |
| 2011/0002889 | A1 | 1/2011 | Barrangou et al. |
| 2011/0041195 | A1 | 2/2011 | Doyon |
| 2011/0082093 | A1 | 4/2011 | Gregory et al. |
| 2011/0105364 | A1 | 5/2011 | Kurn |
| 2011/0145940 | A1 | 6/2011 | Voytas et al. |
| 2011/0182867 | A1 | 7/2011 | Orkin et al. |
| 2011/0189776 | A1 | 8/2011 | Terns et al. |
| 2011/0203012 | A1 | 8/2011 | Dotson et al. |
| 2011/0207221 | A1 | 8/2011 | Cost et al. |
| 2011/0217739 | A1 | 9/2011 | Terns et al. |
| 2011/0223638 | A1 | 9/2011 | Wiedenheft et al. |
| 2011/0236530 | A1 | 9/2011 | Manoury et al. |
| 2011/0287545 | A1 | 11/2011 | Cost et al. |
| 2011/0294114 | A1 | 12/2011 | Van Der Loo et al. |
| 2011/0300538 | A1 | 12/2011 | Barrangou et al. |
| 2011/0301073 | A1 | 12/2011 | Gregory et al. |
| 2012/0029891 | A1 | 2/2012 | Behlke et al. |
| 2012/0149115 | A1 | 6/2012 | Kim et al. |
| 2012/0192298 | A1 | 7/2012 | Weinstein et al. |
| 2012/0196370 | A1 | 8/2012 | Urnov et al. |
| 2012/0230971 | A1 | 9/2012 | Choulika et al. |
| 2012/0324603 | A1 | 12/2012 | Hlubek et al. |
| 2013/0011828 | A1 | 1/2013 | Barrangou et al. |
| 2013/0017541 | A1 | 1/2013 | Forsyth |
| 2013/0065310 | A1 | 3/2013 | Davis et al. |
| 2013/0130248 | A1 | 5/2013 | Haurwitz et al. |
| 2013/0145497 | A1 | 6/2013 | Choi et al. |
| 2013/0158245 | A1 | 6/2013 | Russell et al. |
| 2013/0253040 | A1 | 9/2013 | Miller et al. |
| 2013/0288251 | A1 | 10/2013 | Horvath et al. |
| 2013/0326645 | A1 | 12/2013 | Cost et al. |
| 2013/0326725 | A1 | 12/2013 | Shukla et al. |
| 2013/0330778 | A1 | 12/2013 | Zeiner et al. |
| 2014/0017212 | A1 | 1/2014 | Rebar |
| 2014/0017214 | A1 | 1/2014 | Cost |
| 2014/0045176 | A1 | 2/2014 | Kim et al. |
| 2014/0068797 | A1 | 3/2014 | Doudna et al. |
| 2014/0080216 | A1 | 3/2014 | Cost et al. |
| 2014/0090112 | A1 | 3/2014 | Cogan et al. |
| 2014/0090113 | A1 | 3/2014 | Cogan et al. |
| 2014/0090116 | A1 | 3/2014 | Ainley et al. |
| 2014/0112896 | A1 | 4/2014 | Rebar |
| 2014/0123330 | A1 | 5/2014 | Carlson et al. |
| 2014/0127752 | A1 | 5/2014 | Zhou et al. |
| 2014/0170753 | A1 | 6/2014 | Zhang |
| 2014/0178770 | A1 | 6/2014 | Feng et al. |
| 2014/0179006 | A1 | 6/2014 | Zhang |
| 2014/0186843 | A1 | 7/2014 | Zhang et al. |
| 2014/0186919 | A1 | 7/2014 | Zhang |
| 2014/0186958 | A1 | 7/2014 | Zhang et al. |
| 2014/0189896 | A1 | 7/2014 | Zhang et al. |
| 2014/0199767 | A1 | 7/2014 | Barrangou et al. |
| 2014/0294773 | A1 | 10/2014 | Brouns |
| 2014/0295556 | A1 | 10/2014 | Joung et al. |
| 2015/0024499 | A1 | 1/2015 | Brouns et al. |

FOREIGN PATENT DOCUMENTS

| | | | |
|---|---|---|---|
| CN | 103343120 | A | 10/2013 |
| EP | 2292731 | A1 | 3/2011 |
| EP | 2341149 | A1 | 7/2011 |
| EP | 2489275 | A1 | 8/2012 |
| EP | 2674501 | A1 | 12/2013 |
| WO | WO1988008450 | A1 | 11/1988 |
| WO | WO1993019191 | A1 | 9/1993 |
| WO | WO2002034771 | A2 | 5/2002 |
| WO | WO2006073445 | A2 | 7/2006 |
| WO | WO2007025097 | A2 | 3/2007 |
| WO | WO2007136815 | A2 | 11/2007 |
| WO | WO2007144770 | A2 | 12/2007 |
| WO | WO2008108989 | A2 | 9/2008 |
| WO | WO2009115861 | A2 | 9/2009 |
| WO | WO2010011961 | A2 | 1/2010 |
| WO | WO2010054108 | A2 | 5/2010 |
| WO | WO2010054154 | A2 | 5/2010 |
| WO | WO2010066907 | A1 | 6/2010 |
| WO | WO2010075424 | A2 | 7/2010 |
| WO | WO2010117464 | A1 | 10/2010 |
| WO | WO2010125471 | A2 | 11/2010 |
| WO | WO2011011767 | A1 | 1/2011 |
| WO | WO2011143124 | A2 | 11/2011 |

(56) References Cited

FOREIGN PATENT DOCUMENTS

| | | | |
|---|---|---|---|
| WO | WO2011156430 | A2 | 12/2011 |
| WO | WO2012012738 | A1 | 1/2012 |
| WO | WO2012054726 | A1 | 4/2012 |
| WO | WO2012164565 | A1 | 12/2012 |
| WO | WO2013044008 | A2 | 3/2013 |
| WO | WO2013082519 | A2 | 6/2013 |
| WO | WO2013088446 | A1 | 6/2013 |
| WO | WO2013098244 | A1 | 7/2013 |
| WO | WO2013126794 | A1 | 8/2013 |
| WO | WO2013130824 | A1 | 9/2013 |
| WO | WO2013141680 | A1 | 9/2013 |
| WO | WO2013142578 | A1 | 9/2013 |
| WO | WO2013155572 | A1 | 10/2013 |
| WO | WO2013160230 | A1 | 10/2013 |
| WO | WO2013169398 | A2 | 11/2013 |
| WO | WO2013169802 | A1 | 11/2013 |
| WO | WO2013176772 | A1 | 11/2013 |
| WO | WO2013181440 | A1 | 12/2013 |
| WO | WO2013186754 | A2 | 12/2013 |
| WO | WO2013188522 | A2 | 12/2013 |
| WO | WO2013188638 | A2 | 12/2013 |
| WO | WO2013192278 | A1 | 12/2013 |
| WO | WO2014011237 | A1 | 1/2014 |
| WO | WO2014011901 | A2 | 1/2014 |
| WO | WO2014018423 | A2 | 1/2014 |
| WO | WO2014039684 | A1 | 3/2014 |
| WO | WO2014039692 | A2 | 3/2014 |
| WO | WO2014039702 | A2 | 3/2014 |
| WO | WO2014039872 | A1 | 3/2014 |
| WO | WO2014059255 | A1 | 4/2014 |
| WO | WO2014065596 | A1 | 5/2014 |
| WO | WO2014071006 | A1 | 5/2014 |
| WO | WO2014089290 | A1 | 6/2014 |
| WO | WO2014093595 | A1 | 6/2014 |
| WO | WO2014093622 | A2 | 6/2014 |
| WO | WO2014093635 | A1 | 6/2014 |
| WO | WO2014093655 | A2 | 6/2014 |
| WO | WO2014093661 | A2 | 6/2014 |
| WO | WO2014093694 | A1 | 6/2014 |
| WO | WO2014093701 | A1 | 6/2014 |
| WO | WO2014093709 | A1 | 6/2014 |
| WO | WO2014093712 | A1 | 6/2014 |
| WO | WO2014093718 | A1 | 6/2014 |
| WO | WO2014099744 | A1 | 6/2014 |
| WO | WO2014099750 | A2 | 6/2014 |
| WO | WO2014104878 | A1 | 7/2014 |
| WO | WO2014113493 | A1 | 7/2014 |

OTHER PUBLICATIONS

U.S. Appl. No. 14/997,474, filed Jan. 15, 2016, now U.S. Pat. No. 9,885,026, Feb. 6, 2018.

U.S. Appl. No. 15/802,413, filed Nov. 2, 2017, now U.S. Pat. No. 10,435,678, Oct. 8, 2019.

U.S. Appl. No. 16/554,225, filed Aug. 28, 2019, now U.S. Pat. No. 10,711,257, Jul. 14, 2020.

U.S. Appl. No. 16/914,203, filed Jun. 26, 2020, now U.S. Pat. No. 10,954,498, Mar. 23, 2021.

U.S. Appl. No. 17/179,215, filed Feb. 18, 2021, allowed.

U.S. Appl. No. 16/104,875, filed Aug. 17, 2018, now U.S. Pat. No. 10,227,576, Mar. 12, 2019.

U.S. Appl. No. 16/262,773, filed Jan. 30, 2019, now U.S. Pat. No. 10,329,547, Jun. 25, 2019.

U.S. Appl. No. 16/420,061, filed May 22, 2019, now U.S. Pat. No. 10,457,922, Oct. 29, 2019.

U.S. Appl. No. 16/665,316, filed Oct. 28, 2019, now U.S. Pat. No. 10,597,648, Mar. 24, 2020.

U.S. Appl. No. 16/824,603, filed Mar. 19, 2020, now U.S. Pat. No. 10,781,432, Sep. 22, 2020.

U.S. Appl. No. 17/027,257, filed Sep. 21, 2020, now U.S. Pat. No. 11,555,181, Jan. 17, 2023.

U.S. Appl. No. 17/120,081, filed Dec. 11, 2020, pending.

Haft, et al. A Guild of 45 CRISPR-Associated (Cas) Protein Families and Multiple CRISPR/Cas Subtypes Exist in Prokaryotic Genomes, 1(6) PLoS COMPUT. BIOL. 474-483 (2005).

Hale, et al. RNA-Guided RNA Cleavage by a CRISPR RNA-Cas Protein, 139(5) CELL 945-956 (2009).

Hauwitz, et al. Sequence- and structure-specific RNA processing by a CRISPR endonuclease, 329 SCIENCE 1355-1358 (2010).

Mojica, et al. Biological significance of a family of regularly spaced repeats in the genomes of Archaea, Bacteria and mitochondria, 36(1) MOL. MICROBIOL. 244-246 (2000).

Pourcel, et al. CRISPR elements in Yersinia pestis acquire new repeats by preferential uptake of bacteriophage DNA, and provide additional tools for evolutionary studies, 151 MICROBIOL. READ. ENGL. 653-663 (2005).

Deveau, et al., Phage response to CRISPR-encoded resistance in *Streptococcus thermophilus*. J. Bacterial (Feb. 2008), 190(4 ): 1390-400.

Mastroianni, et al., Group II intron-based gene targeting reactions in eukaryotes. PLoS One. (Sep. 2008), 3 (9):e3121.

Raymond, et al., High-efficiency FLP and PhiC31 site-specific recombination in mammalian cells. PLoS One. (Jan. 2007). 2(1):e162.

Karpala, et al. Immune responses to dsRNA: Implications for gene silencing technologies. Immunology and Cell Biology, (2005) 83:211-216.

Koseki, et al. Factors Governing he Activity In Vivo of Ribozymes Transcribed by RNA Polymerase III. Journal of Virology,(1999) 73(3):1868-1877.

Link, et al. Engineering ligand-responsive gene-control elements: lessons learned from natural riboswitches. Gene Therapy, (2009) 16:1188-1201.

Wirtz, et al. Regulated processive transcription of chromatin by T7 RNA polymerase in Trypanosome brucei. Nucleic Acids Research, (1998) 26(20) :4626-4634.

Wu, et al. Helicase-inactivating mutations as a basis dominant negative phenotypes. Cell Cycle, (2010) 9 (20):4080-4090.

NP_ 41724.1 (Cas3 predicted halicase needed or Cascade anti-viral activity, NCBI Reference Sequence, priority to Oct. 25, 2010, 3 pages).

Cameron, et al. Harnessing type I CRISPR-Cas systems for genome engineering in human cells. Nature Biotechnology, (2019) 37:1471-1477.

Al-Attar, et al. Clustered regularly interspaced short palindromic repeats (CRISPRs): the hallmark of an ingenious antiviral defense mechanism in prokaryotes. Biol Chem. Apr. 2011;392(4):277-89. doi: 10.1515/BC.2011.042. Epub Feb. 7, 2011.

Anguela, et al. In Vivo Genome Editing of Liver Albumin for Therapeutic Gene Expression: Rescue of Hemophilic Mice via Integration of Factor 9. 54th ASH Annual eating and Exposition, Dec. 10, 2012, Atlanta, Georgia.

Barranger, et al. Gene transfer approaches to the lysosomal storage disorders. Neurochem Res. Apr. 1999,24(4):601-15.

Barrangou, et al. CRISPR Provides Acquired Resistance Against Viruses in Prokaryotes. Science, 2007, vol. 313, pp. 1709-1712.

Barras. Right on Target: New Era of Fast Genetic Engineering. New Scientist, Jan. 2014, vol. 2953.

Beloglazov A, et al. A novel family of sequence-specific endoribonucleases associated with the clustered regularly interspaced short palindromic repeats, J Biol Chem. Jul. 18, 2008,283(29):20361-71. doi: 10.1074/jbc.M803225200, Epub May 15, 2008.

Beres et al. Genome sequence of a serotype M3 strain of group A Streptococcus: phage-encoded toxins, the high-virulence phenotype, and clone emergence. Proc Natl Acad Sci U S A. Jul. 23, 2002;99(15):10078-83. Epub Jul. 16, 2002.

Biffi, et al. Genetically-modified hematopoietic stem cells and their progeny for widespread and efficient protein delivery to diseased sites: the case of lysosomal storage disorders. Curr Gene Ther. Oct. 2012;l2(5):381-8.

Biffi, et al. Metachromatic Leukodystrophy: an Overview of Current and Prospective Treatments. Bone Marrow Transplantation, 2008, vol. 42, pp. 82-86.

Bolotin, et al., Clustered regularly interspaced short palindrome repeats (CRISPRs) have spacers of extrachromosomal origin. Microbiology. Aug. 2005; 151 (Pt 8):2551-61.

(56) References Cited

OTHER PUBLICATIONS

Bolotin, et al. Complete sequence and comparative genome analysis of the dairy bacterium *Streptococcus thermophilus*. Nat Biotechnol. Dec. 2004;22(12): 1554-8. Epub Nov. 14, 2004.
Carroll. a CRISPR approach to gene targeting. Mol Ther. Sep. 2012;20(9):1658-60. doi: 10.1038/mt.2012.I71.
Cermak, et al. Efficient design and assembly of custom TALEN and other TAL effector-based constructs or DNA targeting. Nucleic Acids Res. Jul. 2011:39(12):e82. doi: 10.1093/nar/gkr218. Epub Apr. 14, 2011.
Charpentier, Abstracts of the Interscience Conference on Antimicrobial Agents and Chemotherapy, 2012, 52, 1785.
Cong et al. Comprehensive Interrogation of natural TALE DNA-binding modules and transcriptional repressor domains. Nat Commun, Jul. 24, 2012:3:968. doi: 10.103 8/ncomms 1962.
Courtin, et al., "Interactions Between Microorganisms in a Simple Ecosystem: Yogurt Bacteria as a Study Model", LAIT, 2004, vol. 84, pp. 125-134.
Cradick, et al. ZFN-site searches genomes for zinc finger nuclease target sites and off-target sites. BMC Bioinformatics. May 13, 2011;12: 152. doi: 10.1186/1471-2105-12-152.
Dagnino, et al. Molecular diagnosis of analbuminemia: a new case caused by a nonsense mutation in the albumin gens. Int J Mol Sci. 2011;12(11):7313-22. doi: 10.3390/ijmsl2117314. Epub Oct. 25, 2011.
Editas Press Release, "Editas Medicine Created to Discover and Develop Novel Class of Genome Editing Therapeutics", Nov. 25, 2013.
Ferretti, et al. Complete genome sequence of an MI strain of Streptococcus pyrogenes. Proc Natl Acad Sci U S A. Apr. 10. 2011;98(8):4658-63.
Fu, et al. Improving CRISPR-Cas nuclease specificity using truncated guide RNAs. Nat Biotechnol. Mar. 2014;32(3):279-84. doi: 10.1038/nbt.2808. Epub Jan. 26, 2014.
Gaj, et al. ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Garneau, et al. The CRISPR/Cas bacterial immune system cleaves bacteriophage and plasmid DNA. Nature. Nov. 4, 2010;468(7320):67-71. doi: 10.1038/nature09523.
GenBank Accession No. AAL81255, Feb. 25, 2002, "hypothetical protein PF 1131 [*Pyrococcus furiosus* DSM 3638]".
Gentner et al., Identification ofhematopoietic stem cell-specific miRNAs enables gene therapy of globoid cell leukodystrophy. Sci Transl Med. Nov. 17, 2010;2(58):58ra84. doi: 10.I 126/scitransimed. 3001522.
Gilbert, et al. CRISPR-mediated modular RNA-guided regulation of transcription in eukaryotes, Cell. Jul. 18, 2013,154(2):442-51. doi: 10.1016/j.cell.2013.06.044. Epub Jul. 11, 2013.
Grabowski. Phenotype, diagnosis, and treatment ofGaucher's disease. Lancet. Oct. 4, 2008;372(9645): 1263-71. doi: 10.1016/S0140-6736(08)61522-6.
Gray, et al., Malurase [Neosartorya fischeri] GenBank Accension No. AAX39426, May 19, 2005.
Gritti. Gene therapy for lysosomal storage disorders. Expert Opin Biol Ther. Sep. 2011;I 1(9): 1153-67 doi: 10.1517/14712598.201 1.582036. Epub May 9, 2011.
Gupta, et al., Zinc finger protein-dependent and -independent contributions to the in vivo off-target activity of zinc finger nucleases. Nucleic Acids Res. Jan. 2011;39(1 ):381-92. doi: 10.1093/nar/gkq787. Epub Sep. 14, 2010.
Hale, et al. Prokaryotic silencing (psi)RNAs in *Pyrococcus furiosus*. RNA. Dec. 2008;14(12):2572-9. doi: 10.1261/ma.1246808. Epub Oct. 29, 2008.
Hatoum-Aslan, et al. Mature clustered, regularly interspaced, short palindromic repeats RNA ( crRNA) length is measured by a ruler mechanism anchored at the precursor processing site. Proc Natl Acad Sci U S A. Dec. 27, 2011;108(52):21218-22. doi: 10.1073/pnas.1112832108. Epub Dec. 12, 2011.
Hockmeyer, et al. Efficient targeting of expressed and silent genes in human ESCs and iPSCs using zinc-finger nucleases. Nat Biotechnol. Sep. 2009;27(9):85 I-7. doi: 10.1038/nbt.1562. Epub Aug. 13, 2009.
Hockmeyer, et al. Genetic engineering of human pluripotent cells using TALE nucleases. Nat Biotechnol. Jul. 7, 2011;29(8):731-4. doi: 10.1038/nbt.1927.
Hofling, et al. Human CD34+ hematopoletic progenitor cell-directed lentiviralmediated gene therapy in a xenotransplantation model of lysosomal storage disease.Mol Ther. Jun. 2004;9(6):856-65.
Hsu, et al. DNA targeting specificity of RNA-guided Cas9 nucleases. Nat Biotechnol Sep. 2013;31(9):827-32. doi: 10.1038/nbt.2647. Epub Jul. 21, 2013.
Ishino, et al. Nucleotide sequence of the lap gene, responsible for alkaline phosphatase isozyme conversion in *Escherichia coli*, and identification of the gene product. J Bacteriol. Dec. 1987;I69(12):5429-33.
Jacoby, et al. Expanding LAGLIDADG endonuclease scaffold diversity by rapidly surveying evolutionary sequence space. Nucleic Acids Res. Jun. 2012;40(1 I):4954-64. doi: 10.1093/nar/gkr1303. Epub Feb. 14, 2012.
Jacoby, et al., "Chain A, Expanding LAGLIDADG Endonuclease Scaffold Diversity by Rapidly Surveying Evolutionary Sequence Space", GenBank Record Accession No. 3UVF A, Oct. 10, 2012.
Jacoby, et al., TPA_exp: LAGLIDADG Endonuclease, partial (mitochondrion) [Trichoderma reesei], GenBank Accession No. DAA35 I 82, Jun. 30, 2012.
Kennedy, et al. Rapid blue-light-mediated induction of protein interactions in living cells. Nat Methods. Dec. 2010;7(12):973-5. doi: 10.1038/nmeth.1524. Epub Oct. 31, 2010.
Kim, et al. Long-term expression of the human glucocerebrosidase gene in vivo after transplantation of bone-marrow-derived cells transformed with a lentivirus vector. J Gene Med. Jul. 2005;7(7):878-87.
Leimig, et al. Functional amelioration of murine galactosialidosis by genetically modified bone marrow hematopoietic progenitor cells. Blood. May 1, 2002;99(9):3169-78.
Li, et al. High-efficiency TALEN-based gene editing produces disease-resistant rice. Nal Biotechnol. May 7, 2012;30(5):390-2. doi: 10.1038/nbt.2199.
Luo, et al. Highly parallel identification of essential genes in cancer cells. Proc Natl Acad Sci US A. Dec. 23, 2008;105(51):20380-5. doi: 10.1073/pnas.0810485105. Epub Dec. 17, 2008.
Ma, et al. A guide RNA sequence design platform for the CRISPR/Cas9 system for model organism genomes. Biomed Res Int. 2013;2013:270805. doi: 10.I 155/2013/270805. Epub Oct. 3, 2013.
Malanowska, et al. CTnDOT integrase performs ordered homology-dependent and homology-independent strand exchanges. Nucleic Acids Res. 2007;35(17):5861-73. Epub Aug. 24, 2007.
Marrafini, et al. Self versus non-self discrimination during CRISPR RNA-directed immunity. Nature. Jan. 28, 2010;463(7280):568-71. doi: 10.1038/nature08703. Epub Jan. 13, 2010.
Mittelman, et al. Zinc-finger directed double-strand breaks within CAG repeat tracts promote repeat instability in human cells. Proc Natl Acad Sci US A. Jun. 16, 2009;106(24):9607-12. doi: 10.1073/pnas.0902420106. Epub May 29, 2009.
Mojica, et al. Intervening sequences of regularly spaced prokaryotic repeats derive from foreign genetic elements. J Mol Evol. Feb. 2005;60(2): 174-82.
Mojica, et al. Long stretches of short tandem repeats are present in the largest replicons of the Archaea Haloferax mediterranei and Haloferax volcanil and could be involved in replicon partitioning. Mol Micro biol. Jul. 1995; 17(1 ): 85-93.
Mojica, et al. Short motif sequences determine the targets of the prokaryotic CRISPR defence system. Microbiology. Mar. 2009;I55(Pt 3):733-40. doi: 10.1099/mic.0.023960-0.
Moore, et al. Improved somatic mutagenesis in zebrafish using transcription activator-like effector nucleases (TALENs). S One, 2012;7(5):e37877. doi: 10.1371/journal.pone.0037877. Epub May 24, 2012.
Moscou, et al. A simple cipher governs DNA recognition by TAL effectors. Science. Dec. 11, 2009:326(5959):1501. doi: 10.1126/science.1178817.

(56) References Cited

OTHER PUBLICATIONS

Muzykantov. Drug delivery by red blood cells: vascular carriers designed by mother nature. Expert Opin Drug Deliv. Apr. 2010;7(4):403-27. doi: 10.1517 /I 7425241003610633.
Orlando, et al. Zinc-finger nuclease-driven targeted integration into mammalian genomes using donors with limited chromosomal homology. Nucleic Acids Res. Aug. 2010:38(15):eI52. doi: 10.1093/nar/gkq512. Epub Jun. 8, 2010.
Papapetrou, et al. Genomic safe harbors permit high β-globin transgene expression in thalassemia induced pluripotent stem cells. Nat Biotechnol. Jan. 2011;29(1 ):73-8. doi: 10.1038/nbt.I 717. Epub Dec. 12, 2010.
Pattanayak, et al. Revealing off-target cleavage specificities of zinc-finger nucleases by in vitro selection. Nat Methods. Aug. 7, 2011;8(9):765-70. doi: 10.1038/nmeth.1670.
Pennisi. The CRISPR craze. Science. Aug. 23, 2013;341(6148):833-6. doi: 10.I 126/science.341.6148.833.
Povirk, et al., "Role of Braca 1 in Nonhomologous DNA End Joining", U.S. Army Medical Research and Material Command, Award No. DAMD 17-03-01-0620, Sep. 2004, pp. 1-11.
Ramsubir, et al. In vivo delivery of human acid ceramidase via cord blood transplantation and direct injection of lentivirus as novel treatment approaches for Farber disease. Mol Genet Metab. Nov. 2008;95(3): 133-41. doi:10.1016/j.ymgme.2008.08.003. Epub Sep. 20, 2008.
Rho, et al. Diverse CRISPRs evolving in human microbiomes. PLoS Genet. 2012;8(6):e1002441. doi: 10.1371/journal.pgen.1002441. Epub Jun. 13, 2012.
Sampson, et al. A CRISPR/Cas system mediates bacterial innate immune evasion and virulence. Nature. May 9, 2013;497(7448):254-7. doi: 10.1038/naturel2048. Epub Apr. 14, 2013.
Sanjana, et al. A transcription activator-like effector toolbox for genome engineering. Nat Protoc. Jan. 5, 2012;7(1 ): 171-92. doi: 10.1038/nprot.201 I.43 I.
Shalem, et al. Genome-scale CRISPR-Cas9 knockout screening in human cells. Science. Jan. 3, 2014;343(6166):84-7. doi: 10.1126/science.1247005. Epub Dec. 12, 2013.
Sims, et al. High-throughput RNA interference screening using pooled shRNA libraries and next generation sequencing. Genome Biol. Oct. 21, 2011;12(10):RI04. doi: 10.II 86/gb-201 I-12-10-rl04.
Sontheimer et al., "Project 7: Establishing RNA-Directed DNA Targeting in Eukaryotic Cells; Project dates: Nov. 16, 2011 to Dec 31, 2012" (Feb. 4, 2012).
Sorek et al. CRISPR-mediated adaptive immune systems in bacteria and archaea. Annu Rev Biochem. 2013;82:237-66. doi: 10. I 146/annurev-biochem-072911-172315. Epub Mar. 11, 2013.
Stern, et al. Self-targeting by CRISPR: gene regulation or autoimmunity? Trends Genet. Aug. 2010;26(8):335-40. doi: 10.1016/j.tig.2010.05.008. Epub Jul. 1, 2010.
Sun, et al. Optimized TAL effector nucleases (TALENs) for use in treatment of sickle cell disease. Mol Biosyst. Apr. 2012;8(4):1255-63. doi: 10.1039/c2mb0546lb. Epub Feb. 3, 2012.
Tan, et al. Precision editing of large animal genomes. Adv Genet. 2012;80:37-97. doi: 10.10 I 6/B978-0-12-404 742-6.00002-8.
Terns, et al. The CRISPR-Cas system: small RNA-guided invader small RNA-guided invader silencing in prokaryotes. The FASEB J. 2012, vol. 26, Abstract 353.3.
Urnov, et al. Highly efficient endogenous human gene correction using designed zinc-finger nucleases. Nature. Jun. 2, 2005;435(7042):646-51. Epub Apr. 3, 2005.
Van Til, et al. Lentiviral gene therapy of murine hematopoietic stem cells ameliorates the Pompe disease phenotype. Blood. Jul. 1, 2010;115(26):5329-37. doi: 10.1182/blood-2009-11-252874. Epub Apr. 12, 2010.
Wang, et al. Genetic correction of ?-thalassemia patient-specific IPS cells and its use in improving hemoglobin production in irradiated SCID mice. Cell Res. Apr. 2012;22(4):637-48. doi: 10.1038/cr.2012.23. Epub Feb. 7, 2012.
Wang, et al. Reprogramming erythroid cells for lysosomal enzyme production leads to visceral and CNS cross-correction in mice with Hurler syndrome. Proc Natl Acad Sci U S.A. Nov. 24, 2009;106(47):19958-63. doi: 10.1073/pnas.0908528106. Epub Nov. 10, 2009.
Wang, et al. Spatiotemporal control of gene expression by a light-switchable transgene system. Nat Methods. Feb. 12, 2012;9(3):266-9. doi: 10.1038/nmeth.1892.
Zhang, et al. cSSMD: assessing collective activity for addressing off-target effects in genome-scale RNA interference screens. Bioinformatics. Oct. 15, 2011;27(20):2775-81. doi: 10.1093/bioinformatics/btr474. Epub Aug. 16, 2011.
Zhou, et al. Mouse model for the lysosomal disorder galactosialidosis and correction of the phenotype with overexpressing erythroid precursor cells. Genes Dev. Nov. 1, 1995 ;9(21):2623-34.
Aguilera, et al. Systemic in vivo distribution of activatable cell penetrating peptides is superior to that of cell penetrating peptides. Integr Biol (Camb). Jun. 2009;I(5-6):371-81. doi: 10.1039/b904878b. Epub May 11, 2009.
Amantana, et al. Pharmacokinetics, biodistribution, stability and toxicity of a cellpenetrating peptide-morpholino oligomer conjugate. Bioconjug Cher. Jul.-Aug. 2007;I8(4):1325-31. Epub Jun. 21, 2007.
Barrangou, R. RNA-mediated programmable DNA cleavage. Nat Biotechnol. Sep. 2012;30(9): 836-8. doi: 10.103 8/nbt.2357.
Bassett, et al. Highly Efficient Targeted Mutagenesis of Drosophila with the CRISPR/Cas9 System. Cell Rep. Jul. 11, 2013;4(1):220-8. doi: 10.1016/j.celrep.2013.06.020. Epub Jul. 1, 2013.
Bhay A, et al. CRISPR-Cas systems in bacteria and archaea: versatile small RNAs for adaptive defense and regulation. Annu Rev Genet. 2011:45:273-97. doi: 10.I 146/annurev-genet-110410-132430.
Brouns, et al. Small CRISPR RNAs guide antiviral defense in prokaryotes. Science. Aug. 15, 2008:321(5891):960-4. doi: 10.1126/science.1159689.
Carr, et al. Genome engineering. Nat Biotechnol. Dec. 2009;27(12):1151-62. doi: 10 .103 8/nbt. 1590.
Carte, et al. Cas6 is an endoribonuclease that generates guide RNAs for invader defense in prokaryotes. Genes Dev. Dec. 15, 2008;22(24):3489-96. doi: 10.1101/gad.1742908.
Cho, et al. Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Chylinski, et al. The tracrRNA and Cas9 families of type II CRISPR-Cas immunity systems. RNA Biol. May 2013;10(5):726-737. doi: 10.4161/ma.24321. Epub Apr. 5, 2013.
Cong, et al. Multiplex genome engineering using CRISPR/Cas systems. Science. Feb. 15, 2013;339(6121):819-23. doi: 10.1126/science.1231143. Epub Jan. 3, 2013.
Dame, et al. H-NS mediated compaction of DNA visualised by atomic force microscopy. Nucleic Acids Res. Sep. 15, 2000;28(18):3504-10.
Dekelver, et al. Functional genomics, proteomics, and regulatory DNA analysis in isogenic settings using zinc finger nuclease-driven transgenesis into a safe harbor locus in the human genome. Genome Res. Aug. 2010;20(8): 1133-42. doi: 10.1101/gr.106773.110. Epub May 27, 2010.
Deltchev A, et al. CRISPR RNA maturation by trans-encoded small RNA and host factor RNase III. Nature. Mar. 31, 2011;471(7340):602-7. doi: 10.1038/nature09886.
Donnelly, et al. The 'cleavage' activities of foot-and-mouth disease virus 2A sitedirected mutants and naturally occurring '2A-like' sequences. J Gen Virol. May 2001;82(Pt 5):1027-41.
Doyon, et al. Enhancing zinc-finger-nuclease activity with improved obligate heterodimeric architectures. Nat Methods. Jan. 2011;8(1):74-9. doi: 10.1038/nmeth.1539. Epub Dec. 5, 2010.
Drag, et al. DeSUMOylating enzymes—SENPs. IUBMB Life. Nov. 2008;60(1 I ):734-42. doi: 10.1002/iub.I 13.
Fineran, et al. Degenerate target sites mediate rapid primed CRISPR adaptation. Proc Natl Acad Sci U S A. Apr. 22, 2014;1 I 1(16):EI629-38. doi: 10.1073/pnas.1400071111. Epub Apr. 7, 2014.
Friedland, et al. Heritable genome editing in C. elegans via a CRISPR-Cas9 system. Nat Methods. Aug. 2013;10(8):741-3. doi: 10.1038/nmeth.2532. Epub Jun. 30, 2013.

(56) References Cited

OTHER PUBLICATIONS

Fu, et al. High-frequency of-target mutagenesis induced by CRISPR-Cas nucleases in human calls. Nat Biotechnol. Jun. 23, 2013. doi: 10.1038/nbt.2623. [Epub ahead of print].
Gasiunas, et al. Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012.
Grissa, et al. The CRISPRdb database and tools to display CRISPRs and to generate dictionaries of spacers and repeats. BMC Bioinformatics. May 23, 2007;8: 172.
Guo, et al. Directed evolution of an enhanced and highly efficient Fokl cleavage domain for zinc finger nucleases. J Mol Biol. Jul. 2, 2010;400(1):96-107. doi: 10.1016/j.jmb.2010.04.060. Epub May 4, 2010.
Guschin, et al. A rapid and general assay for monitoring endogenous gene modification. Methods Mol Biol. 2010;649:247-56. doi: 10, 1007/978-1-60761-753-2 15.
Hale, et al. Essential features and rational design of CRISPR RNAs that function with the Cas RAMP module complex to cleave RNAs. Mol Cell. Feb. 10, 2012;45(3):292-302. doi: 10.1016/j.molcel.2011.10.023. Epub Jan. 5, 2012.
Haurwitz, et al. The CRISPR endoribonuclease Csy4 utilizes unusual sequence and 17 structure-specific mechanisms to recognize and process crRNAs. Electronic Thesis and Dissertations UC Berkley, pp. 1-108. Spring 2012. entire document URL: <http://escholarship.org/uc/item/Orh5940p>.
Heasman. Morpholino oligos: making sense of antisense? Dev Biol. Mar. 15, 2002;243(2):209-14.
Horvath, et al. CRISPR/Cas, the immune system of bacteria and archaea. Science. Jan. 8, 2010;327(5962): 167-70. doi: 10.126/science.1179555.
Hou, et al. Efficient genome engineering in human pluripotent stem cells using Cas9 from Neisseria meningitidis. oc Natl Acad Sci U S A. Sep. 24, 2013;110(39): 15644-9, doi: 10.1073/pnas.1313587110. Epub Aug. 12, 2013.
Huang, et al. A simple, high sensitivity mutation screening using Ampligase mediated T7 endonuclease I and Surveyor nuclease with microfluidic capillary electrophoresis. Electrophoresis. Mar. 2012;33(5):788-96. doi: 10.1002/elps.201100460. Epub Mar. 21, 2012.
Hudziak, et al. Resistance of morpholino phosphorodiamidate oligomers to enzymatic degradation. Antisense Nucleic Acid Drug Dev. 1996 Winter;6(4):267-72.
Hwang, et al. Efficient genome editing in zebrafish using a CRISPR-Cas system. Nat Biotechnol. Mar. 2013;31(3):227-9. doi: 10.1038/nbt.2501. Epub Jan. 29, 2013.
International search report and written opinion dated Jul. 26, 2013 for PCT/US2013/032589.
International search report dated Mar. 7, 2013 for PCT Application No. EP2012/07664.
Jansen, et al. Identification of genes that are associated with DNA repeats in prokaryotes. Mol Microbiol. Mar. 2002;43(6): 1565-75.
Jiang, et al. RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek, et al. RNA-programmed genome editing in human cells. Elife. 2013;2:e00471. doi: 10.7554/eLife.00471. Epub Jan. 29, 2013.
Jore, et al. Structural basis for CRISPR RNA-guided DNA recognition by Cascade. Nat Struct Mol Biol. May 2011:18(5):529-36. doi: 10.1038/nsmb.2019. Epub Apr. 3, 2011.
Kunin, et al. Evolutionary conservation of sequence and secondary structures in CRIS PR repeats. Genome Biol. 2007 ;8(4):R6 I.
Lillestol, et al. A putative viral defence mechanism in archaeal cells. Archaea. Aug. 2006;2(1 ):59-72.
Lillestol, et al. CRISPR families of the crenarchaeal genus Sulfolobus: bidirectional transcription and dynamic properties. Mol Microbiol. Apr. 2009;72(1):259-72. doi: 10.I I II/j.1365-2958.2009.06641.x. Epub Feb. 23, 2009.
Lintner, et al. Structural and functional characterization of an archaeal clustered regularly interspaced short palindromic repeat (CRISPR)-associated complex for antiviral defense (CASCADE). J Biol Chem. Jun. 17, 2011;286(24):21643-56. doi: 10.1074/jbc.MI 11.238485. Epub Apr. 20, 2011.
Makarova, et al. A putative RNA-interference-based immune system in prokaryotes: computational analysis of the predicted enzymatic machinery, functional analogies with eukaryotic RNAi, and hypothetical mechanisms of action. Biology Direct 2006, 1:7.
Makarova, et al. Evolution and classification of the CRISPR-Cas systems. Nat Rev Microbiol. Jun. 2011;9(6):467-77. doi: 10.1038/nrmicro2577. Epub May 9, 2011.
Makarova, et al. Unification of Cas protein familias and a simple scenario for the origin and evolution of CRISPR-Cas systems. Biol Direct. Jul. 14, 2011;6:38. doi: 10.II 86/1745-6150-6-38.
Makinen, et al. Stable RNA interference: comparison ofU6 and HI promoters in endothelial cells and in mouse brain. J Gene Med. Apr. 2008;8(4):433-41.
Mali, et al. RNA-guided human genome engineering via Cas9. Science. Feb. 15, 2013;339(6121):823-6. doi: 10.1126/science.1232033. Epub Jan. 3, 2013.
Marraffini, et al. CRISPR interference limits horizontal gene transfer in staphylococci by targeting DNA. Science. Dec. 19, 2008;322(5909):1843-5. doi: 10.I 126/science.1165771.
Marraffini, et al. CRISPR interference: RNA-directed adaptive immunity in bacteria and archaea. Nat Rev Genet. Mar. 2010;I 1(3):181-90. doi: 10.1038/nrg2749.
Melton, et al. Efficienptu binli svhietrr, oc istyy nanthd/eosri sc ooufn btriyo wlohgeirce aplulybl iaschteidv. e RNA and RNA hybridization probes from plasmids containing a bacteriophage SP6 promoter. Nucleic Acids Res. Sep. 25, 1984;12(18):7035-56.
Morcos, et al. Vivo-Morpholinos: A non-peptide transported delivers morpholinos into a wide array of mouse tissues. Biotechniques. Dec. 2008;45(6):613-4, 616, 618 passim.
Nagai, et al. A variant of yellow fluorescent protein with fast and efficient maturation for cell-biological applications. Nat Biotechnol. Jan. 2002;20(1):87-90.
Nishimasu, et al. Crystal Structure of Cas9 in Complex with Guide RNA and Target DNA. Cell. 2014;156(5):935-849.
Niu, et al. Generation of Gene-Modified Cynornolgus Monkey via Cas8/RNAMediated Gene Targeting in One-Cell Embryos. Cell. Feb. 13, 2014;156(4):836-43. doi: 10.1016/j.cell.2014.01.027. Epub Jan. 30, 2014.
Olson, et al. In vivo characterization of activatable cell penetrating peptides for targeting protease activity in cancer. Integr Biol (Camb ). Jun. 2009; 1 ( 5-6):3 82-93. doi: 10.1039/b904890a. Epub May 11, 2009.
Partridge, et al. A simple method for delivering morpholino antisense oligos into the cytoplasm of cells. Antisense Nucleic Acid Drug Dev. 1996 Fall;6(3): 169-75.
Perez-Rodriguez, et al. Envelope stress is a trigger ofCRISPR RNA-mediated DNA silencing in *Escherichia coli* Mol Microbiol. Feb. 2011;79(3):584-99, doi: 10.II II /j.1365-2958.2010.07482.x. Epub Dec. 13, 2010.
Qi, et al. Repurposing CRISPR as an RNA-guided platform for sequence-specific control of gene expression. Cell. Feb. 28, 2013,152(5): 1173-83. doi: 10.1016/j .call.2013 .02.022.
Ryan, et al. Cleavage of foot-and-mouth disease virus polyprotein is mediated by residues located within a 19 amino acid sequence. J Gen Virol. Nov. 1981,72 ( Pt 11 ):2727-32.
Sapranauskas, et al. The *Streptococcus thermophilus* CRISPR/Cas system provides immunity in *Escherichia coli*. Nucleic Acids Res. Nov. 2011:39(21):9275-82. doi: 10.1093/nar/glu606. Epub Aug. 3, 2011.
SBI. PrecisionX Cas9 SmartNudles vector system user manual. System Biosciences. 2013.
Semenov A, et al. Interference by clustered regularly interspaced short palindromic repeat (CRISPR) RNA is governed by a seed sequence. Proc Natl Acad Sci US A.Jun. 21, 2011:108(25): 10098-103. doi: 10.1073/pnas.1104144108. Epub Jun. 6, 2011.
Sigma-Aldrich. Cas9-GFP Expression Plasmids. Product formation, 2013.

(56) References Cited

OTHER PUBLICATIONS

Sorek, et al. CRISPR—a widespread system that provides acquired resistance against phages in bacteria and archaea. Nat Rev Microbiol. Mar. 2008;6(3):181-6.
Subach, et al. Conversion of red fluorescent protein into a bright blue probe. Chem Biol. Oct. 20, 2008;15(10): 1116-24. doi: 10.1016/j.chembiol.2008.08.006.
Summerton, et al. Morpholino antisense oligomers: design, preparation, and properties.Antisense Nudelc Acid Drug Dev. Jun. 1997;7(3):187-95.
Summerton. Morpholino antisense oligomers: the case for an RNase H-independent structural type. Biochim Biophys Acta, Dec. 10, 1999;1489(1):141-58.
Tahallah, et al. The effect of the source pressure on the abundance of ions of noncovalent protein assemblies in an electrospray ionization orthogonal time-of-flight instrument. Rapid Commun Mass Spectrom. 2001; 15(8):596-601.
Tanaka, et al. Conformational variations in an infectious protein determine prion strain differences. Nature, Mar. 18, 2004;428(6980):323-8.
Tang, et al. Identification of 86 candidates for small non-messenger RNAs from the archaeon Archacoglobus fulgidus. Proc Natl Acad Sci US A. May 28, 2002;99(11 ):7536-41.
Tang, et al. Identification of novel non-coding RNAs as potential antisense regulators in the archaeon Sulfolobus solfataricus. Mol Microbiol. Jan. 2005;56(2):469-8 I.
Terns, et al. CRISPR-based adaptive immune systems. Curr Opin Microbiol. Jun. 2011;34(3):321-7. doi: 10.1016/j.mib.2011.03.005. Epub Apr. 29, 2011.
Urnov, et al. Genome editing with engineered zinc finger nucleases. Nat Rev Genet, Sep. 2010;II(9):636-46. doi: 10.1038/nrg2842.
Van Den Heuvel, et al. Improving the performance of a quadrupole time-of-flight instrument for macromolecular mass spectrometry. Anal Chem. Nov. 1, 2006 ;78(21):7473-83.
Van Der Oost, et al. CRISPR-based adaptive and heritable immunity in prokaryotes. Trends Bio chem Sci. Aug. 2009:34(8):401-7. doi: 10.1016/j.tibs.2009.05.002. Epub Jul. 29, 2009.
Wang, et al. One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.
Westra, et al. Cascade-mediated binding and bending of negatively supercoiled DNA. RNA Biol. Sep. 2012;9(9): 1134-8. doi: 10.4161/ma.21410. Epub Sep. 1, 2012.
Westra, et al. H-NS-mediated repression of CRISPR-based immunity in *Escherichia coli* KI2 can be relieved by the transcription activator LeuO. Mol Microbiol. Sep. 2010;77(6):1380-93. doi: 10.1III/j.1365-2958.2010.07315.x. Epub Aug. 18, 2010.
Wiedenheft, et al. RNA-guided genetic silencing systems in bacteria and archaea, Nature. Feb. 15, 2012,482(7385):331-8. doi: 10.1038/nature10886.
Wiedenheft, et al. Structural basis for DNase activity of a conserved protein implicated in CRISPR-mediated genome defense. Structure. Jun. 10, 2009;17(6):904-12. doi: 10.1016/j.str.2009.03.019.
Xia, et al. Bioluminescence of Aequorea macrodactyla, a common jellyfish species in the East China Sea. Mar Biotechnol (NY). Mar. 2002;4(2):155-62.
Cong et al. (2013) Multiplex Genome Engineering Using CRISPR/Cas Systems. Science, 339:819-823, and supplementary materials.
Mojica et al. (2009) Short motif sequences determine the targets of the prokaryotic CRISPR defence system. Microbiology, 155:733-740, and Supplementary info, 37 pages.
Morton et al. (2006) Induction and repair of zinc-finger nuclease-targeted double-strand breaks in Caenorhabditis elegans somatic cells. PNAS 103(44): 16370-16375, and supplementary materials.
Watters. "In Situ Hybridization", in: Walker et al., Medical Biomethods Handbook (New Jersey, Humana Press, 2005), pp. 409-418.
Caccavo, et al., "Geobacter sulfurreducens sp. nov., a Hydrogen- and Acetate-Oxidizing Dissimilatory Metal-Reducing Microorganism," Applied and Environmental Microbiology 60(10):3752-3759 (1994).
Choudhury, R., et al., "Engineering RNA endonucleases with customized sequence specificities," Nat. Commun. 3:1147 (2012). doi: 10.1038/ncomms2154.
Guilinger, J., et al., "Fusion of catalytically inactive Cas9 to Fokl nuclease improves the specificity of genome modification," Nat Biotechnol. 32(6):577-582 (2014). Epub Apr. 25, 2014. doi: 10.1038/nbt.2909.
Hochstrasser, M., et al., "DNA targeting by a minimal CRISPR RNA-guided Cascade," Mol, Cell. 63(5):840-851 (2016). dol: 10.1016/j.molcel.2016.07.027.
Jackson, R., et al., "Crystal structure of the CRISPR RNA-guided surveillance complex from *Escherichia coli*," Science 345:1473-1479 (2014).
Jinek, M., et al., "A programmable dual-RNA-guided DNA endonuclease in adaptive bacterial immunity," Science 337 (6096):816-821 (2012). Epub Jun. 28, 2012. doi: 10.1126/science.1225829.
Kim, Y.G., et al., "Site-specific cleavage of DNA-RNA hybrids by zinc finger/Fokl cleavage domain fusions," Gene 203(1):43-49 (1997).
Klein, et al., "Design and characterization of structured protein linkers with differing flexibilities," Protein Engineering, Design & Selection 27(10):325-330 (2014).
Methe, et al., "Genome of Geobacter sulfurreducens: Metal Reduction in Subsurface Environments," Science 302:1967-1969 (2003).
NC_002939.5 (Geobacter sulfurreducens PCA chromosome, complete genome, nucleotide positions 72629-74308, priority to Aug. 3, 2016, 2 pages).
NC_002939.4 (Geobacter sulfurreducens PCA chromosome, complete genome, nucleotide positions 72630-74309, priority to Oct. 14, 2010, 2 pages).
NZ_GG657742.1 (Streptomyces sp. SPB78 genomic scaffold supercont 1.1, whole genome shotgun sequence, NCBI Reference Sequence, nucleotide positions 3502816-3507630, priority to Oct. 26, 2010, 3 pages).
Pingoud, et al., "Type II restriction endonucleases—a historical perspective and more," Nucleic Acids Research 42(12):7489-7527 (2014).
Redding, S., et al., "Surveillance and processing of foreign DNA by the *Escherichia coli* CRISPR-Cas system," Cell 163(4):854-865 (2015). doi: 10.1016/j.cell.2015.10.003.
Rittie, et al., "Enzymes used in molecular biology: a useful guide," Journal of Cell Communication and Signaling 2(1):25-45 (2008).
Sashital, D., et al., "Mechanism of foreign DNA selection in a bacterial adaptive immune systern," Mol. Cell 46:606-615 (2012).
Sinkunas, T., et al., "In vitro reconstitution of Cascade-mediated CRISPR immunity in *Streptococcus thermophilus*," EMBO J. 32(3):385-384 (2013). Epub Jan. 18, 2013. doi: 10.1038/emboj.2012.352.
Wiedenheft, B., et al., "Structures of the RNA-guided surveillance complex from a bacterial immune system," Nature 477(7365):486-489 (2011). doi: 10.1038/nature10402.
Zhao, et al., "Increasing the homogeneity, stability and activity of human serum albumin and interferon-alpha2b fusion protein by linker engineering." Protein Expression and Purification, 61:73-77 (2008).
International search report and written opinion dated Jun. 16, 2014 for PCT /US2014/023 828.
Notice of allowance dated Feb. 20, 2014 for U.S. Appl. No. 14/054,414.
Office action dated Jan. 17, 2014 for U.S. Appl. No. 14/054,414.
Office action dated Dec. 5, 2013 for U.S. Appl. No. 14/054,414.

* cited by examiner

FIG. 9

```
            PAM   Seed
wildtype    AAGGATGCCAGTGATAAGTGGAATGCCATGTGGGCTGTCAAAA

mutant 1    AAGGATGCGAGTGATAAGTGGAATGCCATGTGGGCTGTCAAAA
mutant 2    ------------------------GCCATGTGGGCTGTCAAAA
mutant 3    --------------------GAATGCCATGTGGGCTGTCAAAA
mutant 4    -------------------------------------------
```

MODIFIED CASCADE RIBONUCLEOPROTEINS AND USES THEREOF

CROSS-REFERENCE TO RELATED APPLICATIONS

This application is a Continuation of U.S. patent application Ser. No. 17/179,215, filed 18 Feb. 2021, now U.S. Pat. No. 11,939,604 issued 26 Mar. 2024, which is a Continuation of U.S. patent application Ser. No. 16/914,203, filed 26 Jun. 2020, now U.S. Pat. No. 10,954,498 issued 23 Mar. 2021, which is a Continuation of U.S. patent application Ser. No. 16/554,225, filed 28 Aug. 2019, now U.S. Pat. No. 10,711,257, issued 14 Jul. 2020, which is a Continuation of U.S. patent application Ser. No. 15/802,413, filed 2 Nov. 2017, now U.S. Pat. No. 10,435,678, issued 8 Oct. 2019, which is a Continuation of U.S. patent application Ser. No. 14/997,474, filed 15 Jan. 2016, now U.S. Pat. No. 9,885,026, issued 6 Feb. 2018, which is a Continuation of U.S. patent application Ser. No. 14/326,099, filed 8 Jul. 2014, now abandoned, which is a Continuation of U.S. patent application Ser. No. 14/240,735, filed 24 Feb. 2014, now abandoned, which is a National Stage Entry of PCT/EP2012/076674, filed 21 Dec. 2012, now expired, which claims the benefit of priority under 35 U.S.C. 119(a)/(b) of United Kingdom Patent Application No. GB1122458.1, filed 30 Dec. 2011, now abandoned, the contents of all of which are incorporated herein by reference in their entirety. A certified copy of the foreign priority document (GB 1122458.1) is of record in U.S. patent application Ser. No. 14/240,735.

TECHNICAL FIELD

The invention relates to the field of genetic engineering and more particularly to the area of gene and/or genome modification of organisms, including prokaryotes and eukaryotes. The invention also concerns methods of making site specific tools for use in methods of genome analysis and genetic modification, whether in vivo or in vitro. The invention more particularly relates to the field of ribonucleoproteins which recognise and associate with nucleic acid sequences in a sequence specific way.

REFERENCE TO SEQUENCE LISTING, TABLE, OR COMPUTER PROGRAM

The Sequence Listing submitted as file name CBI010.18.xml, created on Jan. 17, 2024, with a file size of 86,047 bytes, is hereby incorporated by reference herein in its entirety.

BACKGROUND

Bacteria and archaea have a wide variety of defense mechanisms against invasive DNA. So called CRISPR/Cas defense systems provide adaptive immunity by integrating plasmid and viral DNA fragments in loci of clustered regularly interspaced short palindromic repeats (CRISPR) on the host chromosome. The viral or plasmid-derived sequences, known as spacers, are separated from each other by repeating host-derived sequences. These repetitive elements are the genetic memory of this immune system and each CRISPR locus contains a diverse repertoire of unique 'spacer' sequences acquired during previous encounters with foreign genetic elements.

Acquisition of foreign DNA is the first step of immunization, but protection requires that the CRISPR is transcribed and that these long transcripts are processed into short CRISPR-derived RNAs (crRNAs) that each contains a unique spacer sequence complementary to a foreign nucleic acid challenger.

In addition to the crRNA, genetic experiments in several organisms have revealed that a unique set of CRISPR-associated (Cas) proteins is required for the steps of acquiring immunity, for crRNA biogenesis and for targeted interference. Also, a subset of Cas proteins from phylogenetically distinct CRISPR systems have been shown to assemble into large complexes that include a crRNA.

A recent re-evaluation of the diversity of CRISPR/Cas systems has resulted in a classification into three distinct types (Makarova K. et al (2011) Nature Reviews Microbiology—AOP 9 May 2011; doi:10.1038/nrmicro2577) that vary in cas gene content, and display major differences throughout the CRISPR defense pathway. (The Makarova classification and nomenclature for CRISPR-associated genes is adopted in the present specification.) RNA transcripts of CRISPR loci (pre-crRNA) are cleaved specifically in the repeat sequences by CRISPR associated (Cas) endoribonucleases in type I and type III systems or by RNase III in type II systems; the generated crRNAs are utilized by a Cas protein complex as a guide RNA to detect complementary sequences of either invading DNA or RNA. Cleavage of target nucleic acids has been demonstrated in vitro for the *Pyrococcus furiosus* type III-B system, which cleaves RNA in a ruler-anchored mechanism, and, more recently, in vivo for the *Streptococcus thermophiles* type II system, which cleaves DNA in the complementary target sequence (protospacer). In contrast, for type I systems the mechanism of CRISPR-interference is still largely unknown.

The model organism *Escherichia coli* strain K12 possesses a CRISPR/Cas type I-E (previously known as CRISPR subtype E (Cse)). It contains eight cas genes (cas1, cas2, cas3 and cse1, cse2, cas7, cas5, cas6e) and a downstream CRISPR (type-2 repeats). In *Escherichia coli* K12 the eight cas genes are encoded upstream of the CRISPR locus. Cas1 and Cas2 do not appear to be needed for target interference, but are likely to participate in new target sequence acquisition. In contrast, six Cas proteins: Cse1, Cse2, Cas3, Cas7, Cas5 and Cas6e (previously also known as CasA, CasB, Cas3, CasC/Cse4, CasD and CasE/Cse3 respectively) are essential for protection against lambda phage challenge. Five of these proteins: Cse1, Cse2, Cas7, Cas5 and Cas6e (previously known as CasA, CasB, CasC/Cse4, CasD and CasE/Cse3 respectively) assemble with a crRNA to form a multi-subunit ribonucleoprotein (RNP) referred to as Cascade.

In *E. coli*, Cascade is a 405 kDa ribonucleoprotein complex composed of an unequal stoichiometry of five functionally essential Cas proteins: $Cse1_1Cse2_2Cas7_6Cas5_1Cas6e_1$ (i.e. under previous nomenclature $CasA_1B_2C_6D_1E_1$) and a 61-nt CRISPR-derived RNA. Cascade is an obligate RNP that relies on the crRNA for complex assembly and stability, and for the identification of invading nucleic acid sequences. Cascade is a surveillance complex that finds and binds foreign nucleic acids that are complementary to the spacer sequence of the crRNA.

Jore et al. (2011) entitled "Structural basis for CRISPR RNA-guided DNA recognition by Cascade" Nature Structural & Molecular Biology 18: 529-537 describes how there is a cleavage of the pre-crRNA transcript by the Cas6e subunit of Cascade, resulting in the mature 61 nt crRNA being retained by the CRISPR complex. The crRNA serves as a guide RNA for sequence specific binding of Cascade to double stranded (ds) DNA molecules through base pairing between the crRNA spacer and the complementary protospacer, forming a so-called R-loop. This is known to be an ATP-independent process.

Brouns S. J. J., et al (2008) entitled "Small CRISPR RNAs guide antiviral defense in prokaryotes" Science 321: 960-964 teaches that Cascade loaded with a crRNA requires Cas3 for in vivo phage resistance.

Marraffini L. & Sontheimer E. (2010) entitled "CRISPR interference: RNA-directed adaptive immunity in bacteria and archaea" Nature Reviews Genetics 11: 181-190 is a review article which summarises the state of knowledge in the art in the field. Some suggestions are made about CRISPR-based applications and technologies, but this is mainly in the area of generating phage resistant strains of domesticated bacteria for the dairy industry. The specific cleavage of RNA molecules in vitro by a crRNP complex in *Pyrococcus furiosus* is suggested as something which awaits further development. Manipulation of CRISPR systems is also suggested as a possible way of reducing transmission of antibiotic-resistant bacterial strains in hospitals. The authors stress that further research effort will be needed to explore the potential utility of the technology in these areas.

US2011236530 A1 (Manoury et al.) entitled "Genetic cluster of strains of *Streptococcus thermophilus* having unique rheological properties for dairy fermentation" discloses certain *S. thermophilus* strains which ferment milk so that it is highly viscous and weakly ropy. A specific CRISPR locus of defined sequence is disclosed.

US2011217739 A1 (Terns et al.) entitled "Cas6 polypeptides and methods of use" discloses polypeptides which have Cas6 endoribonuclease activity. The polypeptides cleave a target RNA polynucleotide having a Cas6 recognition domain and cleavage site. Cleavage may be carried out in vitro or in vivo. Microbes such as *E. coli* or *Haloferax volcanii* are genetically modified so as to express-Cas6 endoribonuclease activity.

WO2010054154 (Danisco) entitled "Bifidobacteria CRISPR sequences" discloses various CRISPR sequences found in Bifidobacteria and their use in making genetically altered strains of the bacteria which are altered in their phage resistance characteristics.

US2011189776 A1 (Terns et al.) entitled "Prokaryotic RNAi-like system and methods of use" describes methods of inactivating target polynucleotides in vitro or in prokaryotic microbes in vivo. The methods use a psiRNA having a 5' region of 5-10 nucleotides chosen from a repeat from a CRISPR locus immediately upstream of a spacer. The 3' region is substantially complementary to a portion of the target polynucleotide. Also described are polypeptides having endonuclease activity in the presence of psiRNA and target polynucleotide.

EP2341149 A1 (Danisco) entitled "Use of CRISPR associated genes (CAS) describes how one or more Cas genes can be used for modulating resistance of bacterial cells against bacteriophage; particularly bacteria which provide a starter culture or probiotic culture in dairy products.

WO2010075424 (The Regents of the University of California) entitled "Compositions and methods for downregulating prokaryotic genes" discloses an isolated polynucleotide comprising a CRISPR array. At least one spacer of the CRISPR is complementary to a gene of a prokaryote so that is can down-regulate expression of the gene; particularly where the gene is associated with biofuel production.

WO2008108989 (Danisco) entitled "Cultures with improved phage resistance" discloses selecting bacteriophage resistant strains of bacteria and also selecting the strains which have an additional spacer having 100% identity with a region of phage RNA. Improved strain combinations and starter culture rotations are described for use in the dairy industry. Certain phages are described for use as biocontrol agents.

WO2009115861 (Institut Pasteur) entitled "Molecular typing and subtyping of *Salmonella* by identification of the variable nucleotide sequences of the CRISPR loci" discloses methods for detecting and identifying bacterial of the *Salmonella* genus by using their variable nucleotide sequences contained in CRISPR loci.

WO2006073445 (Danisco) entitled "Detection and typing of bacterial strains" describes detecting and typing of bacterial strains in food products, dietary supplements and environmental samples. Strains of *Lactobacillus* are identified through specific CRISPR nucleotide sequences.

Urnov F et al. (2010) entitled "Genome editing with engineered zinc finger nucleases" Nature 11: 636-646 is a review article about zinc finger nucleases and how they have been instrumental in the field of reverse genetics in a range of model organisms. Zinc finger nucleases have been developed so that precisely targeting genome cleavage is possible followed by gene modification in the subsequent repair process. However, zinc finger nucleases are generated by fusing a number of zinc finger DNA-binding domains to a DNA cleavage domain. DNA sequence specificity is achieved by coupling several zinc fingers in series, each recognising a three nucleotide motif. A significant drawback with the technology is that new zinc fingers need to be developed for each new DNA locus which requires to be cleaved. This requires protein engineering and extensive screening to ensure specificity of DNA binding.

In the fields of genetic engineering and genomic research there is an ongoing need for improved agents for sequence/site specific nucleic acid detection and/or cleavage.

DETAILED DESCRIPTION

The inventors have made a surprising discovery in that certain bacteria expressing Cas3, which has helicase-nuclease activity, express Cas3 as a fusion with Cse1. The inventors have also unexpectedly been able to produce artificial fusions of Cse1 with other nuclease enzymes.

The inventors have also discovered that Cas3-independent target DNA recognition by Cascade marks DNA for cleavage by Cas3, and that Cascade DNA binding is governed by topological requirements of the target DNA.

The inventors have further found that Cascade is unable to bind relaxed target plasmids, but surprisingly Cascade displays high affinity for targets which have a negatively supercoiled (nSC) topology.

Accordingly in a first aspect the present invention provides a clustered regularly interspaced short palindromic repeat (CRISPR)-associated complex for antiviral defence (Cascade), the Cascade protein complex, or portion thereof, comprising at least CRISPR-associated protein subunits:

Cas7 (or COG 1857) having an amino acid sequence of SEQ ID NO:3 or a sequence of at least 18% identity therewith, Cas5 (or COG1688) having an amino acid sequence of SEQ ID NO:4 or a sequence of at least 17% identity therewith, and Cas6 (or COG 1583) having an amino acid sequence of SEQ ID NO:5 or a sequence of at least 16% identity therewith;

and wherein at least one of the subunits includes an additional amino acid sequence providing nucleic acid or chromatin modifying, visualising, transcription activating or transcription repressing activity.

A subunit which includes an additional amino acid sequence having nucleic acid or chromatin modifying, visualising, transcription activating or transcription repressing activity is an example of what may be termed "a subunit linked to at least one functional moiety"; a functional moiety being the polypeptide or protein made up of the additional amino acid sequence. The transcription activating activity may be that leading to activation or upregulation of a desired genes; the transcription repressing activity leading to repressing or downregulation of a desired genes. The selection of the gene being due to the targeting of the cascade complex of the invention with an RNA molecule, as described further below.

The additional amino acid sequence having nucleic acid or chromatin modifying, visualising, transcription activating or transcription repressing activity is preferably formed of contiguous amino acid residues. These additional amino acids may be viewed as a polypeptide or protein which is contiguous and forms part of the Cas or Cse subunit(s) concerned. Such a polypeptide or protein sequence is preferably not normally part of any Cas or Cse subunit amino acid sequence. In other words, the additional amino acid sequence having nucleic acid or chromatin modifying, visualising, transcription activating or transcription repressing activity may be other than a Cas or Cse subunit amino acid sequence, or portion thereof, i.e. may be other than a Cas3 submit amino acid sequence or portion thereof.

The additional amino acid sequence with nucleic acid or chromatin modifying, visualising, transcription activating or transcription repressing activity may, as desired, be obtained or derived from the same organism, e.g. *E. coli*, as the Cas or Cse subunit(s).

Additionally and/or alternatively to the above, the additional amino acid sequence having nucleic acid or chromatin modifying, visualising, transcription activating or transcription repressing activity may be "heterologous" to the amino acid sequence of the Cas or Cse subunit(s). Therefore, the additional amino acid sequence may be obtained or derived from an organism different from the organism from which the Cas and/or Cse subunit(s) are derived or originate.

Throughout, sequence identity may be determined by way of BLAST and subsequent Cobalt multiple sequence alignment at the National Center for Biotechnology Information webserver, where the sequence in question is compared to a reference sequence (e.g. SEQ ID NO: 3, 4 or 5). The amino acid sequences may be defined in terms of percentage sequence similarity based on a BLOSUM62 matrix or percentage identity with a given reference sequence (e.g. SEQ ID NO:3, 4 or 5). The similarity or identity of a sequence involves an initial step of making the best alignment before calculating the percentage conservation with the reference and reflects a measure of evolutionary relationship of sequences.

Cas7 may have a sequence similarity of at least 31% with SEQ ID NO:3; Cas5 may have a sequence similarity of at least 26% with SEQ ID NO:4. Cas6 may have a sequence similarity of at least 27% with SEQ ID NO:5.

For Cse1/CasA (502 AA):
>gi|16130667|ref|NP_417240.1|CRISP RNA (crRNA) containing Cascade antiviral complex protein [*Escherichia coli* str. K-12 substr. MG1655]

[SEQ ID NO: 1]

MNLLIDNWIPVRPRNGGKVQIINLQSLYCSRDQWRLSLPRDDMELAALAL
LVCIGQIIAPAKDDVEFRHRIMNPLTEDEFQQLIAPWIDMFYLNHAEHPF
MQTKGVKANDVTPMEKLLAGVSGATNCAFVNQPGQGEALCGGCTAIALFN
QANQAPGFGGGFKSGLRGGTPVTTFVRGIDLRSTVLLNVLTLPRLQKQFP
NESHTENQPTWIKPIKSNESIPASSIGFVRGLFWQPAHIELCDPIGIGKC
SCCGQESNLRYTGFLKEKFTFTVNGLWPHPHSPCLVTVKKGEVEEKFLAF
TTSAPSWTQISRVVVDKIIQNENGNRVAAVVNQFRNIAPQSPLELIMGGY
RNNQASILERRHDVLMFNQGWQQYGNVINEIVTVGLGYKTALRKALYTFA
EGFKNKDFKGAGVSVHETAERHFYRQSELLIPDVLANVNFSQADEVIADL
RDKLHQLCEMLFNQSVAPYAHHPKLISTLALARATLYKHLRELKPQGGPS
NG

For Cse2/CasB (160 AA):
>gi|16130666|ref|NP_417239.1|CRISP RNA (crRNA) containing Cascade antiviral complex protein [*Escherichia coli* str. K-12 substr. MG1655]

[SEQ ID NO: 2]

MADEIDAMALYRAWQQLDNGSCAQIRRVSEPDELRDIPAFYRLVQPFGWE
NPRHQQALLRMVFCLSAGKNVIRHQDKKSEQTTGISLGRALANSGRINER
RIFQLIRADRTADMVQLRRLLTHAEPVLDWPLMARMLTWWGKRERQQLLE
DFVLTTNKNA

For Cas7/CasC/Cse4 (363 AA):
>gi|16130665|ref|NP_417238.1|CRISP RNA (crRNA) containing Cascade antiviral complex protein [*Escherichia coli* str. K-12 substr. MG1655]

[SEQ ID NO: 3]

MSNFINIHVLISHSPSCLNRDDMNMQKDAIFGGKRRVRISSQSLKRAMRK
SGYYAQNIGESSLRTIHLAQLRDVLRQKLGERFDQKIIDKTLALLSGKSV
DEAEKISADAVTPWVVGEIAWFCEQVAKAEADNLDDKKLLKVLKEDIAAI
RVNLQQGVDIALSGRMATSGMMTELGKVDGAMSIAHAITTHQVDSDIDWF
TAVDDLQEQGSAHLGTQEFSSGVFYRYANINLAQLQENLGGASREQALEI
ATHVVHMLATEVPGAKQRTYAAFNPADMVMVNFSDMPLSMANAFEKAVKA
KDGFLQPSIQAFNQYWDRVANGYGLNGAAAQFSLSDVDPITAQVKQMPTL
EQLKSWVRNNGEA

For Cas5/CasD (224 AA):
>gi|90111483|ref|NP_417237.2|CRISP RNA (crRNA) containing Cascade antiviral complex protein [*Escherichia coli* str. K-12 substr. MG1655]

[SEQ ID NO: 4]

MRSYLILRLAGPMQAWGQPTFEGTRPTGRFPTRSGLLGLLGACLGIQRDD
TSSLQALSESVQFAVRCDELILDDRRVSVTGLRDYHTVLGAREDYRGLKS
HETIQTWREYLCDASFTVALWLTPHATMVISELEKAVLKPRYTPYLGRRS
CPLTHPLFLGTCQASDPQKALLNYEPVGGDIYSEESVTGHHLKFTARDEP
MITLPRQFASREWYVIKGGMDVSQ

-continued

```
For Cas6e/CasE (199 AA):
>gi|16130663|ref|NP_417236.1|CRISPR RNA
precursor cleavage enzyme; CRISP RNA
(crRNA) containing Cascade antiviral
complex protein [Escherichia coli str.
K-12 substr. MG1655]
                                    [SEQ ID NO: 5]
MYLSKVIIARAWSRDLYQLHQGLWHLFPNRPDAARDFLFHVEKRNTPEGC

HVLLQSAQMPVSTAVATVIKTKQVEFQLQVGVPLYFRLRANPIKTILDNQ

KRLDSKGNIKRCRVPLIKEAEQIAWLQRKLGNAARVEDVHPISERPQYFS

GDGKSGKIQTVCFEGVLTINDAPALIDLVQQGIGPAKSMGCGLLSLAPL
```

In defining the range of sequence variants which fall within the scope of the invention, for the avoidance of doubt, the following are each optional limits on the extent of variation, to be applied for each of SEQ ID NO:1, 2, 3, 4 or 5 starting from the respect broadest range of variants as specified in terms of the respective percentage identity above. The range of variants therefore may therefore include: at least 16%, or at least 17%, or at least 18%, or at least 19%, or at least 20%, or at least 21%, or at least 22%, or at least 23%, or at least 24%, or at least 25%, or at least 26%, or at least 27%, or at least 28%, or at least 29%, or at least 30%, or at least 31%, or at least 32%, or at least 33%, or at least 34%, or at least 35%, or at least 36%, or at least 37%, or at least 38%, or at least 39%, or at least 40%, or at least 41%, or at least 42%, or at least 43%, at least 44%, or at least 45%, or at least 46%, or at least 47%, or at least 48%, or at least 49%, or at least 50%, or at least 51%, or at least 52%, or at least 53%, or at least 54%, or at least 55%, or at least 56%, or at least 57%, or at least 58%, or at least 59%, or at least 60%, or at least 61%, or at least 62%, or at least 63%, or at least 64%, or at least 65%, or at least 66%, or at least 67%, or at least 68%, or at least 69%, or at least 70%, or at least 71%, at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or 100% amino acid sequence identity.

Throughout, the Makarova et al. (2011) nomenclature is being used in the definition of the Cas protein subunits. Table 2 on page 5 of the Makarova et al. article lists the Cas genes and the names of the families and superfamilies to which they belong. Throughout, reference to a Cas protein or Cse protein subunit includes cross reference to the family or superfamily of which these subunits form part.

Throughout, the reference sequences of the Cas and Cse subunits of the invention may be defined as a nucleotide sequence encoding the amino acid sequence. For example, the amino acid sequence of SEQ ID NO:3 for Cas7 also includes all nucleic acid sequences which encode that amino acid sequence. The variants of Cas7 included within the scope of the invention therefore include nucleotide sequences of at least the defined amino acid percentage identities or similarities with the reference nucleic acid sequence; as well as all possible percentage identities or similarities between that lower limit and 100%.

The Cascade complexes of the invention may be made up of subunits derived or modified from more than one different bacterial or archaeal prokaryote. Also, the subunits from different Cas subtypes may be mixed.

In a preferred aspect, the Cas6 subunit is a Cas6e subunit of SEQ ID NO: 17 below, or a sequence of at least 16% identity therewith.

The sequence of a preferred Cas6e subunit is >gi|16130663|ref|NP_417236.1| CRISPR RNA precursor cleavage enzyme; CRISP RNA (crRNA) containing Cascade antiviral complex protein [*Escherichia coli* str. K-12 substr. MG1655]:

```
                                    [SEQ ID NO: 17]
MYLSKVIIARAWSRDLYQLHQGLWHLFPNRPDAARDFLFHVEKRNTPEGC

HVLLQSAQMPVSTAVATVIKTKQVEFQLQVGVPLYFRLRANPIKTILDNQ

KRLDSKGNIKRCRVPLIKEAEQIAWLQRKLGNAARVEDVHPISERPQYFS

GDGKSGKIQTVCFEGVLTINDAPALIDLVQQGIGPAKSMGCGLLSLAPL
```

The Cascade complexes, or portions thereof, of the invention—which comprise at least one subunit which includes an additional amino acid sequence having nucleic acid or chromatin modifying, visualising, transcription activating or transcription repressing activity—may further comprise a Cse2 (or YgcK-like) subunit having an amino acid sequence of SEQ ID NO:2 or a sequence of at least 20% identity therewith, or a portion thereof. Alternatively, the Cse subunit is defined as having at least 38% similarity with SEQ ID NO:2. Optionally, within the protein complex of the invention it is the Cse2 subunit which includes the additional amino acid sequence having nucleic acid or chromatin modifying activity.

Additionally or alternatively, the Cascade complexes of the invention may further comprise a Cse1 (or YgcL-like) subunit having an amino acid sequence of SEQ ID NO: 1 or a sequence of at least 9% identity therewith, or a portion thereof. Optionally within the protein complex of the invention it is the Cse1 subunit which includes the additional amino acid sequence having nucleic acid or chromatin modifying, visualising, transcription activating or transcription repressing activity.

In preferred embodiments, a Cascade complex of the invention is a Type I CRISPR-Cas system protein complex; more preferably a subtype I-E CRISPR-Cas protein complex or it can be based on a Type I-A or Type I-B complex. A Type I-C, D or F complex is possible. In particularly preferred embodiments based on the *E. coli* system, the subunits may have the following stoichiometries: $Cse1_1Cse2_2Cas7_6Cas5_1Cas6_1$ or $Cse1_1Cse2_2Cas7_6Cas5_1Cas6e_1$.

The additional amino acid sequence having nucleic acid or chromatin modifying, visualising, transcription activating or transcription repressing activity may be translationally fused through expression in natural or artificial protein expression systems, or covalently linked by a chemical synthesis step to the at least one subunit; preferably the at least one functional moiety is fused or linked to at least the region of the N terminus and/or the region of the C terminus of at least one of a Cse1, Cse2, Cas7, Cas5, Cas6 or Cas6e subunit. In particularly preferred embodiments, the additional amino acid sequence having nucleic acid or chromatin modifying activity is fused or linked to the N terminus or the C terminus of a Cse1, a Cse2 or a Cas5 subunit; more preferably the linkage is in the region of the N terminus of a Cse1 subunit, the N terminus of a Cse2 subunit, or the N terminus of a Cas7 subunit.

The additional amino acid sequence having nucleic acid or chromatin modifying, activating, repressing or visualising activity may be a protein; optionally selected from a helicase, a nuclease, a nuclease-helicase, a DNA methyltransferase (e.g. Dam), or DNA demethylase, a histone methyltransferase, a histone demethylase, an acetylase, a deacetylase, a phosphatase, a kinase, a transcription (co-) activator, an RNA polymerase submit, a transcription repressor, a DNA binding protein, a DNA structuring protein, a marker protein, a reporter protein, a fluorescent protein, a ligand binding protein (e.g. mCherry or a heavy metal binding protein), a signal peptide (e.g. Tat-signal sequence), a subcellular localisation sequence (e.g. nuclear localisation sequence) or an antibody epitope.

The protein concerned may be a heterologous protein from a species other than the bacterial species from which the Cascade protein subunits have their sequence origin.

When the protein is a nuclease, it may be one selected from a type II restriction endonuclease such as FokI, or a mutant or an active portion thereof. Other type II restriction endonucleases which may be used include EcoR1, EcoRV, BglI, BamHI, BsgI and BspMI. Preferably, one protein complex of the invention may be fused to the N terminal domain of FokI and another protein complex of the invention may be fused to the C terminal domain of FokI. These two protein complexes may then be used together to achieve an advantageous locus specific double stranded cut in a nucleic acid, whereby the location of the cut in the genetic material is at the design and choice of the user, as guided by the RNA component (defined and described below) and due to presence of a so-called "protospacer adjacent motif" (PAM) sequence in the target nucleic acid strand (also described in more detail below).

In a preferred embodiment, a protein complex of the invention has an additional amino acid sequence which is a modified restriction endonuclease, e.g. FokI. The modification is preferably in the catalytic domain. In preferred embodiments, the modified FokI is KKR Sharkey or ELD Sharkey which is fused to the Cse1 protein of the protein complex. In a preferred application of these complexes of the invention, two of these complexes (KKR Sharkey and ELD Sharkey) may be together in combination. A heterodimer pair of protein complexes employing differently modified FokI is has particular advantage in targeted double stranded cutting of nucleic acid. If homodimers are used then it is possible that there is more cleavage at non-target sites due to non-specific activity. A heterodimer approach advantageously increases the fidelity of the cleavage in a sample of material.

The Cascade complex with additional amino acid sequence having nucleic acid or chromatin modifying, visualising, transcription activating or transcription repressing activity defined and described above is a component part of an overall system of the invention which advantageously permits the user to select in a predetermined matter a precise genetic locus which is desired to be cleaved, tagged or otherwise altered in some way, e.g methylation, using any of the nucleic acid or chromatin modifying, visualising, transcription activating or transcription repressing entities defined herein. The other component part of the system is an RNA molecule which acts as a guide for directing the Cascade complex of the invention to the correct locus on DNA or RNA intending to be modified, cut or tagged.

The Cascade complex of the invention preferably also comprises an RNA molecule which comprises a ribonucleotide sequence of at least 50% identity to a desired target nucleic acid sequence, and wherein the protein complex and the RNA molecule form a ribonucleoprotein complex. Preferably the ribonucleoprotein complex forms when the RNA molecule is hybridized to its intended target nucleic acid sequence. The ribonucleoprotein complex forms when the necessary components of Cascade-functional moiety combination and RNA molecule and nucleic acid (DNA or RNA) are present together in suitable physiological conditions, whether in vivo or in vitro. Without wishing to be bound by any particular theory, the inventors believe that in the context of dsDNA, particularly negatively supercoiled DNA, the Cascade complex associating with the dsDNA causes a partial unwinding of the duplex strands which then allows the RNA to associate with one strand; the whole ribonucleoprotein complex then migrates along the DNA strand until a target sequence substantially complementary to at least a portion of the RNA sequence is reached, at which point a stable interaction between RNA and DNA strand occurs, and the function of the functional moiety takes effect, whether by modifying, nuclease cutting or tagging of the DNA at that locus.

In preferred embodiments, a portion of the RNA molecule has at least 50% identity to the target nucleic acid sequence; more preferably at least 95% identity to the target sequence. In more preferred embodiments, the portion of the RNA molecule is substantially complementary along its length to the target DNA sequence; i.e. there is only one, two, three, four or five mismatches which may be contiguous or non-contiguous. The RNA molecule (or portion thereof) may have at least 51%, or at least 52%, or at least 53%, or at least 54%, or at least 55%, or at least 56%, or at least 57%, or at least 58%, or at least 59%, or at least 60%, or at least 61%, or at least 62%, or at least 63%, or at least 64%, or least 65%, or at least 66%, or at least 67%, or at least 68%, or at least 69%, or at least 70%, or at least 71%, or at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99° %, or 100% identity to the target sequence.

The target nucleic acid may be DNA (ss or ds) or RNA.

In other preferred embodiments, the RNA molecule or portion thereof has at least 70% identity with the target nucleic acid. At such levels of identity, the target nucleic acid is preferably dsDNA.

The RNA molecule will preferably require a high specificity and affinity for the target nucleic acid sequence. A dissociation constant ($K_d$) in the range 1 pM to 1 μM, preferably 1-100 nM is desirable as determined by preferably native gel electrophoresis, or alternatively isothermal titration calorimetry, surface plasmon resonance, or fluorescence based titration methods. Affinity may be determined using an electrophoretic mobility shift assay (EMSA), also called gel retardation assay (see Semenova E et al. (2011) Proc. Natl. Acad. Sci. USA 108: 10098-10103).

The RNA molecule is preferably modelled on what are known from nature in prokaryotes as CRISPR RNA (crRNA) molecules. The structure of crRNA molecules is already established and explained in more detail in Jore et al. (2011) Nature Structural & Molecular Biology 18: 529-537. In brief, a mature crRNA of type I-E is often 61 nucleotides long and consists of a 5' "handle" region of 8 nucleotides, the "spacer" sequence of 32 nucleotides, and a 3' sequence of 21 nucleotides which form a hairpin with a tetranucleotide loop. However, the RNA used in the invention does not have to be designed strictly to the design of naturally occurring crRNA, whether in length, regions or specific RNA sequences. What is clear though, is that RNA molecules for use in the invention may be designed based on gene sequence information in the public databases or newly discovered, and then made artificially, e.g. by chemical synthesis in whole or in part. The RNA molecules of the invention may also be designed and produced by way of expression in genetically modified cells or cell free expression systems and this option may include synthesis of some or all of the RNA sequence.

The structure and requirements of crRNA has also been described in Semenova E et al. (2011) Proc. Natl. Acad. Sci. USA 108: 10098-10103. There is a so-called "SEED" portion forming the 5' end of the spacer sequence and which is flanked 5' thereto by the 5' handle of 8 nucleotides. Semenova et al. (2011) have found that all residues of the SEED sequence should be complementary to the target sequence, although for the residue at position 6, a mismatch may be tolerated. Similarly, when designing and making an RNA component of a ribonucleoprotein complex of the invention directed at a target locus (i.e. sequence), the necessary match and mismatch rules for the SEED sequence can be applied.

The invention therefore includes a method of detecting and/or locating a single base change in a target nucleic acid molecule comprising contacting a nucleic acid sample with a ribonucleoprotein complex of the invention as hereinbefore described, or with a Cascade complex and separate RNA component of the invention as hereinbefore described, and wherein the sequence of the RNA component (including when in the ribonucleoprotein complex) is such that it discriminates between a normal allele and a mutant allele by virtue of a single base change at position 6 of a contiguous sequence of 8 nucleotide residues.

In embodiments of the invention, the RNA molecule may have a length in the range of 35-75 residues. In preferred embodiments, the portion of the RNA which is complementary to and used for targeting a desired nucleic acid sequence is 32 or 33 residues long. (In the context of a naturally occurring crRNA, this would correspond to the spacer portion; as shown in FIG. 1 of Semenova et al. (2011)).

A ribonucleoprotein complex of the invention may additionally have an RNA component comprising 8 residues 5' to the RNA sequence which has at least substantial complementarity to the nucleic acid target sequence. (The RNA sequence having at least substantial complementarity to the nucleic acid target sequence would be understood to correspond in the context of a crRNA as being the spacer sequence. The 5' flanking sequence of the RNA would be considered to correspond to the 5' handle of a crRNA. This is shown in FIG. 1 of Semenova et al. (2011)).

A ribonucleoprotein complex of the invention may have a hairpin and tetranucleotide loop forming sequence 3' to the RNA sequence which has at least substantial complementarity to the DNA target sequence. (In the context of crRNA, this would correspond to a 3' handle flanking the spacer sequence as shown in FIG. 1 of Semenova et al. (2011)).

In some embodiments, the RNA may be a CRISPR RNA (crRNA).

The Cascade proteins and complexes of the invention may be characterised in vitro in terms of its activity of association with the RNA guiding component to form a ribonucleoprotein complex in the presence of the target nucleic acid (which may be DNA or RNA). An electrophoretic mobility shift assay (EMSA) may be used as a functional assay for interaction of complexes of the invention with their nucleic acid targets. Basically, Cascade-functional moiety complex of the invention is mixed with nucleic acid targets and the stable interaction of the Cascade-functional moiety complex is monitored by EMSA or by specific readout out the functional moiety, for example endonucleolytic cleavage of target DNA at the desired site. This can be determined by further restriction fragment length analysis using commercially available enzymes with known specificities and cleavage sites in a target DNA molecule.

Visualisation of binding of Cascade proteins or complexes of the invention to DNA or RNA in the presence of guiding RNA may be achieved using scanning/atomic force microscopy (SFM/AFM) imaging and this may provide an assay for the presence of functional complexes of the invention.

The invention also provides a nucleic acid molecule encoding at least one clustered regularly interspaced short palindromic repeat (CRISPR)-associated protein subunit selected from:

a. a Cse1 subunit having an amino acid sequence of SEQ ID NO: 1 or a sequence of at least 9% identity therewith;
b. a Cse2 subunit having an amino acid sequence of SEQ ID NO:2 or a sequence of at least 20% identity therewith;
c. a Cas7 subunit having an amino acid sequence of SEQ ID NO:3 or a sequence of at least 18% identity therewith;
d. a Cas5 subunit having an amino acid sequence of SEQ ID NO:4 or a sequence of at least 17% identity therewith;
e. a Cas6 subunit having an amino acid sequence of SEQ ID NO:5 or a sequence of at least 16% identity therewith; and wherein at least a, b, c, d or e includes an additional amino acid sequence having nucleic acid or chromatin modifying, visualising, transcription activating or transcription repressing activity.

The additional amino acid sequence having nucleic acid or chromatin modifying, visualising, transcription activating or transcription repressing activity is preferably fused to the CRISPR-associated protein subunit.

In the nucleic acids of the invention defined above, the nucleotide sequence may be that which encodes the respective SEQ ID NO: 1, SEQ ID NO:2, SEQ ID NO:3, SEQ ID NO:4 or SEQ ID NO:5, or in defining the range of variant sequences thereto, it may be a sequence hybridisable to that nucleotide sequence, preferably under stringent conditions, more preferably very high stringency conditions. A variety of stringent hybridisation conditions will be familiar to the skilled reader in the field. Hybridization of a nucleic acid molecule occurs when two complementary nucleic acid molecules undergo an amount of hydrogen bonding to each other known as Watson-Crick base pairing. The stringency of hybridization can vary according to the environmental (i.e. chemical/physical/biological) conditions surrounding the nucleic acids, temperature, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, NY, 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)

| | |
|---|---|
| Hybridization: | 5x SSC at 65 °C for 16 hours |
| Wash twice: | 2x SSC at room temperature (RT) for 15 minutes each |
| Wash twice: | 0.5x SSC at 65 °C for 20 minutes each |

High Stringency (Allows Sequences that Share at Least 80% Identity to Hybridize)

| | |
|---|---|
| Hybridization: | 5x-6x SSC at 65 °C-70 °C for 16-20 hours |
| Wash twice: | 2x SSC at RT for 5-20 minutes each |
| Wash twice: | 1x SSC at 55 °C-70 °C for 30 minutes each |

Low Stringency (Allows Sequences that Share at Least 50% Identity to Hybridize)

| | |
|---|---|
| Hybridization: | 6x SSC at RT to 55 °C for 16-20 hours |
| Wash at least twice: | 2x-3x SSC at RT to 55 °C for 20-30 minutes each. |

The nucleic acid molecule may be an isolated nucleic acid molecule and may be an RNA or a DNA molecule.

The additional amino acid sequence may be selected from a helicase, a nuclease, a nuclease-helicase (e.g. Cas3), a DNA methyltransferase (e.g. Dam), a DNA demethylase, a histone methyltransferase, a histone demethylase, an acetylase, a deacetylase, a phosphatase, a kinase, a transcription (co-)activator, an RNA polymerase subunit, a transcription repressor, a DNA binding protein, a DNA structuring protein, a marker protein, a reporter protein, a fluorescent protein, a ligand binding protein (e.g. mCherry or a heavy metal binding protein), a signal peptide (e.g. Tat-signal sequence), a subcellular localisation sequence (e.g. nuclear localisation sequence), or an antibody epitope. The additional amino acid sequence may be, or from a different protein from the organism from which the relevant Cascade protein subunit(s) are derived.

The invention includes an expression vector comprising a nucleic acid molecule as hereinbefore defined. One expression vector may contain the nucleotide sequence encoding a single Cascade protein subunit and also the nucleotide sequence encoding the additional amino acid sequence, whereby on expression the subunit and additional sequence are fused. Other expression vectors may comprise nucleotide sequences encoding just one or more Cascade protein subunits which are not fused to any additional amino acid sequence.

The additional amino acid sequence with nucleic acid or chromatin modifying activity may be fused to any of the Cascade subunits via a linker polypeptide. The linker may be of any length up to about 60 or up to about 100 amino acid residues. Preferably the linker has a number of amino acids in the range 10 to 60, more preferably 10-20. The amino acids are preferably polar and/or small and/or charged amino acids (e.g. Gln, Ser, Thr, Pro, Ala, Glu, Asp, Lys, Arg, His, Asn, Cys, Tyr). The linker peptide is preferably designed to obtain the correct spacing and positioning of the fused functional moiety and the subunit of Cascade to which the moiety is fused to allow proper interaction with the target nucleotide.

An expression vector of the invention (with or without nucleotide sequence encoding amino acid residues which on expression will be fused to a Cascade protein subunit) may further comprise a sequence encoding an RNA molecule as hereinbefore defined. Consequently, such expression vectors can be used in an appropriate host to generate a ribonucleoprotein of the invention which can target a desired nucleotide sequence.

Accordingly, the invention also provides a method of modifying, visualising, or activating or repressing transcription of a target nucleic acid comprising contacting the nucleic acid with a ribonucleoprotein complex as hereinbefore defined. The modifying may be by cleaving the nucleic acid or binding to it.

The invention also includes a method of modifying, visualising, or activating or repressing transcription of a target nucleic acid comprising contacting the nucleic acid with a Cascade protein complex as hereinbefore defined, plus an RNA molecule as hereinbefore defined.

In accordance with the above methods, the modification, visualising, or activating or repressing transcription of a target nucleic acid may therefore be carried out in vitro and in a cell free environment; i.e. the method is carried out as a biochemical reaction whether free in solution or whether involving a solid phase. Target nucleic acid may be bound to a solid phase, for example.

In a cell free environment, the order of adding each of the target nucleic acid, the Cascade protein complex and the RNA molecule is at the option of the average skilled person. The three components may be added simultaneously, sequentially in any desired order, or separately at different times and in a desired order. Thus it is possible for the target nucleic acid and RNA to be added simultaneously to a reaction mix and then the Cascade protein complex of the invention to be added separately and later in a sequence of specific method steps.

The modification, visualising, or activating or repressing transcription of a target nucleic acid may be made in situ in a cell, whether an isolated cell or as part of a multicellular tissue, organ or organism. Therefore in the context of whole tissue and organs, and in the context of an organism, the method can be carried out in vivo or it can be carried out by isolating a cell from the whole tissue, organ or organism and then returning the cell treated with ribonucleoprotein complex to its former location, or a different location, whether within the same or a different organism. Thus the method would include allografts, autografts, isografts and xenografts.

In these embodiments, the ribonucleoprotein complex or the Cascade protein complex of the invention requires an appropriate form of delivery into the cell, which will be well known to persons of skill in the art, including microinjection, whether into the cell cytoplasm or into the nucleus.

Also when present separately, the RNA molecule requires an appropriate form of delivery into a cell, whether simultaneously, separately or sequentially with the Cascade protein complex. Such forms of introducing RNA into cells are well known to a person of skill in the art and may include in vitro or ex vivo delivery via conventional transfection methods. Physical methods, such as microinjection and electroporation, as well as calcium co-precipitation, and commercially available cationic polymers and lipids, and cell-penetrating peptides, cell-penetrating particles (gene-gun) may each be used. For example, viruses may be used as delivery vehicles, whether to the cytoplasm and/or nucleus—e.g. via the (reversible) fusion of Cascade protein complex of the invention or a ribonucleoprotein complex of the invention to the viral particle. Viral delivery (e.g. adenovirus delivery) or *Agrobacterium*-mediated delivery may be used.

The invention also includes a method of modifying visualising, or activating or repressing transcription of a target nucleic acid in a cell, comprising transfecting, transforming or transducing the cell with any of the expression vectors as hereinbefore described. The methods of transfection, transformation or transduction are of the types well known to a person of skill in the art. Where there is one expression vector used to generate expression of a Cascade complex of the invention and when the RNA is added directly to the cell then the same or a different method of transfection, transformation or transduction may be used. Similarly, when there is one expression vector being used to generate expression of a Cascade-functional fusion complex of the invention and when another expression vector is being used to generate the RNA in situ via expression, then the same or a different method of transfection, transformation or transduction may be used.

In other embodiments, mRNA encoding the Cascade complex of the invention is introduced into a cell so that the Cascade complex is expressed in the cell. The RNA which guides the Cascade complex to the desired target sequence is also introduced into the cell, whether simultaneously, separately or sequentially from the mRNA, such that the necessary ribonucleoprotein complex is formed in the cell.

In the aforementioned methods of modifying or visualising a target nucleic acid, the additional amino acid sequence may be a marker and the marker associates with the target nucleic acid; preferably wherein the marker is a protein; optionally a fluorescent protein, e.g. green fluorescent protein (GFP) or yellow fluorescent protein (YFP) or mCherry. Whether in vitro, ex vivo or in vitro, then methods of the invention can be used to directly visualise a target locus in a nucleic acid molecule, preferably in the form of a higher order structure such as a supercoiled plasmid or chromosome, or a single stranded target nucleic acid such as mRNA. Direct visualisation of a target locus may use electron micrography, or fluorescence microscopy.

Other kinds of label may be used to mark the target nucleic acid including organic dye molecules, radiolabels and spin labels which may be small molecules.

In methods of the invention described above, the target nucleic acid is DNA; preferably dsDNA although the target can be RNA; preferably mRNA.

In methods of the invention for modifying, visualising, activating transcription or repressing transcription of a target nucleic acid wherein the target nucleic acid is dsDNA, the additional amino acid sequence with nucleic acid or chromatin modifying activity may be a nuclease or a helicase-nuclease, and the modification is preferably a single stranded or a double stranded break at a desired locus. In this way unique sequence specific cutting of DNA can be engineered by using the Cascade-functional moiety complexes. The chosen sequence of the RNA component of the final ribonucleoprotein complex provides the desired sequence specificity for the action of the additional amino acid sequence.

Therefore, the invention also provides a method of non-homologous end joining of a dsDNA molecule in a cell at a desired locus to remove at least a part of a nucleotide sequence from the dsDNA molecule; optionally to knockout the function of a gene or genes, wherein the method comprises making double stranded breaks using any of the methods of modifying a target nucleic acid as hereinbefore described.

The invention further provides a method of homologous recombination of a nucleic acid into a dsDNA molecule in a cell at a desired locus in order to modify an existing nucleotide sequence or insert a desired nucleotide sequence, wherein the method comprises making a double or single stranded break at the desired locus using any of the methods of modifying a target nucleic acid as hereinbefore described.

The invention therefore also provides a method of modifying, activating or repressing gene expression in an organism comprising modifying, activating transcription or repressing transcription of a target nucleic acid sequence according to any of the methods hereinbefore described, wherein the nucleic acid is dsDNA and the functional moiety is selected from a DNA modifying enzyme (e.g. a demethylase or deacetylase), a transcription activator or a transcription repressor.

The invention additionally provides a method of modifying, activating or repressing gene expression in an organism comprising modifying, activating transcription or repressing transcription of a target nucleic acid sequence according to any of the methods hereinbefore described, wherein the nucleic acid is an mRNA and the functional moiety is a ribonuclease; optionally selected from an endonuclease, a 3' exonuclease or a 5' exonuclease.

In any of the methods of the invention as described above, the cell which is subjected to the method may be a prokaryote. Similarly, the cell may be a eukaryotic cell, e.g. a plant cell, an insect cell, a yeast cell, a fungal cell, a mammalian cell or a human cell. When the cell is of a mammal or human then it can be a stem cell (but may not be any human embryonic stem cell). Such stem cells for use in the invention are preferably isolated stem cells. Optionally in accordance with any method the invention a cell is transfected in vitro.

Preferably though, in any of the methods of the invention, the target nucleic acid has a specific tertiary structure, optionally supercoiled, more preferably wherein the target nucleic acid is negatively supercoiled. Advantageously, the ribonucleoprotein complexes of the invention, whether produced in vitro, or whether formed within cells, or whether formed within cells via expression machinery of the cell, can be used to target a locus which would otherwise be difficult to get access to in order to apply the functional activity of a desired component, whether labelling or tagging of a specific sequence, modification of nucleic acid structure, switching on or off of gene expression, or of modification of the target sequence itself involving single or double stranded cutting followed by insertion of one or more nucleotide residues or a cassette.

The invention also includes a pharmaceutical composition comprising a Cascade protein complex or a ribonucleoprotein complex of the invention as hereinbefore described.

The invention further includes a pharmaceutical composition comprising an isolated nucleic acid or an expression vector of the invention as hereinbefore described.

Also provided is a kit comprising a Cascade protein complex of the invention as hereinbefore described plus an RNA molecule of the invention as hereinbefore described.

The invention includes a Cascade protein complex or a ribonucleoprotein complex or a nucleic acid or a vector, as hereinbefore described for use as a medicament.

The invention allows a variety of possibilities to physically alter DNA of prokaryotic or eukaryotic hosts at a specified genomic locus, or change expression patterns of a gene at a given locus. Host genomic DNA can be cleaved or modified by methylation, visualized by fluorescence, transcriptionally activated or repressed by functional domains such as nucleases, methylases, fluorescent proteins, transcription activators or repressors respectively, fused to suitable Cascade-subunits. Moreover, the RNA-guided RNA-binding ability of Cascade permits the monitoring of RNA trafficking in live cells using fluorescent Cascade fusion proteins, and provides ways to sequester or destroy host mRNAs causing interference with gene expression levels of a host cell.

In any of the methods of the invention, the target nucleic acid may be defined, preferably so if dsDNA, by the presence of at least one of the following nucleotide triplets: 5'-CTT-3', 5'-CAT-3', 5'-CCT-3', or 5'-CTC-3' (or 5'-CUU-3', 5'-CAU-3', 5'-CCU-3', or 5'-CTC-3' if the target is an RNA). The location of the triplet is in the target strand adjacent to the sequence to which the RNA molecule component of a ribonucleoprotein of the invention hybridizes. The triplet marks the point in the target strand sequence at which base pairing with the RNA molecule component of the ribonucleoprotein does not take place in a 5' to 3' (downstream) direction of the target (whilst it takes place upstream of the target sequence from that point subject to the preferred length of the RNA sequence of the RNA molecule component of the ribonucleoprotein of the invention). In the context of a native type I CRISPR system, the triplets correspond to what is known as a "PAM" (protospacer adjacent motif). For ssDNA or ssRNA targets, presence of one of the triplets is not so necessary.

The invention will now be described in detail and with reference to specific examples and drawings in which:

FIGS. 1A-1H show the results of gel-shift assays where Cascade binds negatively supercoiled (nSC) plasmid DNA but not relaxed DNA. FIG. 1A Gel-shift of nSC plasmid DNA with J3-Cascade, containing a targeting (J3) crRNA. pUC-λ was mixed with 2-fold increasing amounts of J3-Cascade, from a pUC-λ: Cascade molar ratio of 1:0.5 up to a 1:256 molar ratio. The first and last lanes contain only pUC-λ. FIG. 1B Gel-shift as in (A) with R44-Cascade containing a non-targeting (R44) cRNA. FIG. 1C Gel-shift as in (A) with Nt.BspQI nicked pUC-λ. FIG. 1D Gel-shift as in (A) with PdmI linearized pUC-λ. FIG. 1E Fit of the fraction pUC-λ bound to J3-Cascade plotted against the concentration of free J3-Cascade gives the dissociation constant (Kd) for specific binding. FIG. 1F Fit of the fraction pUC-λ bound to R44-Cascade plotted against the concentration of free R44-Cascade gives the dissociation constant (Kd) for non-specific binding. FIG. 1G Specific binding of Cascade to the protospacer monitored by restriction analysis, using the unique BsmI restriction site in the protospacer sequence. Lane 1 and 5 contain only pUC-λ. Lane 2 and 6 contain pUC-λ mixed with Cascade. Lane 3 and 7 contain pUC-λ mixed with Cascade and subsequent BsmI addition. Lane 4 and 8 contain pUC-λ mixed with BsmI. FIG. 1H Gel-shift of pUC-λ bound to Cascade with subsequent Nt.BspQI cleavage of one strand of the plasmid. Lane 1 and 6 contain only pUC-λ. Lane 2 and 7 contain pUC-λ mixed with Cascade. Lane 3 and 8 contain pUC-λ mixed with Cascade and subsequent Nt.BspQI nicking. Lane 4 and 9 contain pUC-λ mixed with Cascade, followed by addition of a ssDNA probe complementary to the displaced strand in the R-loop and subsequent nicking with Nt.BspQI. Lane 5 and 10 contain pUC-λ nicked with Nt.BspQI. FIG. 1I Gel-shift of pUC-λ bound to Cascade with subsequent EcoRI cleavage of both strands of the plasmid. Lane 1 and 6 contain only pUC-λ. Lane 2 and 7 contain pUC-λ mixed with Cascade. Lane 3 and 8 contain pUC-λ mixed with Cascade and subsequent EcoRI cleavage. Lane 4 and 9 contain pUC-λ mixed with Cascade, followed by addition of a ssDNA probe complementary to the displaced strand in the R-loop and subsequent cleavage with EcoRI. Lane 5 and 10 contain pUC-λ cleaved with EcoRI.

FIG. 2 shows scanning force micrographs demonstrating how Cascade induces bending of target DNA upon protospacer binding. Panels A-P: Scanning force microscopy images of nSC plasmid DNA with J3-Cascade containing a targeting (J3) crRNA. pUC-λ was mixed with J3-Cascade at a pUC-λ: Cascade ratio of 1:7. Each image shows a 500×500 nm surface area. White dots correspond to Cascade.

FIG. 3A, panels A-I shows how BiFC analysis reveals that Cascade and Cas3 interact upon target recognition. Panel A: Venus fluorescence of cells expressing CascadeΔCse1 and CRISPR 7Tm, which targets 7 protospacers on the phage λ genome, and Cse1-N155Venus and Cas3-C85Venus fusion proteins. Panel B: Brightfield image of the cells in (A). Panel C: Overlay of (A) and (B). Panel D: Venus fluorescence of phage λ infected cells expressing CascadeΔCse1 and CRISPR 7Tm, and Cse1-N155Venus and Cas3-C85Venus fusion proteins. Panel E: Brightfield image of the cells in (D). Panel F: Overlay of (D) and (E). Panel G: Venus fluorescence of phage λ infected cells expressing CascadeΔCse1 and non-targeting CRISPR R44, and N155Venus and C85Venus proteins. Panel H: Brightfield image of the cells in (H). Panel I: Overlay of (G) and (H). FIG. 3B: average of the fluorescence intensity of 4-7 individual cells of each strain, as determined using the profile tool of LSM viewer (Carl Zeiss).

FIGS. 4A and 4B show Cas3 nuclease and helicase activities during CRISPR-interference. FIG. 4A: Competent BL21-AI cells expressing Cascade, a Cas3 mutant and CRISPR J3 were transformed with pUC-λ. Colony forming units per microgram pUC-λ (cfu/μg DNA) are depicted for each of the strains expressing a Cas3 mutant. Cells expressing wt Cas3 and CRISPR J3 or CRISPR R44 serve as positive and negative controls, respectively. FIG. 4B: BL21-AI cells carrying Cascade, Cas3 mutant, and CRISPR encoding plasmids as well as pUC-λ are grown under conditions that suppress expression of the cas genes and CRISPR. At t=0 expression is induced. The percentage of cells that lost pUC-λ over time is shown, as determined by the ratio of ampicillin sensitive and ampicillin resistant cells.

FIGS. 5A-5H show how a Cascade-Cas3 fusion complex provides in vivo resistance and has in vitro nuclease activity. FIG. 5A: Coomassie Blue stained SDS-PAGE of purified Cascade and Cascade-Cas3 fusion complex. FIG. 5B: Efficiency of plaquing of phage k on cells expressing Cascade-Cas3 fusion complex and a targeting (J3) or non-targeting (R44) CRISPR and on cells expressing Cascade and Cas3 separately together with a targeting (J3) CRISPR. FIG. 5C: Gel-shift (in the absence of divalent metal ions) of nSC target plasmid with J3-Cascade-Cas3 fusion complex. pUC-λ was mixed with 2-fold increasing amounts of J3-Cascade-Cas3, from a pUC-λ:J3-Cascade-Cas3 molar ratio of 1:0.5 up to a 1:128 molar ratio. The first and last lane contain only pUC-λ. FIG. 5D: Gel-shift (in the absence of divalent metal ions) of nSC non-target plasmid with J3-Cascade-Cas3 fusion complex. pUC-p7 was mixed with 2-fold increasing amounts of J3-Cascade-Cas3, from a pUC-p7:J3-Cascade-Cas3 molar ratio of 1:0.5 up to a 1:128 molar ratio. The first and last lane contain only pUC-p7. FIG. 5E: Incubation of nSC target plasmid (pUC-λ, left) or nSC non-target plasmid (pUC-p7, right) with J3-Cascade-Cas3 in the presence of 10 mM $MgCl_2$. Lane 1 and 7 contain only plasmid. FIG. 5F: Assay as in (E) in the presence of 2 mM ATP. FIG. 5G: Assay as in (E) with the mutant J3-Cascade-Cas3K320N complex. FIG. 5H: Assay as in (G) in the presence of 2 mM ATP.

Figure 8:
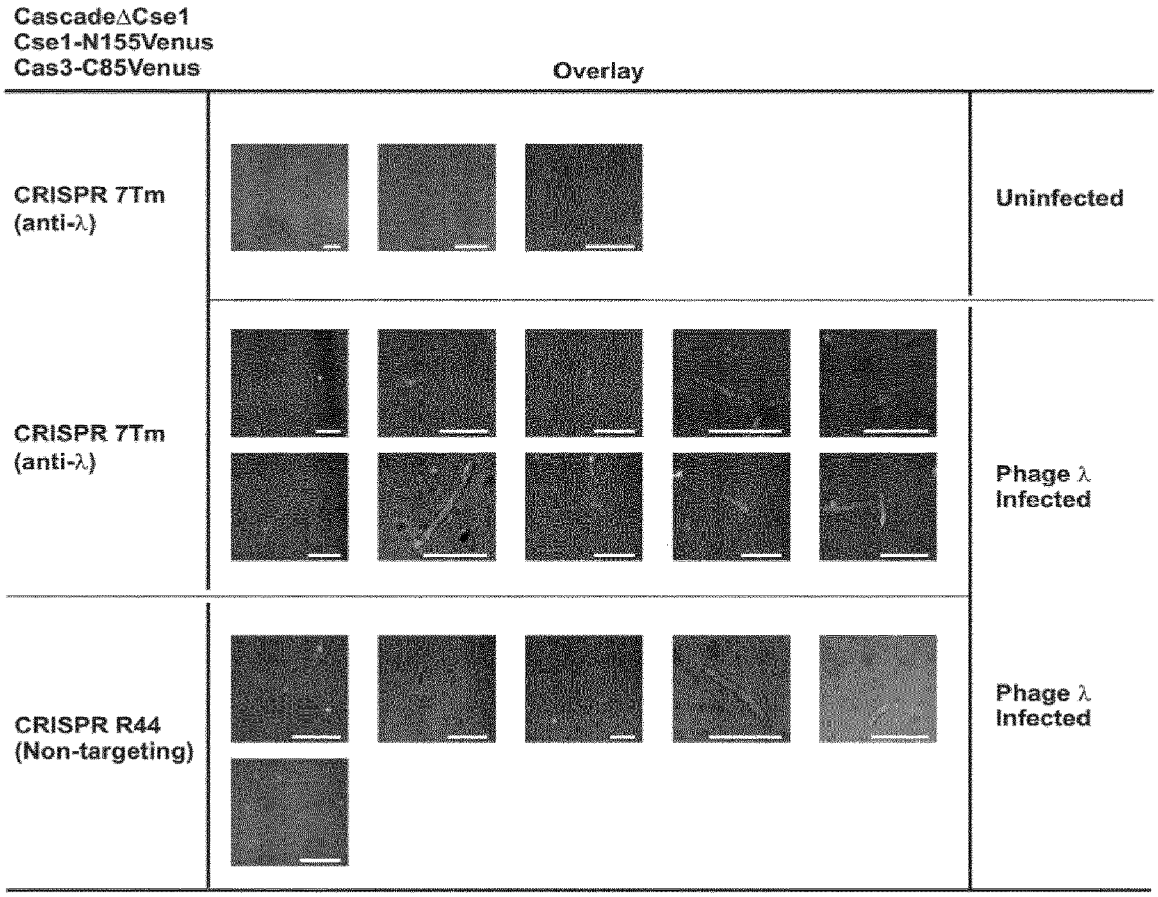

FIG. 8 shows how BiFC analysis reveals that Cascade and Cas3 interact upon target recognition. Overlay of Brightfield image and Venus fluorescence of cells expressing Cascade without Cse1, Cse1-N155Venus and Cas3-C85Venus and either CRISPR 7Tm, which targets 7 protospacers on the phage Lambda genome, or the non-targeting CRISPR R44. Cells expressing CRISPR 7Tm are fluorescent only when infected with phage Lambda, while cells expressing CRISPR R44 are non-fluorescent. The highly intense fluorescent dots (outside cells) are due to light-reflecting salt crystals. White bars correspond to 10 micron.

FIG. 9 shows pUC-λ sequences of 4 clones [SEQ ID NOs: 39-42] encoding CRISPR J3, Cascade and Cas3 (wt or S483AT485A) indicate that these are escape mutants carrying (partial) deletions of the protospacer or carrying a single point mutation in the seed region, which explains the inability to cure these plasmids.

Figure 10A:
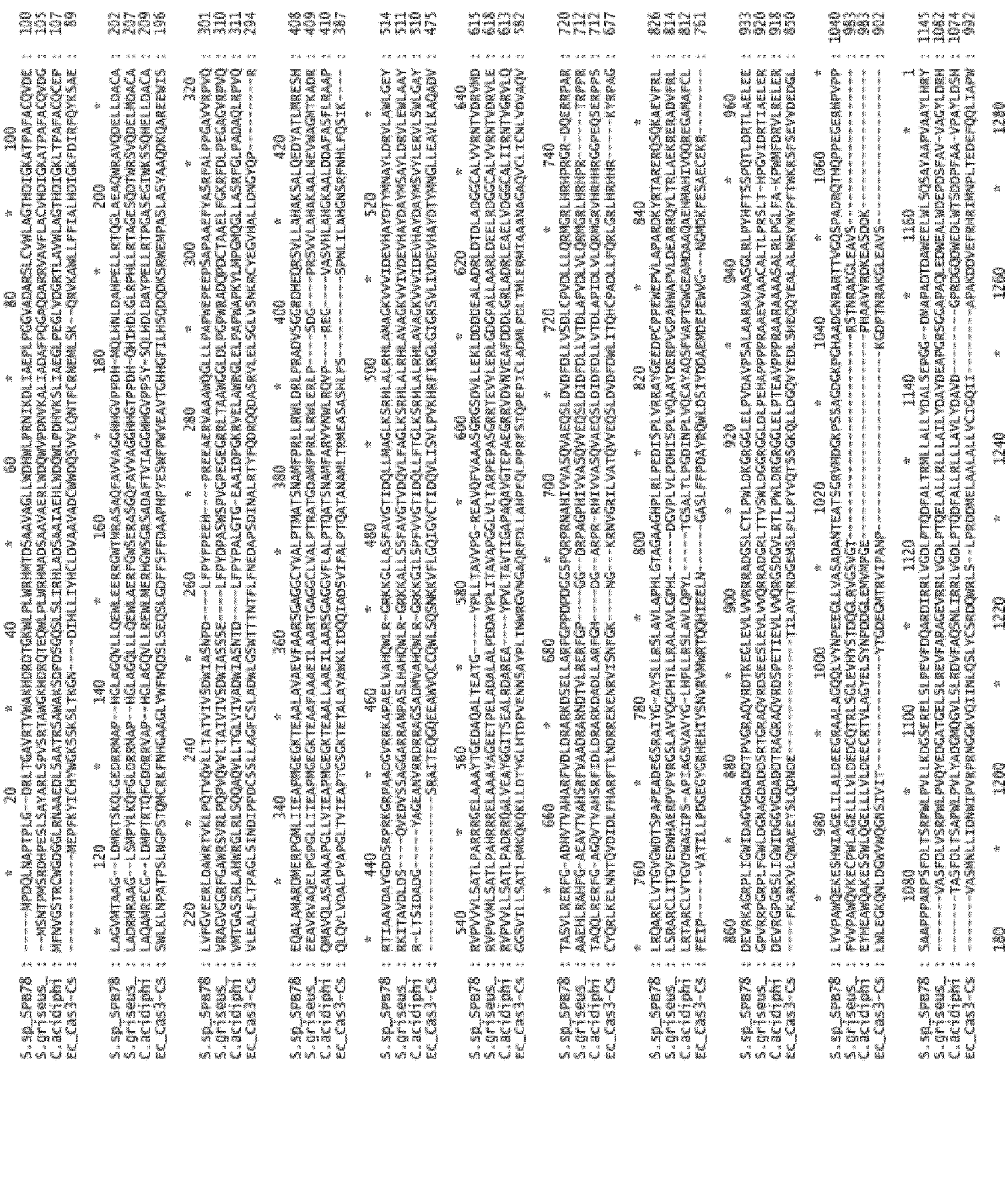
Figure 10B:
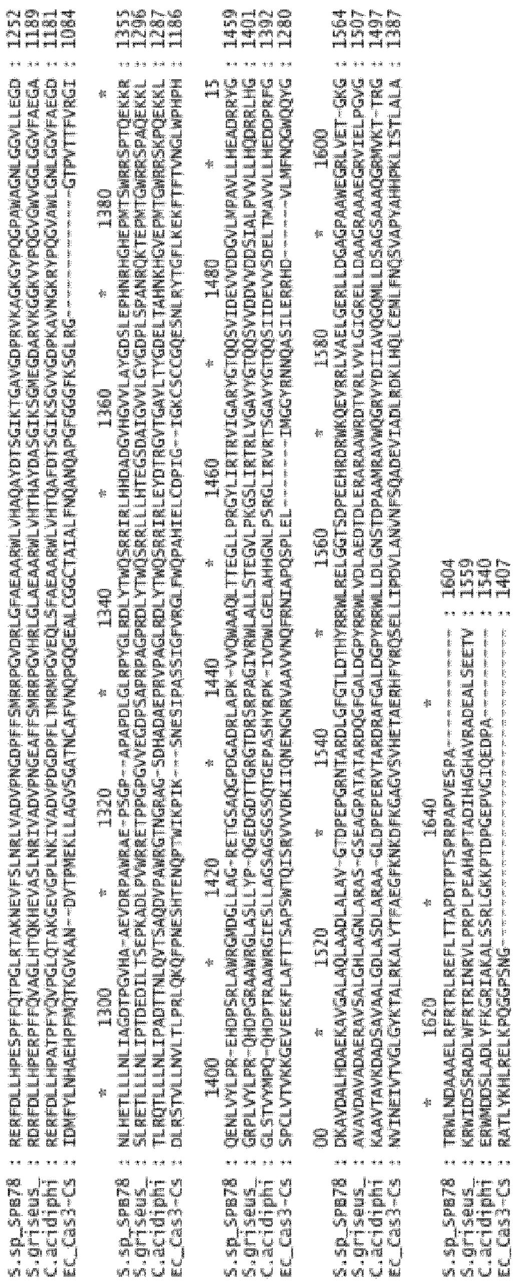

FIGS. 10A and 10B show sequence alignments of cas3 genes from organisms containing the Type I-E CRISPR/Cas system. Alignment of cas3-cse1 genes from *Streptomyces* sp. SPB78 ($1^{st}$ sequence, Accession Number: ZP_07272643.1) [SEQ ID NO: 43], in *Streptomyces griseus* ($2^{nd}$ sequence, Accession Number YP_001825054) [SEQ ID NO: 44], and in *Catenulispora acidiphila* DSM 44928 ($3^{rd}$ sequence, Accession Number YP_003114638) [SEQ ID NO: 45] and an artificial *E. coli* Cas3-Cse1 fusion protein [SEQ ID NO: 46] which includes the polypeptide linker sequence from *S. griseus*.

Figure 11:
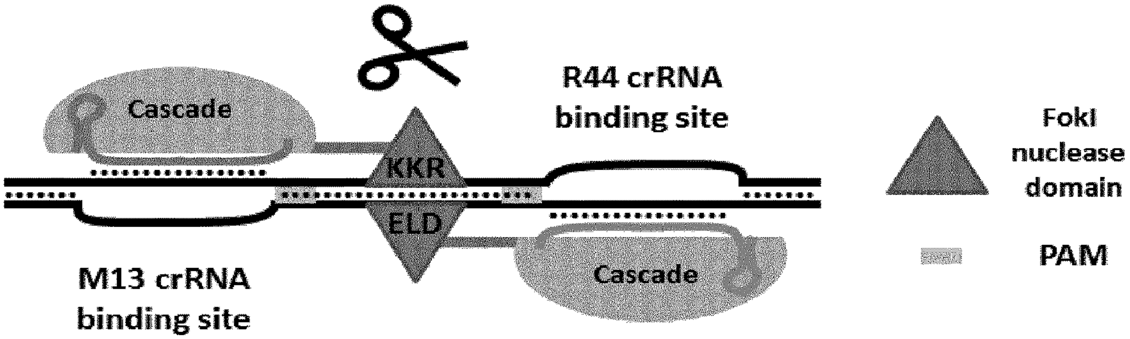

FIG. 11 shows the design of a Cascade$^{KKR/ELD}$ nuclease pair in which FokI nuclease domains are mutated such that only heterodimers consisting of KKR and ELD nuclease domains are and the distance between the opposing binding sites may be varied to determine the optimal distance between a Cascade nuclease pair.

Figure 12:
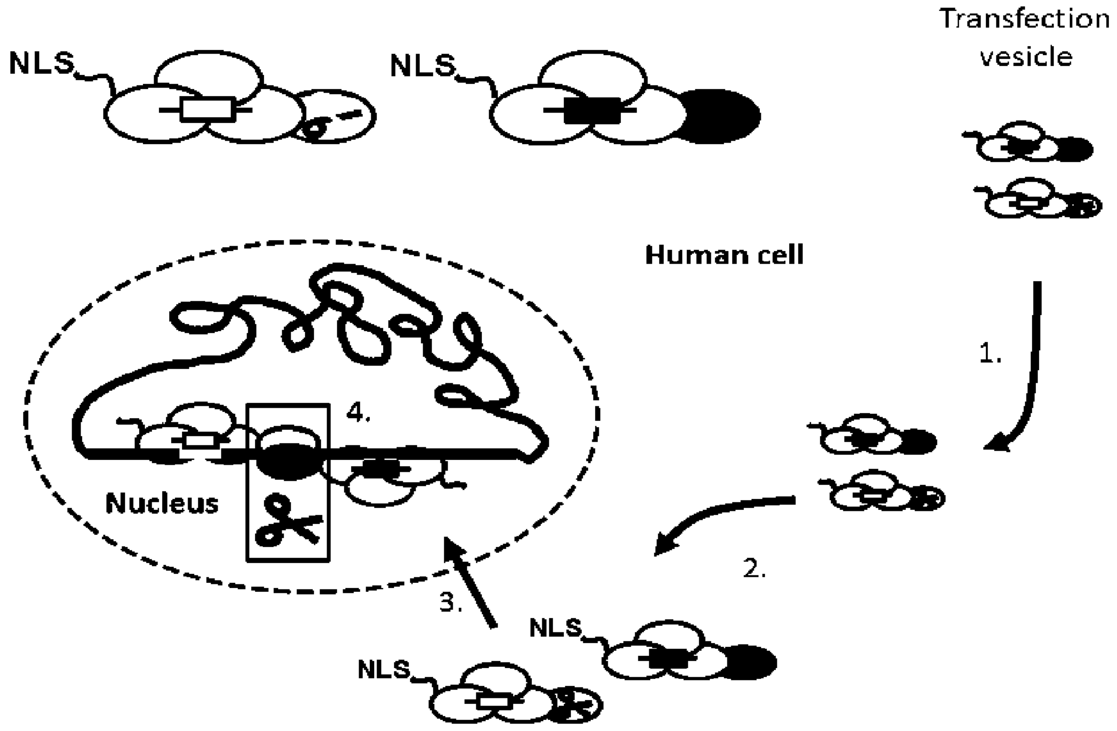

FIG. 12 is a schematic diagram showing genome targeting by a Cascade-FokI nuclease pair.

Figure 13:
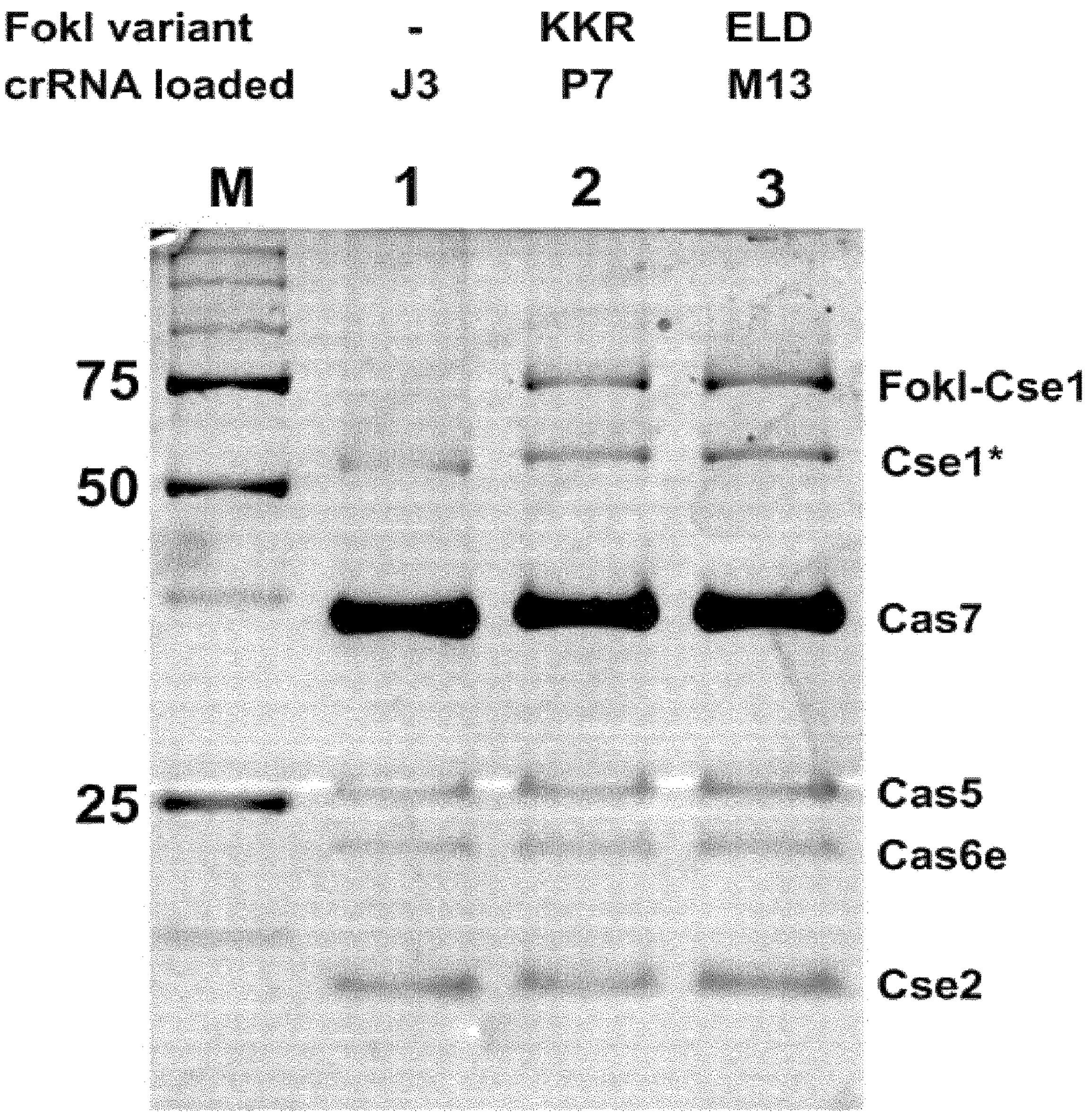

FIG. 13 shows an SDS PAGE gel of Cascade-nuclease complexes.

Figure 14A:
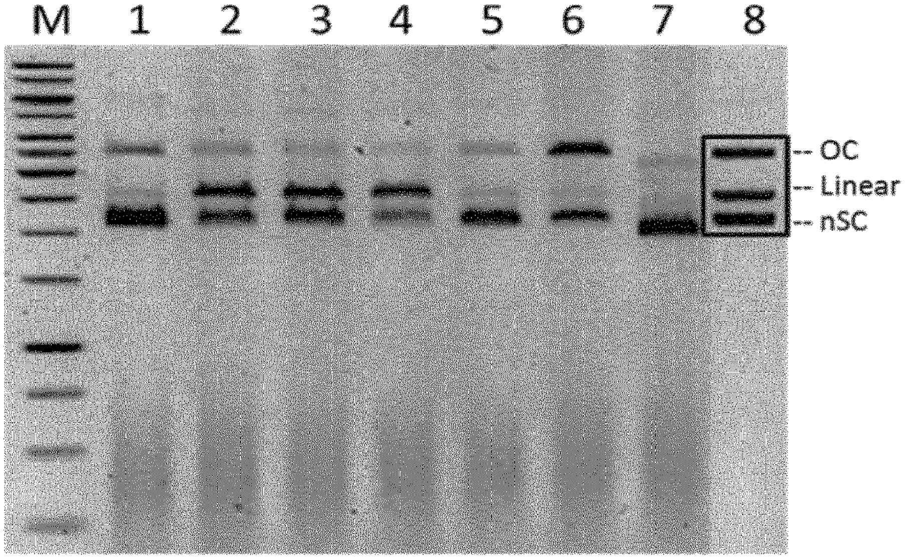
Figure 14B:
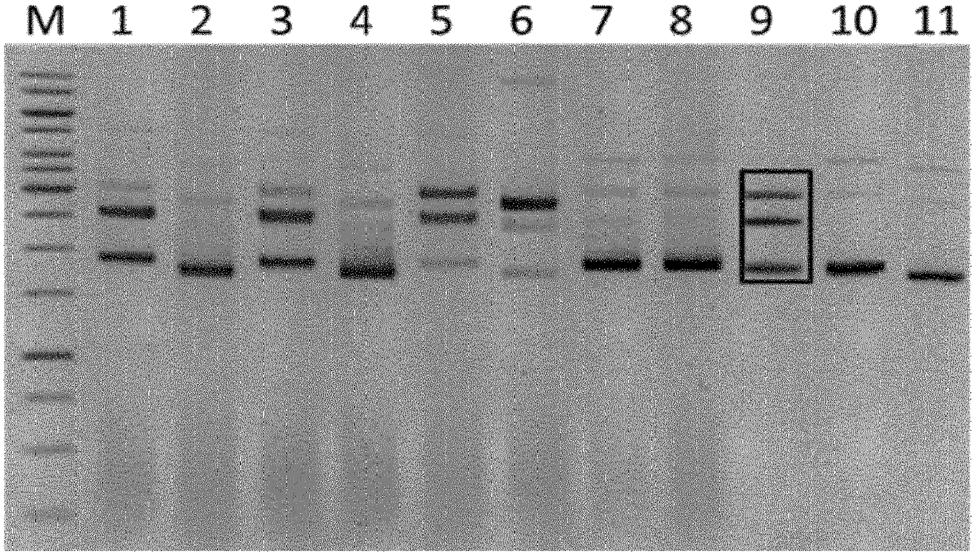

FIGS. 14A and 14B show electrophoresis gels of in vitro cleavage assays of Cascade$^{KKR-ELD}$ on plasmid DNA.

Figure 15A:
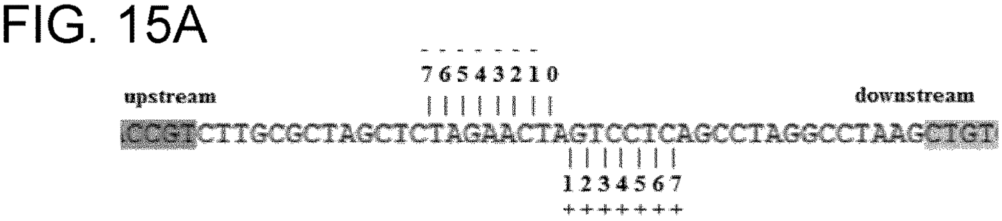
Figure 15B:
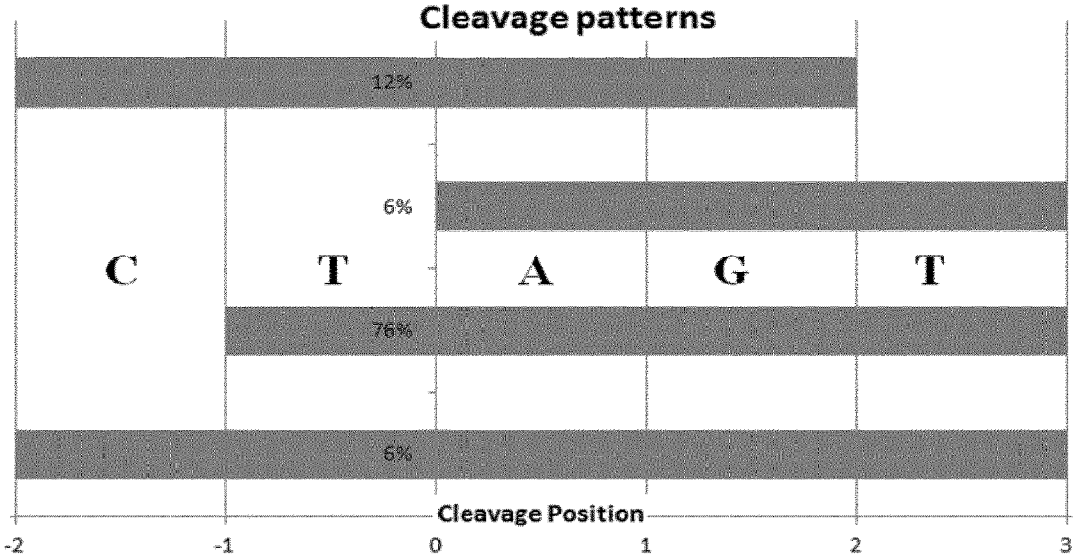

FIGS. 15 and 15B show Cascade$^{KKR/ELD}$ cleavage patterns and frequency [SEQ ID NO: 47].

EXAMPLES—MATERIALS AND METHODS USED

Strains, Gene Cloning, Plasmids and Vectors

*E. coli* BL21-AI and *E. coli* BL21 (DE3) strains were used throughout. Table 1 lists all plasmids used in this study. The previously described pWUR408, pWUR480, pWUR404 and pWUR547 were used for production of Strep-tag II R44-Cascade, and pWUR408, pWUR514 and pWUR630 were used for production of Strep-tag II J3-Cascade (Jore et al., (2011) Nature Structural & Molecular Biology 18, 529-536; Semenova et al., (2011) Proceedings of the National Academy of Sciences of the United States of America 108, 10098-10103.) pUC-λ (pWUR610) and pUC-p7 (pWUR613) have been described elsewhere (Jore et al., 2011; Semenova et al., 2011). The C85Venus protein is encoded by pWUR647, which corresponds to pET52b (Novagen) containing the synthetic GA1070943 construct (Table 2) (Geneart) cloned between the BamHI and NotI sites. The N155Venus protein is encoded by pWUR648, which corresponds to pRSF1b (Novagen) containing the synthetic GA1070941 construct (Table 2) (Geneart) cloned between the NotI and XhoI sites. The Cas3-C85Venus fusion protein is encoded by pWUR649, which corresponds to pWUR647 containing the Cas3 amplification product using primers BG3186 and BG3213 (Table 3) between the NcoI and BamHI sites. The CasA-N155Venus fusion protein is encoded by pWUR650, which corresponds to pWUR648 containing the CasA amplification product using primers BG3303 and BG3212 (Table 3) between the NcoI, and BamHI sites. CRISPR 7Tm is encoded by pWUR651, which corresponds to pACYCDuet-1 (Novagen) containing the synthetic GA1068859 construct (Table 2) (Geneart) cloned between the NcoI and KpnI sites. The Cascade encoding pWUR400, the CascadeΔCse1 encoding WUR401 and the Cas3 encoding pWUR397 were described previously (Jore et al., 2011). The Cas3H74A encoding pWUR652 was constructed using site directed mutagenesis of pWUR397 with primers BG3093, BG3094 (Table 3).

TABLE 1

Plasmids used

| Plasmids | Description and order of genes (5'-3') | Restriction sites | Primers | Source |
|---|---|---|---|---|
| pWUR397 | cas3 in pRSF-1b, no tags | | | 1 |
| pWUR400 | casA-casB-casC-casD-casE in pCDF-1b, no tags | | | 1 |
| pWUR401 | casB-casC-casD-casE in pCDF-1b, no tags | | | 1 |
| pWUR404 | casE in pCDF-1b, no tags | | | 1 |
| pWUR408 | casA in pRSF-1b, no tags | | | 1 |
| pWUR480 | casB with Strep-tag II (N-term)-casC-casD in pET52b | | | 1 |
| pWUR514 | casB with Strep-tag II (N-term)-casC-casD-CasE in pET52b | | | 2 |
| pWUR547 | *E. coli* R44 CRISPR, 7x spacer nr. 2, in pACYCDuet-1 | | | 2 |
| pWUR613 | pUC-p7; pUC19 containing R44-protospacer on a 350 bp phage P7 amplicon | | | 2 |
| pWUR630 | CRISPR poly J3, 5x spacer J3 in pACYCDuet-1 | NcoI/KpnI | | This study |
| pWUR610 | pUC-λ; pUC19 containing J3-protospacer on a 350 bp phage λ amplicon | | | 3 |
| pWUR647 | C85Venus; GA1070943 (Table S1) in pET52b | BamHI/NotI | | This study |
| pWUR648 | N155Venus; GA1070941 (Table S1) in pRSF1b | NotI/XhoI | | This study |
| pWUR649 | cas3-C85Venus; pWUR647 containing cas3 amplicon | NcoI/BamHI | BG3186 + BG3213 | This study |
| pWUR650 | casA-N155Venus pWUR648 containing casA amplicon | NcoI/NotI | BG3303 + BG3212 | This study |

TABLE 1-continued

| Plasmids used | | | | |
|---|---|---|---|---|
| Plasmids | Description and order of genes (5'-3') | Restriction sites | Primers | Source |
| pWUR651 | CRISPR 7Tm; GA1068859 (Table S1) in pACYCDuet-1 | NcoI/KpnI | | This study |
| | casB with Strep-tag II (N-term)-casC-casD-CasE in pCDF-1b | | | This study |
| | cas3-casA fusion | | | This study |
| | cas3H74A-CasA fusion | | | This study |
| | cas3D75A-CasA fusion | | | This study |
| | cas3K320N-CasA fusion | | | This study |
| | cas3D452N-CasA fusion | | | This study |

Source 1 in the table above is Brouns et al (2008) Science 321, 960-964.

Source 2 in the table above is Jore et al (2011) Nature Structural & Molecular Biology 18: 529-537.

TABLE 2

| Synthetic Constructs |
|---|
| GA1070943 |
| ACTGGAAAGCGGGCAGTGAAAGGAAGGCCCATGAGGCCAGTTAATTAAGC |
| GGATCCTGGCGGCGGCAGCGGCGGCGGCAGCGACAAGCAGAAGAACGGCA |
| TCAAGGCGAACTTCAAGATCCGCCACAACATCGAGGACGGCGGCGTGCAG |
| CTCGCCGACCACTACCAGCAGAACACCCCCATCGGCGACGGCCCCGTGCT |
| GCTGCCCGACAACCACTACCTGAGCTACCAGTCCGCCCTGAGCAAAGACC |
| CCAACGAGAAGCGCGATCACATGGTCCTGCTGGAGTTCGTGACCGCCGCC |
| GGGATCACTCTCGGCATGGACGAGCTGTACAAGTAAGCGGCCGCGGCGCG |
| CCTAGGCCTTGACGGCCTTCCTTCAATTCGCCCTATAGTGAG [SEQ ID |
| NO: 6] |
| GA1070941 |
| CACTATAGGGCGAATTGGCGGAAGGCCGTCAAGGCCGCATTTAATTAAGC |
| GGCCGCAGGCGGCGGCAGCGGCGGCGGCAGCATGGTGAGCAAGGGCGAGG |
| AGCTGTTCACCGGGGTGGTGCCCATCCTGGTCGAGCTGGACGGCGACGTA |
| AACGGCCACAAGTTCAGCGTGTCCGGCGAGGGCGAGGGCGATGCCACCTA |
| CGGCAAGCTGACCCTGAAGCTCATCTGCACCACCGGCAAGCTGCCCGTGC |
| CCTGGCCCACCCTCGTGACCACCCTCGGCTACGGCCTGCAGTGCTTCGCC |
| CGCTACCCCGACCACATGAAGCAGCACGACTTCTTCAAGTCCGCCATGCC |
| CGAAGGCTACGTCCAGGAGCGCACCATCTTCTTCAAGGACGACGGCAACT |
| ACAAGACCCGCGCCGAGGTGAAGTTCGAGGGCGACACCCTGGTGAACCGC |
| ATCGAGCTGAAGGGCATCGACTTCAAGGAGGACGGCAACATCCTGGGGCA |
| CAAGCTGGAGTACAACTACAACAGCCACAACGTCTATATCACGGCCTAAC |
| TCGAGGGCGCGCCCTGGGCCTCATGGGCCTTCCGCTCACTGCCCGCTTTC |
| CAG [SEQ ID NO: 7] |

TABLE 2-continued

| Synthetic Constructs |
|---|
| GA1068859 |
| CACTATAGGGCGAATTGGCGGAAGGCCGTCAAGGCCGCATGAGCTCCATG |
| GAAACAAAGAATTAGCTGATCTTTAATAATAAGGAAATGTTACATTAAGG |
| TTGGTGGGTTGTTTTTATGGGAAAAAATGCTTTAAGAACAAATGTATACT |
| TTTAGAGAGTTCCCCGCGCCAGCGGGGATAAACCGGGCCGATTGAAGGTC |
| CGGTGGATGGCTTAAAAGAGTTCCCCGCGCCAGCGGGGATAAACCGCCGC |
| AGGTACAGCAGGTAGCGCAGATCATCAAGAGTTCCCCGCGCCAGCGGGGA |
| TAAACCGACTTCTCTCCGAAAAGTCAGGACGCTGTGGCAGAGTTCCCCGC |
| GCCAGCGGGGATAAACCGCCTACGCGCTGAACGCCAGCGGTGTGGTGAAT |
| GAGTTCCCCGCGCCAGCGGGGATAAACCGGTGTGGCCATGCACGCCTTTA |
| ACGGTGAACTGGAGTTCCCCGCGCCAGCGGGGATAAACCGCACGAACTCA |
| GCCAGAACGACAAACAAAAGGCGAGTTCCCCGCGCCAGCGGGGATAAACC |
| GGCACCAGTACGCGCCCCACGCTGACGGTTTCTGAGTTCCCCGCGCCAGC |
| GGGGATAAACCGCAGCTCCCATTTTCAAACCCAGGTACCCTGGGCCTCAT |
| GGGCCTTCCGCTCACTGCCCGCTTTCCAG [SEQ ID NO: 8] |
| GA1047360 |
| GAGCTCCCGGGCTGACGGTAATAGAGGCACCTACAGGCTCCGGTAAAACG |
| GAAACAGCGCTGGCCTATGCTTGGAAACTTATTGATCAACAAATTGCGGA |
| TAGTGTTATTTTTGCCCTCCCAACACAAGCTACCGCGAATGCTATGCTTA |
| CGAGAATGGAAGCGAGCGCGAGCCACTTATTTTCATCCCCAAATCTTATT |
| CTTGCTCATGGCAATTCACGGTTTAACCACCTCTTTCAATCAATAAAATC |
| ACGCGCGATTACTGAACAGGGGCAAGAAGAAGCGTGGGTTCAGTGTTGTC |
| AGTGGTTGTCACAAAGCAATAAGAAAGTGTTTCTTGGGCAAATCGGCGTT |
| TGCACGATTGATCAGGTGTTGATTTCGGTATTGCCAGTTAAACACCGCTT |
| TATCCGTGGTTTGGGAATTGGTAGATCTGTTTTAATTGTTAATGAAGTTC |
| ATGCTTACGACACCTATATGAACGGCTTGCTCGAGGCAGTGCTCAAGGCT |
| CAGGCTGATGTGGGAGGGAGTGTTATTCTTCTTTCCGCAACCCTACCAAT |
| GAAACAAAAACAGAAGCTTCTGGATACTTATGGTCTGCATACAGATCCAG |
| TGGAAAATAACTCCGCATATCCACTCATTAACTGGCGAGGTGTGAATGGT |
| GCGCAACGTTTTGATCTGCTAGCGGATCCGGTACC [SEQ ID NO: 9] |

TABLE 3

| Primers | |
|---|---|
| BG3186 | ATAGCGCCATGGAACCTTTTAAATATATATGCCATTA [SEQ ID NO: 10] |
| BG3213 | ACAGTGGGATCCGCTTTGGGATTTGCAGGGATGACTC TGGT [SEQ ID NO: 11] |
| BG3303 | ATAGCGTCATGAATTTGCTTATTGATAACTGGATTCC TGTACG [SEQ ID NO: 12] |

TABLE 3-continued

| Primers | |
|---|---|
| BG3212 | ACAGTGGCGGCCGCGCCATTTGATGGCCCTCCTTGCG GTTTTAA [SEQ ID NO: 13] |
| BG3076 | CGTATATCAAACTTTCCAATAGCATGAAGAGCAATGA AAAATAAC [SEQ ID NO: 14] |
| BG3449 | ATGATACCGCGAGACCCACGCTC [SEQ ID NO: 15] |
| BG3451 | CGGATAAAGTTGCAGGACCACTTC [SEQ ID NO: 16] |

Protein Production and Purification

Cascade was expressed and purified as described (Jore et al., 2011). Throughout purification a buffer containing 20 mM HEPES pH 7.5, 75 mM NaCl, 1 mM DTT, 2 mM EDTA was used for resuspension and washing. Protein elution was performed in the same buffer containing 4 mM desthiobiotin. The Cascade-Cas3 fusion complex was expressed and purified in the same manner, with washing steps being performed with 20 mM HEPES pH 7.5, 200 mM NaCl and 1 mM DTT, and elution in 20 mM HEPES pH 7.5, 75 mM NaCl, 1 mM DTT containing 4 mM desthiobiotin.

Electrophoretic Mobility Shift Assay

Purified Cascade or Cascade subsomplexes were mixed with pUC-λ in a buffer containing 20 mM HEPES pH 7.5, 75 mM NaCl, 1 mM DTT, 2 mM EDTA, and incubated at 37° C. for 15 minutes. Samples were run overnight on a 0.8% TAE Agarose gel and post-stained with SybR safe (Invitrogen) 1:10000 dilution in TAE for 30 minutes. Cleavage with BsmI (Fermentas) or Nt.BspQI (New England Biolabs) was performed in the HEPES reaction buffer supplemented with 5 mM $MgCl_2$.

Scanning Force Microscopy

Purified Cascade was mixed with pUC-λ (at a ratio of 7:1, 250 nM Cascade, 35 nM DNA) in a buffer containing 20 mM HEPES pH 7.5, 75 mM NaCl, 0.2 mM DTT, 0.3 mM EDTA and incubated at 37° C. for 15 minutes. Subsequently, for AFM sample preparation, the incubation mixture was diluted 10× in double distilled water and $MgCl_2$ was added at a final concentration of 1.2 mM. Deposition of the protein-DNA complexes and imaging was carried out as described before (Dame et al., (2000) Nucleic Acids Res. 28: 3504-3510).

Fluorescence Microscopy

BL21-AI cells carrying CRISPR en cas gene encoding plasmids, were grown overnight at 37° C. in Luria-Bertani broth (LB) containing ampicillin (100 μg/ml), kanamycin (50 μg/ml), streptomycin (50 μg/ml) and chloramphenicol (34 μg/ml). Overnight culture was diluted 1:100 in fresh antibiotic-containing LB, and grown for 1 hour at 37° C. Expression of cas genes and CRISPR was induced for 1 hour by adding L-arabinose to a final concentration of 0.2% and IPTG to a final concentration of 1 mM. For infection, cells were mixed with phage Lambda at a Multiplicity of Infection (MOI) of 4. Cells were applied to poly-L-lysine covered microscope slides, and analyzed using a Zeiss LSM510 confocal laser scanning microscope based on an Axiovert inverted microscope, with a 40× oil immersion objective (N.A. of 1.3) and an argon laser as the excitation source (514 nm) and detection at 530-600 nm. The pinhole was set at 203 μm for all measurements.

pUC-λ Transformation Studies

LB containing kanamycin (50 μg/ml), streptomycin (50 μg/ml) and chloramphenicol (34 μg/ml) was inoculated from an overnight pre-inoculum and grown to an $OD_{600}$ of 0.3. Expression of cas genes and CRISPR was induced for 45 minutes with 0.2% L-arabinose and 1 mM IPTG. Cells were collected by centrifugation at 4° C. and made competent by resuspension in ice cold buffer containing 100 mM $RbCl_2$, 50 mM $MnCl_2$, 30 mM potassium acetate, 10 mM $CaCl_2$ and 15% glycerol, pH 5.8. After a 3 hour incubation, cells were collected and resuspended in a buffer containing 10 mM MOPS, 10 mM RbCl, 75 mM $CaCl_2$, 15% glycerol, pH 6.8. Transformation was performed by adding 80 ng pUC-λ, followed by a 1 minute heat-shock at 42° C., and 5 minute cold-shock on ice. Next cells were grown in LB for 45 minutes at 37° C. before plating on LB-agar plates containing 0.2% L-arabinose, 1 mM IPTG, ampicillin (100 μg/ml), kanamycin (50 μg/ml), streptomycin (50 μg/ml) and chloramphenicol (34 μg/ml).

Plasmid curing was analyzed by transforming BL21-AI cells containing cas gene and CRISPR encoding plasmids with pUC-λ, while growing the cells in the presence of 0.2% glucose to suppress expression of the T7-polymerase gene. Expression of cas genes and CRISPR was induced by collecting the cells and re-suspension in LB containing 0.2% arabinose and 1 mM IPTG: Cells were plated on LB-agar containing either streptomycin, kanamycin and chloramphenicol (non-selective for pUC-λ) or ampicillin, streptomycin, kanamycin and chloramphenicol (selective for pUC-λ). After overnight growth the percentage of plasmid loss can be calculated from the ratio of colony forming units on the selective and non-selective plates.

Phage Lambda Infection Studies

Host sensitivity to phage infection was tested using a virulent phage Lambda ($\lambda_{vir}$), as in (Brouns et al (2008) Science 321, 960-964.). The sensitivity of the host to infection was calculated as the efficiency of plaquing (the plaque count ratio of a strain containing an anti-λ CRISPR to that of the strain containing a non-targeting R44 CRISPR) as described in Brouns et al (2008).

Example 1—Cascade Exclusively Binds Negatively Supercoiled Target DNA

Figures 1A, 1B, 1C, 1D:
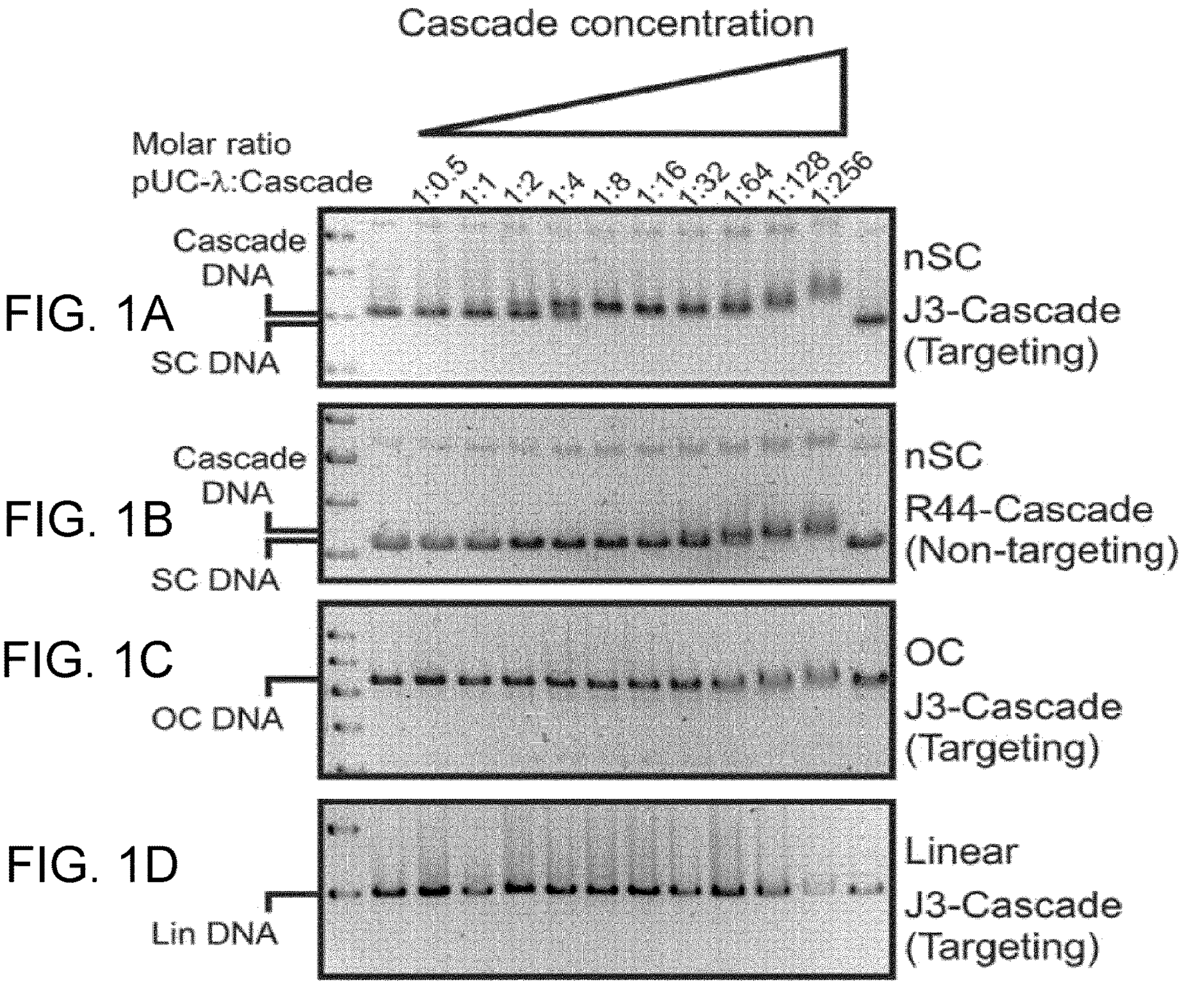
Figure 1E:
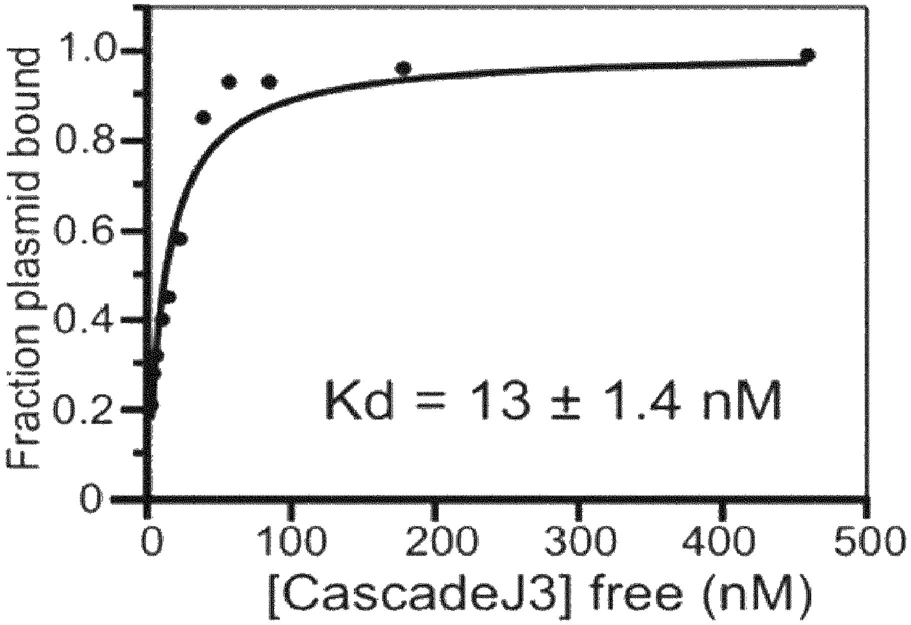
Figure 1F:
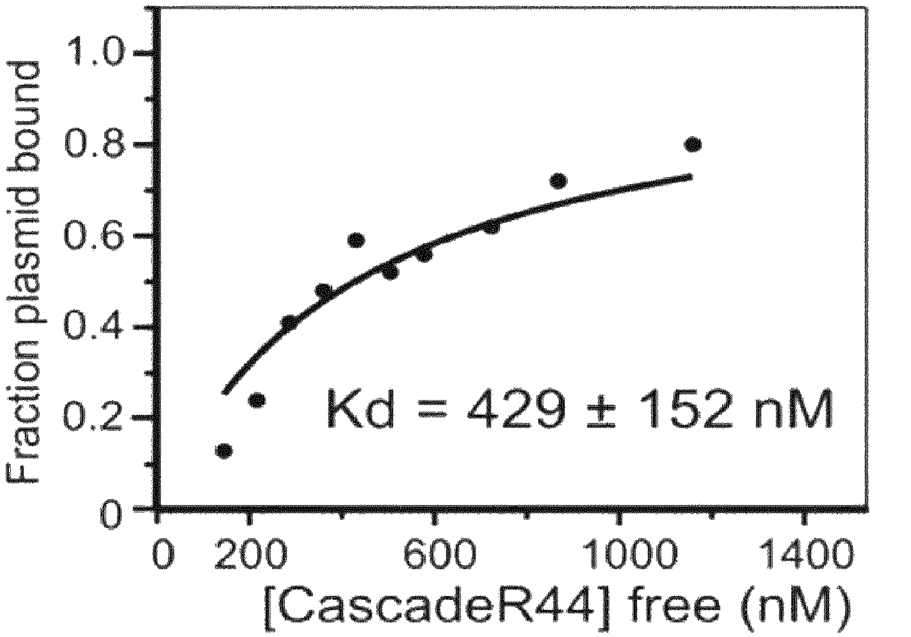

The 3 kb pUC19-derived plasmid denoted pUC-λ, contains a 350 bp DNA fragment corresponding to part of the J gene of phage λ, which is targeted by J3-Cascade (Cascade associated with crRNA containing spacer J3 (Westra et al (2010) Molecular Microbiology 77, 1380-1393). The electrophoretic mobility shift assays show that Cascade has high affinity only for negatively supercoiled (nSC) target plasmid. At a molar ratio of J3-Cascade to pUC-λ of 6:1 all nSC plasmid was bound by Cascade, (see FIG. 1A), while Cascade carrying the non-targeting crRNA R44 (R44-Cascade) displayed non-specific binding at a molar ratio of 128:1 (see FIG. 1B). The dissociation constant (Kd) of nSC pUC-λ was determined to be 13±1.4 nM for J3-Cascade (see FIG. 1E) and 429±152 nM for R44-Cascade (see FIG. 1F).

J3-Cascade was unable to bind relaxed target DNA with measurable affinity, such as nicked (see FIG. 1C) or linear pUC-λ (see FIG. 1D), showing that Cascade has high affinity for larger DNA substrates with a nSC topology.

Figure 1G:
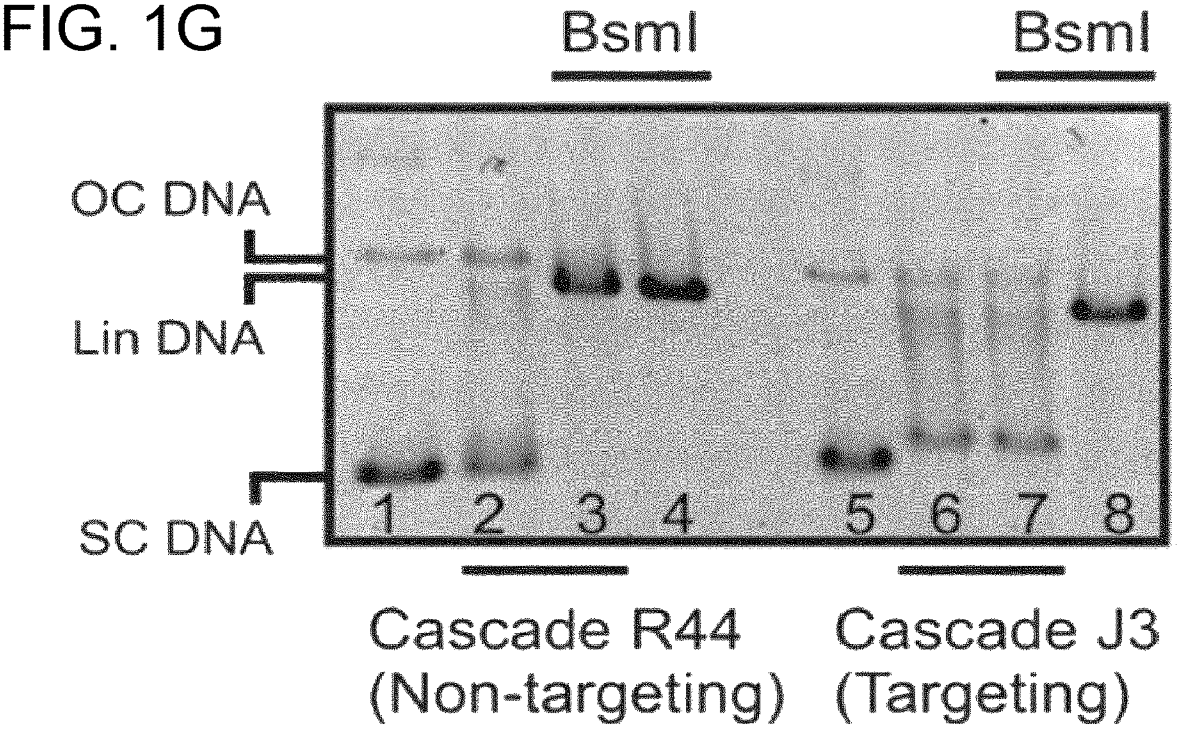

To distinguish non-specific binding from specific binding, the BsmI restriction site located within the protospacer was used. While adding BsmI enzyme to pUC-λ gives a linear product in the presence of R44-Cascade (see FIG. 1G, lane 4), pUC-λ is protected from BsmI cleavage in the presence of J3-Cascade (see FIG. 1G, lane 7), indicating specific binding to the protospacer. This shows that Cas3 is not required for in vitro sequence specific binding of Cascade to a protospacer sequence in a nSC plasmid.

Figure 1H:
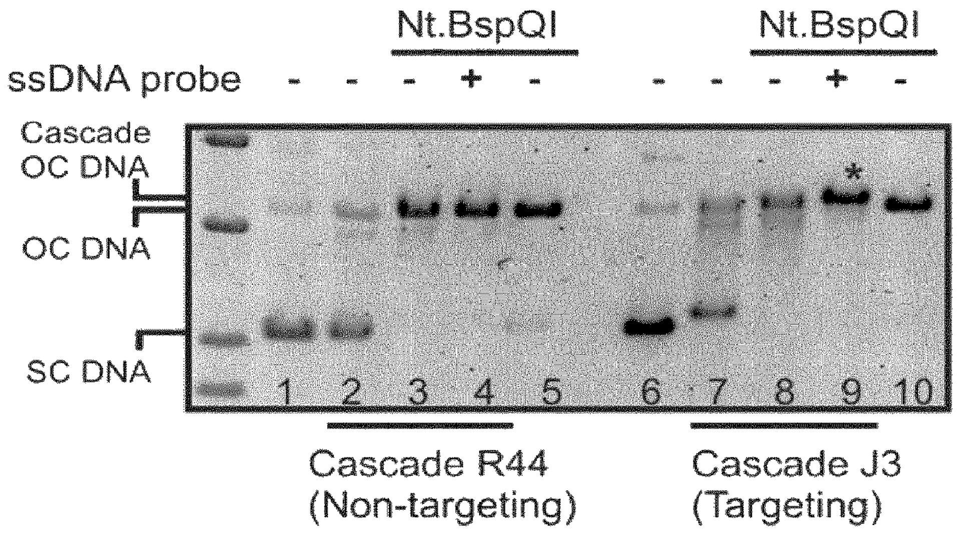
Figure 1I:
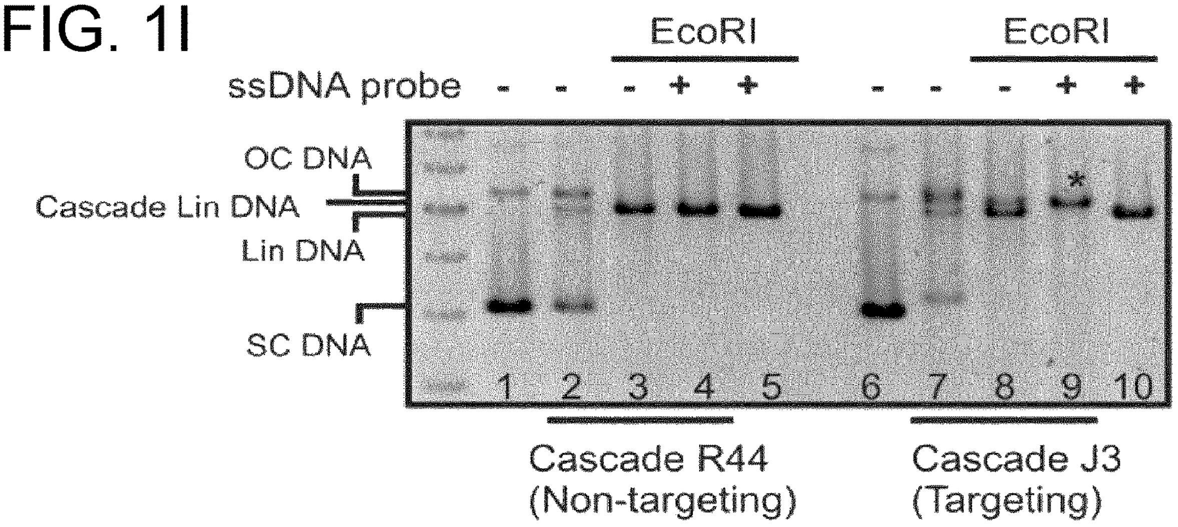

Cascade binding to nSC pUC-λ was followed by nicking with Nt.BspQI, giving rise to an OC topology. Cascade is released from the plasmid after strand nicking, as can be seen from the absence of a mobility shift (see FIG. 1H, compare lane 8 to lane 10). In contrast, Cascade remains bound to its DNA target when a ssDNA probe complementary to the displaced strand is added to the reaction before DNA cleavage by Nt.BspQI (see FIG. 1H, lane 9). The probe artificially stabilizes the Cascade R-loop on relaxed target DNA. Similar observations are made when both DNA strands of pUC-λ are cleaved after Cascade binding (see FIG. 1I, lane 8 and lane 9).

Example 2—Cascade Induces Bending of Bound Target DNA

Figure 2:
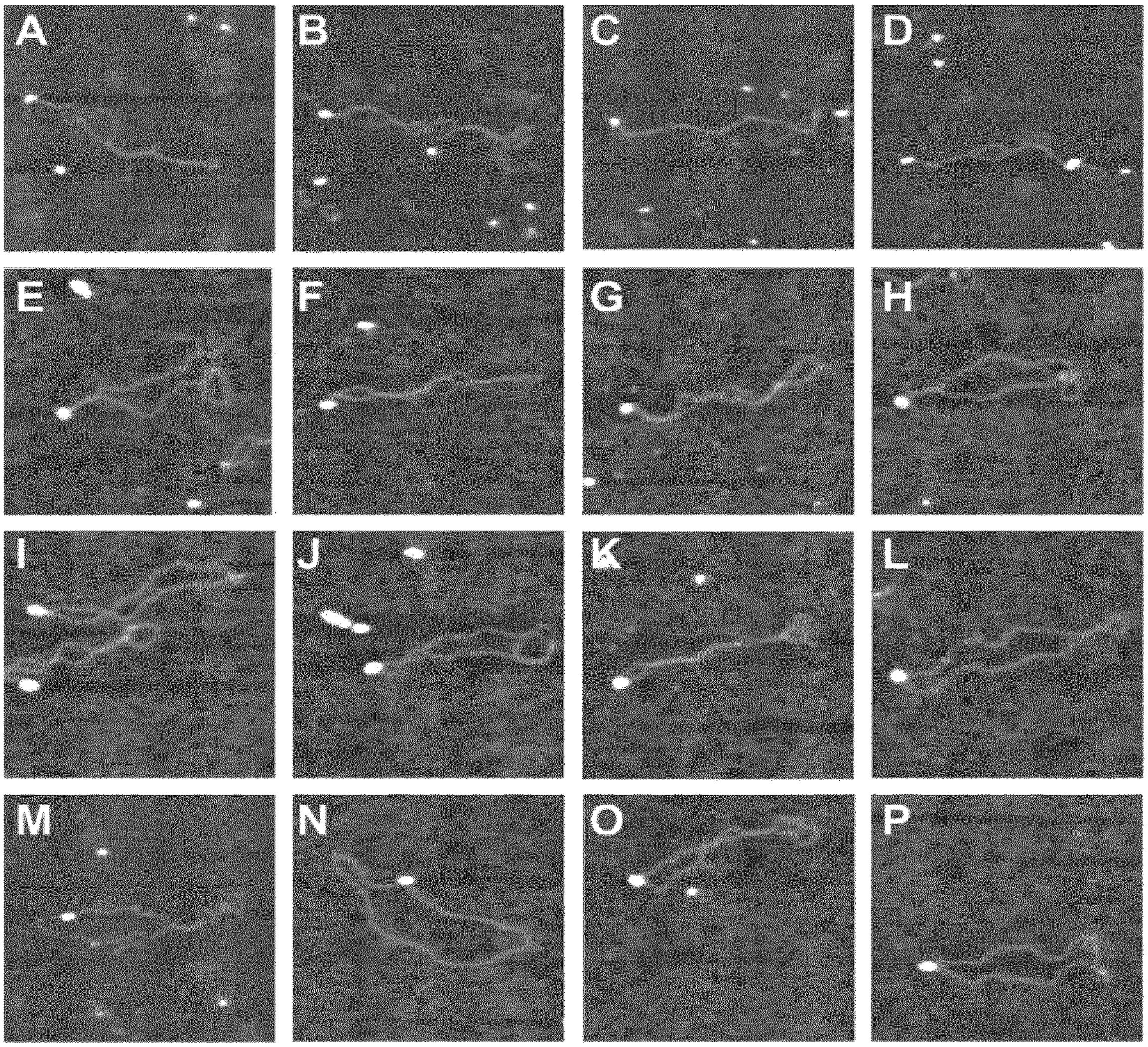

Complexes formed between purified Cascade and pUC-λ were visualized. Specific complexes containing a single bound J3-Cascade complex were formed, while unspecific R44-Cascade yields no DNA bound complexes in this assay under identical conditions. Out of 81 DNA molecules observed 76% were found to have J3-Cascade bound (see FIG. 2A-P). Of these complexes in most cases Cascade was found at the apex of a loop (86%), whereas a small fraction only was found at non-apical positions (14%). These data show that Cascade binding causes bending and possibly wrapping of the DNA, probably to facilitate local melting of the DNA duplex.

Example 3—Naturally Occurring Fusions of Cas3 and Cse1: Cas3 Interacts with Cascade Upon Protospacer Recognition FIGS. 10A and 10B show sequence analysis of cas3 genes from organisms containing the Type I-E CRISPR/Cas system reveals that Cas3 and Cse1 occur as fusion proteins in *Streptomyces* sp. SPB78 (Accession Number: ZP_07272643.1), in *Streptomyces griseus* (Accession Number YP_001825054), and in *Catenulispora acidiphila* DSM 44928 (Accession Number YP_003114638).

Example 4—Bimolecular Fluorescence Complementation (BiFC) Shows how a Cse1 Fusion Protein Forming Part of Cascade Continues to Interact with Cas3

BiFC experiments were used to monitor interactions between Cas3 and Cascade in vivo before and after phage λ infection. BiFC experiments rely on the capacity of the non-fluorescent halves of a fluorescent protein, e.g., Yellow Fluorescent Protein (YFP) to refold and to form a fluorescent molecule when the two halves occur in close proximity. As such, it provides a tool to reveal protein-protein interactions, since the efficiency of refolding is greatly enhanced if the local concentrations are high, e.g., when the two halves of the fluorescent protein are fused to interaction partners. Cse1 was fused at the C-terminus with the N-terminal 155 amino acids of Venus (Cse1-N155Venus), an improved version of YFP (Nagai et al (2002) Nature Biotechnology 20, 87-90). Cas3 was C-terminally fused to the C-terminal 85 amino acids of Venus (Cas3-C85Venus).

Figure 3A:
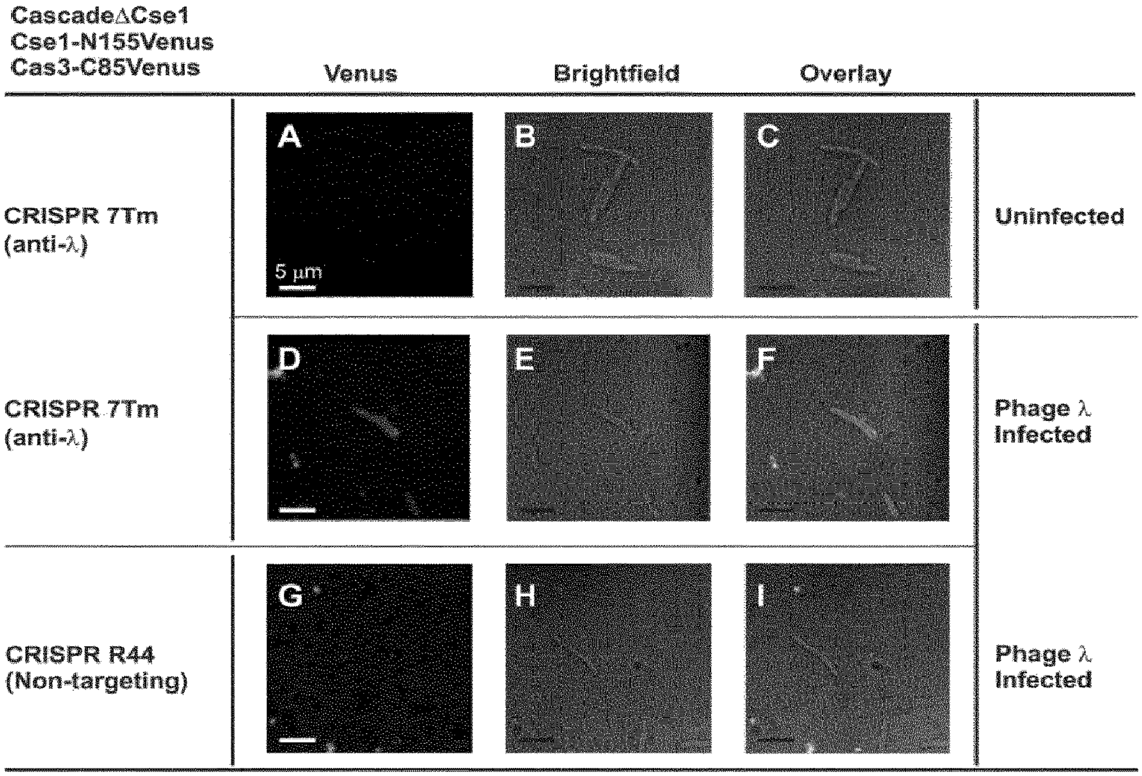
Figure 3B:
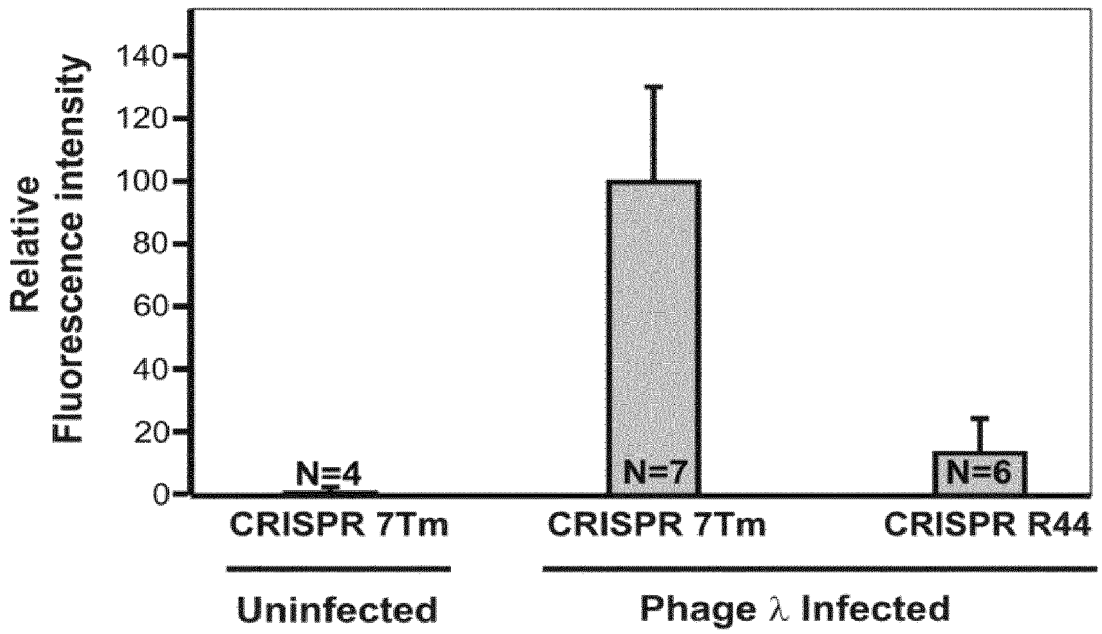
Figure 4A:
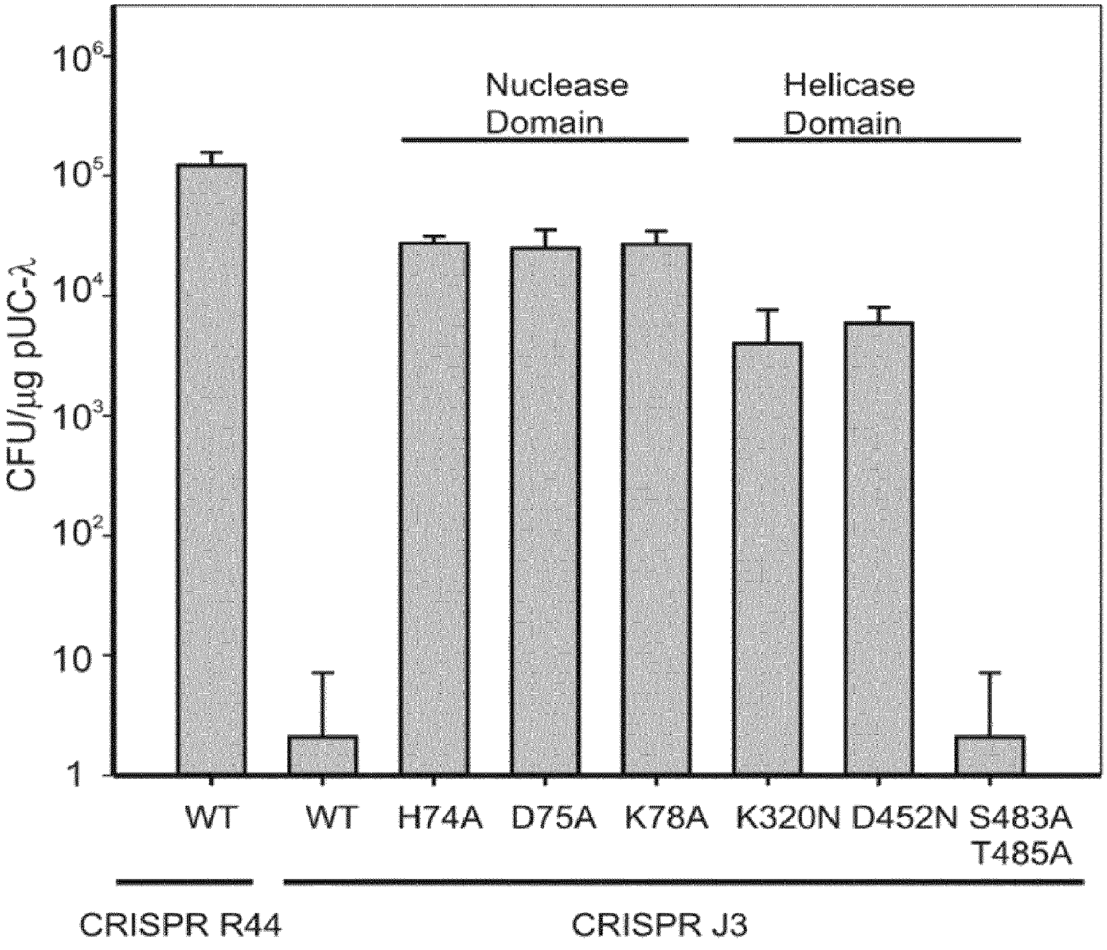
Figure 4B:
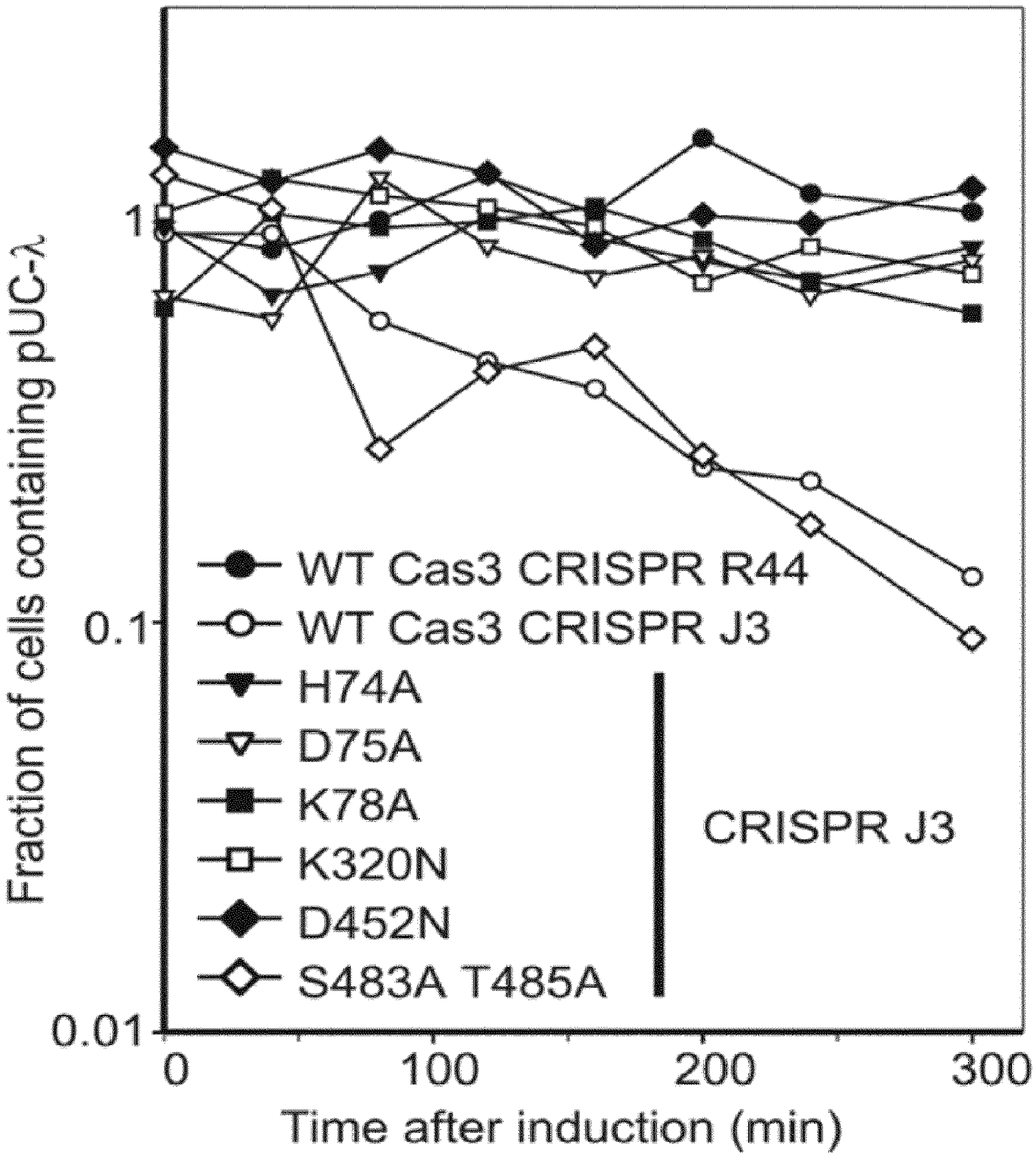

BiFC analysis reveals that Cascade does not interact with Cas3 in the absence of invading DNA (FIG. 3A, FIG. 3B and FIG. 8). Upon infection with phage k, however, cells expressing CascadeΔCse1, Cse1-N155Venus and Cas3-C85Venus are fluorescent if they co-express the anti-λ CRISPR 7Tm (FIG. 3A, panels D, E, F, and FIG. 8). When they co-express a non-targeting CRISPR R44 (FIG. 3A, panels G, H, I, FIG. 3B and FIG. 8), the cells remain non-fluorescent. This. shows that Cascade and Cas3 specifically interact during infection upon protospacer recognition and that Cse1 and Cas3 are in close proximity of each other in the Cascade-Cas3 binary effector complex.

These results also show quite clearly that a fusion of Cse1 with an heterologous protein does not disrupt the ribonucleoprotein formation of Cascade and crRNA, nor does it disrupt the interaction of Cascade and Cas3 with the target phage DNA, even when the Cas3 itself is also a fusion protein.

Figure 5A:
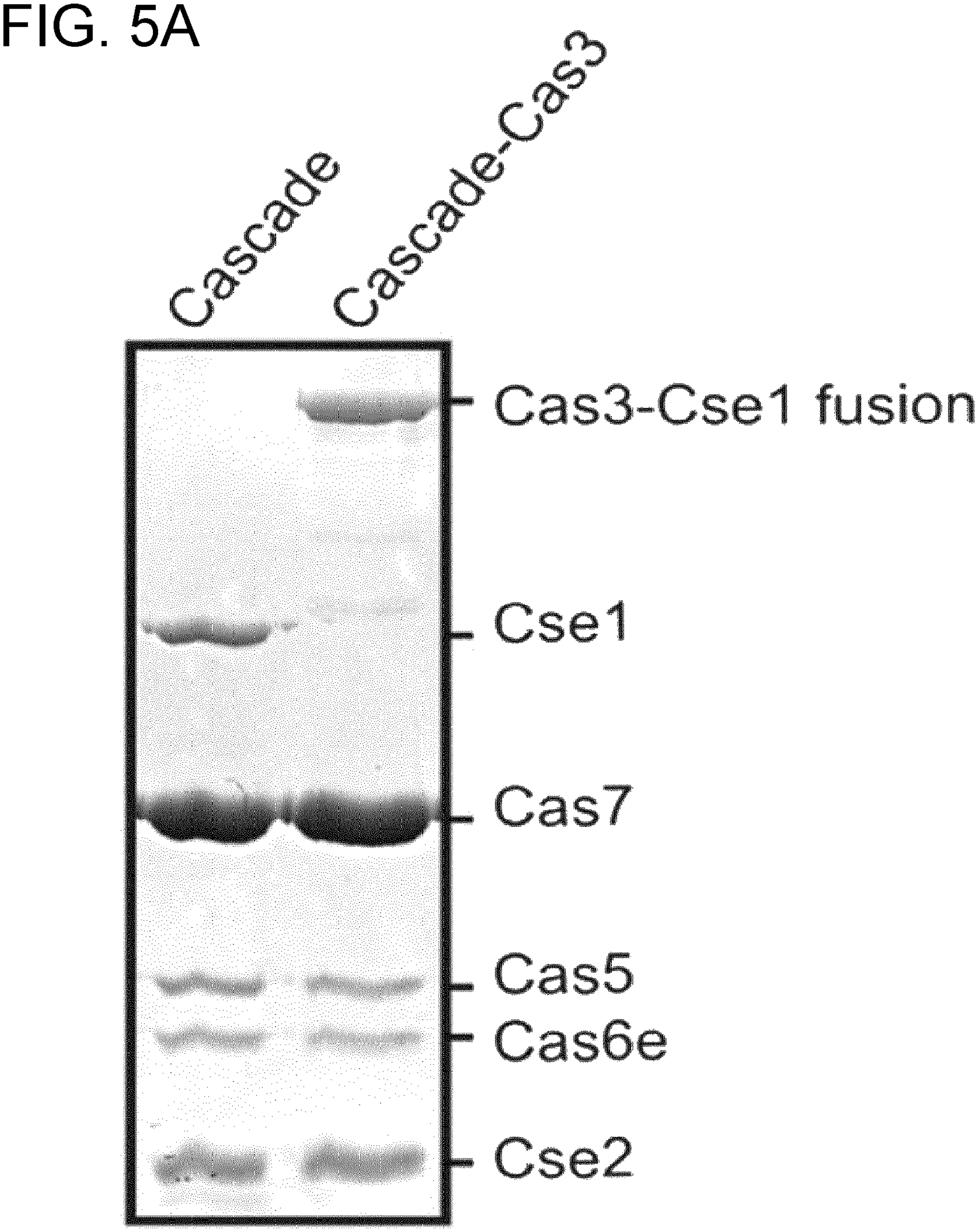
Figure 5B:
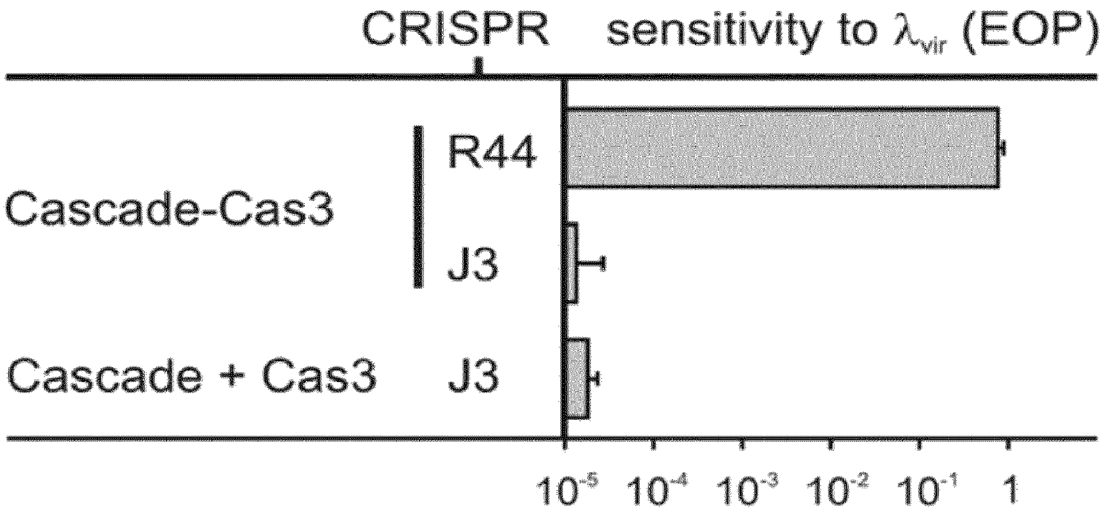

Example 5—Preparing a Designed Cas3-Cse1 Fusion Gives a Protein with In Vivo Functional Activity Providing in vitro evidence for Cas3 DNA cleavage activity required purified and active Cas3. Despite various solubilization strategies, Cas3 overproduced (Howard et al (2011) Biochem. J. 439, 85-95) in *E. coli* BL21 is mainly present in inactive aggregates and inclusion bodies. Cas3 was therefore produced as a Cas3-Cse1 fusion protein, containing a linker identical to that of the Cas3-Cse1 fusion protein in *S. griseus* (see FIG. 10). When co-expressed with CascadeΔCse1 and CRISPR J3, the fusion-complex was soluble and was obtained in high purity with the same apparent stoichiometry as Cascade (FIG. 5A). When functionality of this complex was tested for providing resistance against phage λ infection, the efficiency of plaquing (eop) on cells expressing the fusion-complex J3-Cascade-Cas3 was identical as on cells expressing the separate proteins (FIG. 5B).

Figures 5C, 5D:
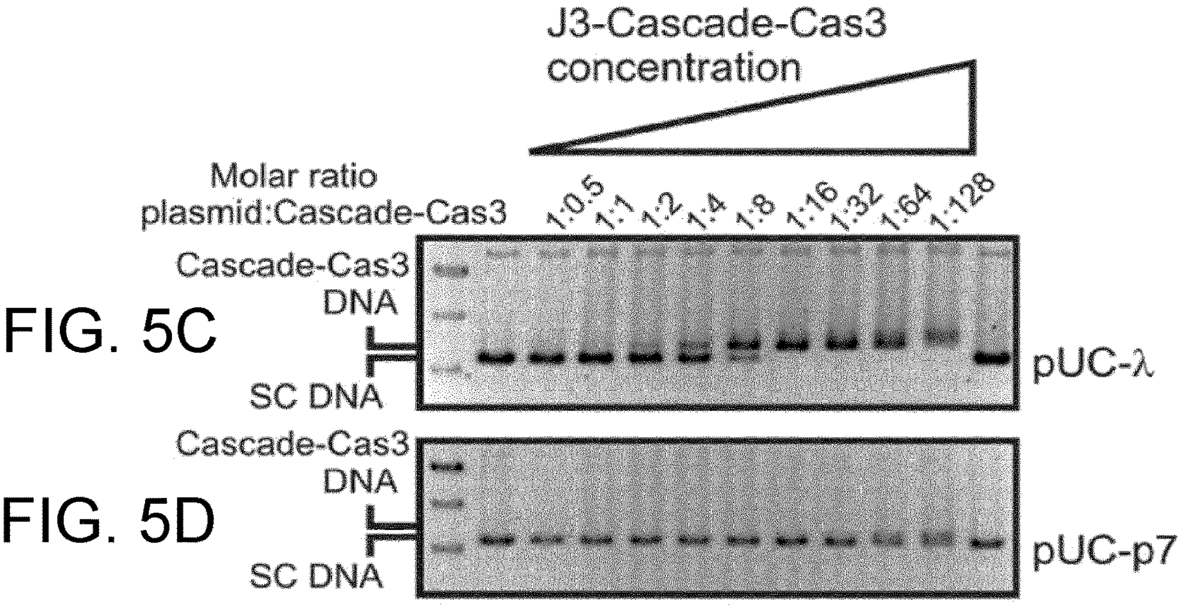

Since the J3-Cascade-Cas3 fusion-complex was functional in vivo, in vitro DNA cleavage assays were carried out using this complex. When J3-Cascade-Cas3 was incubated with pUC-λ in the absence of divalent metals, plasmid binding was observed at molar ratios similar to those observed for Cascade (FIG. 5C), while a-specific binding to a non-target plasmid (pUC-p7, a pUC19 derived plasmid of the same size as pUC-λ, but lacking a protospacer) occurred only at high molar ratios (FIG. 5D), indicating that a-specific DNA binding of the complex is also similar to that of Cascade alone.

Figures 5E, 5F:
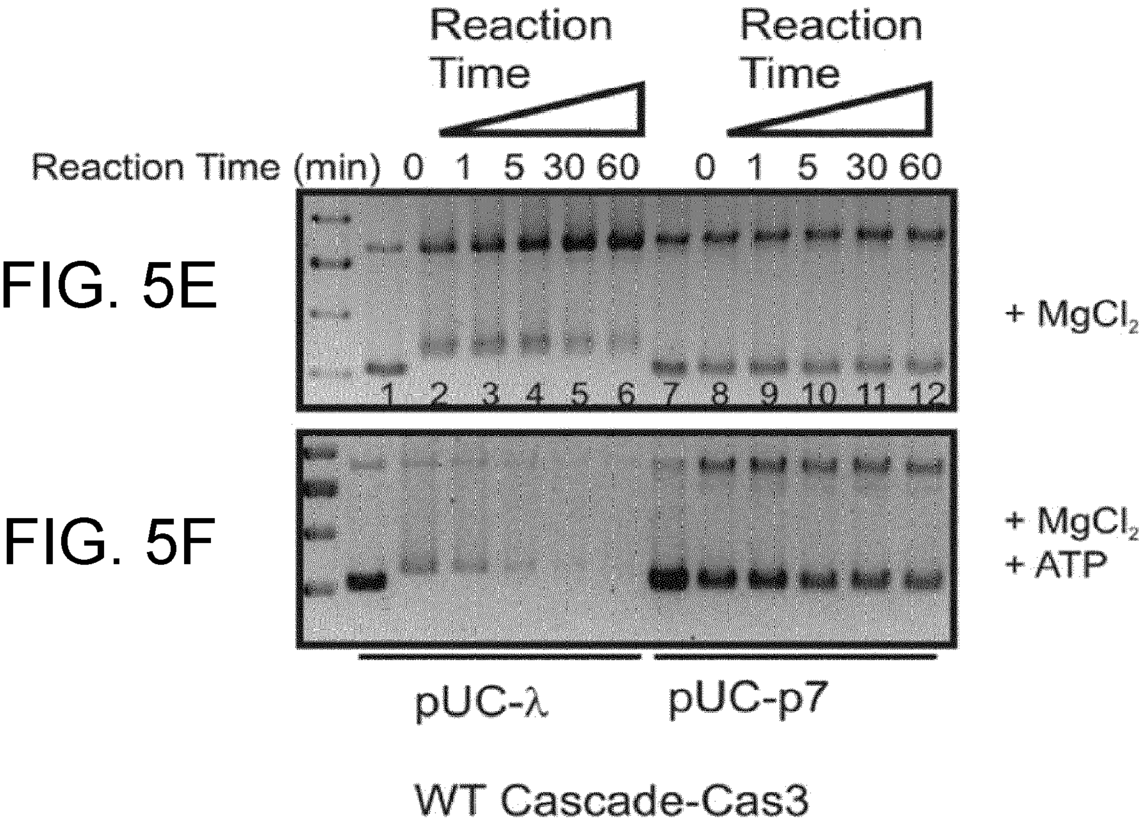
Figures 5G, 5H:
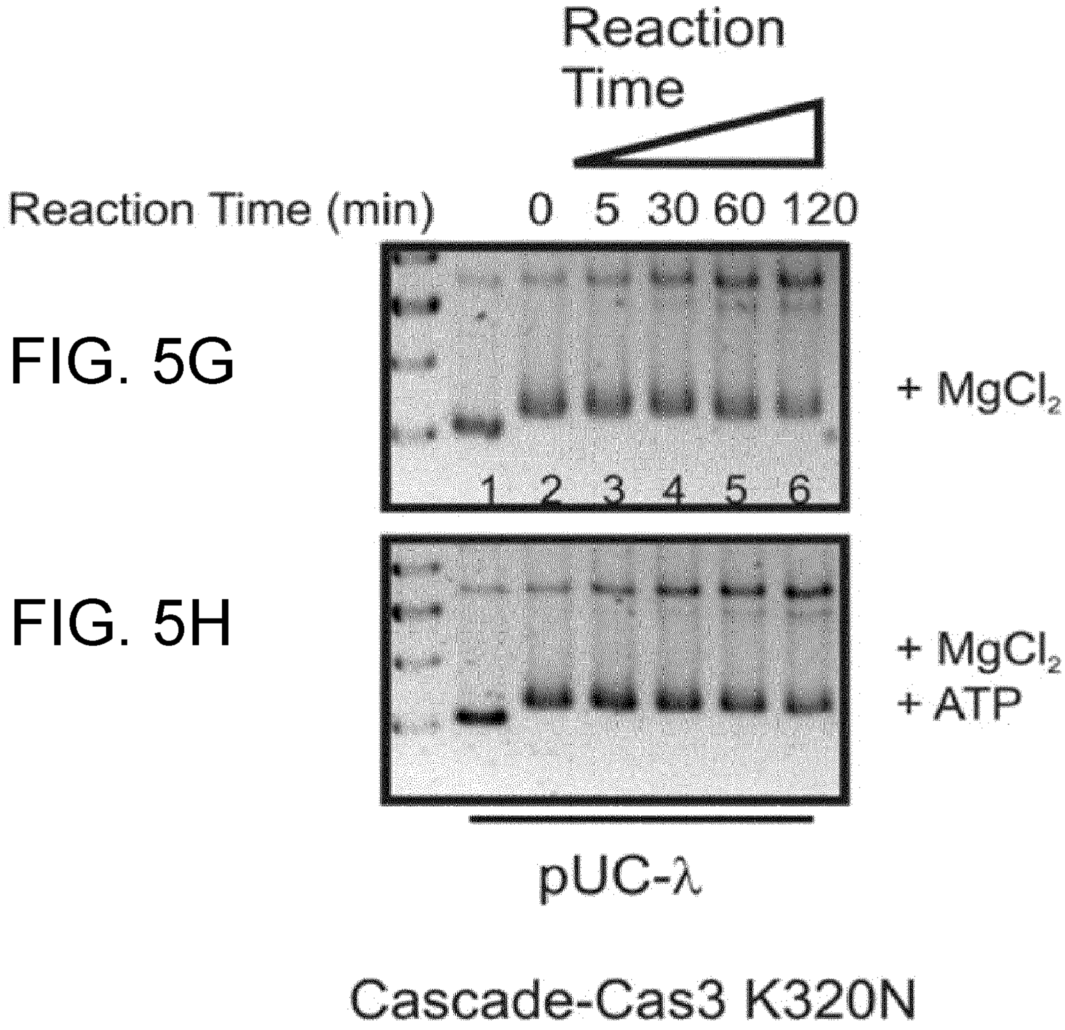

Interestingly, the J3-Cascade-Cas3 fusion complex displays magnesium dependent endonuclease activity on nSC target plasmids. In the presence of 10 mM $Mg^{2+}$ J3-Cascade-Cas3 nicks nSC pUC-λ (FIG. 5E, lane 3-7), but no cleavage is observed for substrates that do not contain the target sequence (FIG. 5E, lane 9-13), or that have a relaxed topology. No shift of the resulting OC band is observed, in line with previous observations that Cascade dissociates spontaneously after cleavage, without requiring ATP-dependent Cas3 helicase activity. Instead, the helicase activity of Cas3 appears to be involved in exonucleolytic plasmid degradation. When both magnesium and ATP are added to the reaction, full plasmid degradation occurred (FIG. 5H).

The inventors have found that Cascade alone is unable to bind protospacers on relaxed DNA. In contrast, the inventors have found that Cascade efficiently locates targets in negatively supercoiled DNA, and subsequently recruits Cas3 via the Cse1 subunit. Endonucleolytic cleavage by the Cas3 HD-nuclease domain causes spontaneous release of Cascade from the DNA through the loss of supercoiling, remobilizing Cascade to locate new targets. The target is then progressively unwound and cleaved by the joint ATP-dependent helicase activity and HD-nuclease activity of Cas3, leading to complete target DNA degradation and neutralization of the invader.

Figure 6:
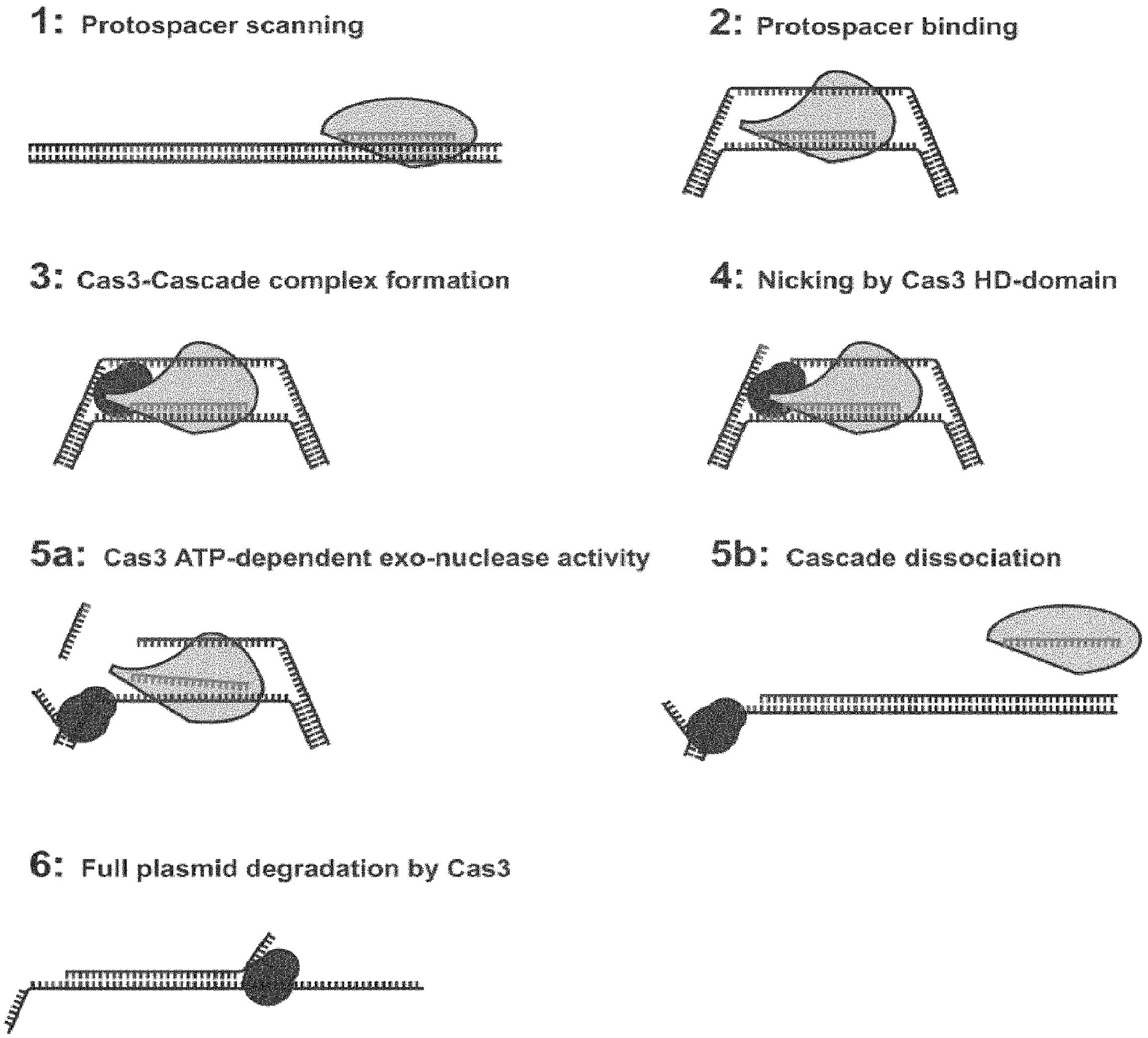
FIG. 6 is a schematic diagram showing a model of the CRISPR-interference type I pathway in *E. coli.*
Figure 7:
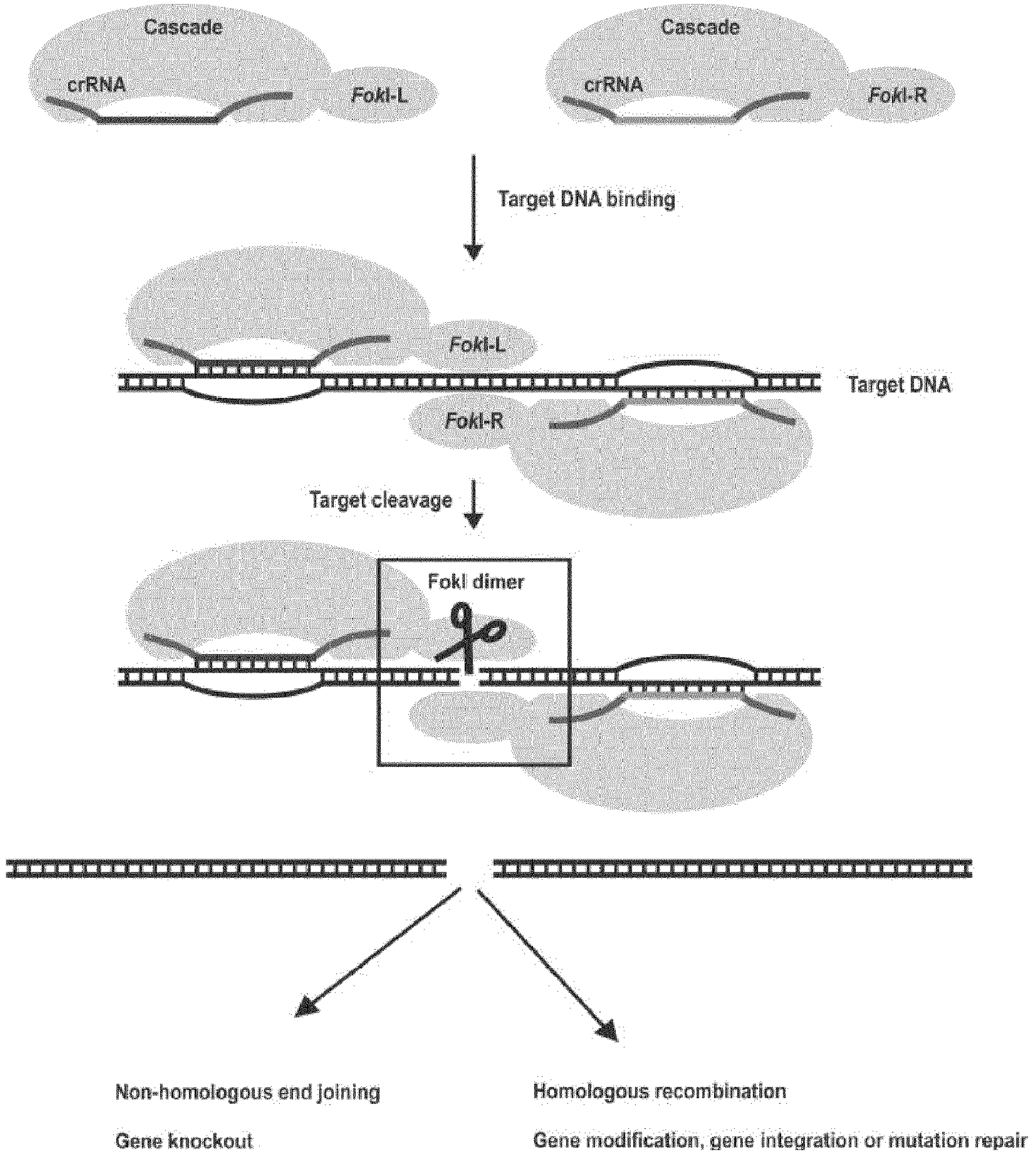
FIG. 7 is a schematic diagram showing how a Cascade-FokI fusion embodiment of the invention is used to create FokI dimers which cuts dsDNA to produce blunt ends as part of a process of non-homologous end joining or homologous recombination.

Referring to FIG. 6 and without wishing to be bound to any particular theory, a mechanism of operation for the CRISPR-interference type I pathway in *E. coli* may involve (1) First, Cascade carrying a crRNA scans the nSC plasmid DNA for a protospacer, with adjacent PAM. Whether during this stage strand separation occurs is unknown. (2) Sequence specific protospacer binding is achieved through basepairing between the crRNA and the complementary strand of the DNA, forming an R-loop. Upon binding, Cascade induces bending of the DNA. (3) The Cse1 subunit of Cascade recruits Cas3 upon DNA binding. This may be achieved by Cascade conformational changes that take place upon nucleic acid binding. (4) The HD-domain (darker part) of Cas3 catalyzes $Mg^{2+}$-dependent nicking of the displaced strand of the R-loop, thereby altering the topology of the target plasmid from nSC to relaxed OC. (5a and 5b) The plasmid relaxation causes spontaneous dissociation of Cascade. Meanwhile Cas3 displays ATP-dependent exonuclease activity on the target plasmid, requiring the helicase domain for target dsDNA unwinding and the HD-nuclease domain for successive cleavage activity. (6) Cas3 degrades the entire plasmid in an ATP-dependent manner as it processively moves along, unwinds and cleaves the target dsDNA.

Example 6—Preparation of Artificial Cas-Strep Tag Fusion Proteins and Assembly of Cascade Complexes Cascade complexes are produced and purified as described in Brouns et al (2008) Science 321: 960-4 (2008), using the expression plasmids listed in Supplementary Table 3 of Jore et al (2011) Nature Structural & Molecular Biology 18: 529-537. Cascade is routinely purified with an N-terminal Strep-tag II fused to CasB (or CasC in CasCDE). Size exclusion chromatography (Superdex 200 HR 10/30 (GE)) is performed using 20 mM Tris-HCl (pH 8.0), 0.1 M NaCl, 1 mM dithiothreitol. Cascade preparations (~0.3 mg) are incubated with DNase I (Invitrogen) in the presence of 2.5 mM $MgCl_2$ for 15 min at 37° C. prior to size exclusion analysis. Co-purified nucleic acids are isolated by extraction using an equal volume of phenol:chloroform:isoamylalcohol (25:24:1) pH 8.0 (Fluka), and incubated with either DNase I (Invitrogen) supplemented with 2.5 mM $MgCl_2$ or RNase A (Fermentas) for 10 min at 37° C. Cas subunit proteins fused to the amino acid sequence of Strep-Tag are produced.

Plaque assays showing the biological activity of the Strep-Tag Cascade subunits are performed using bacteriophage Lambda and the efficiency of plaquing (EOP) was calculated as described in Brouns et al (2008).

For purification of crRNA, samples are analyzed by ion-pair reversed-phased-HPLC on an Agilent 1100 HPLC with $UV_{260\ nm}$ detector (Agilent) using a DNAsep column 50 mm×4.6 mm I. D. (Transgenomic, San Jose, CA). The chromatographic analysis is performed using the following buffer conditions: A) 0.1 M triethylammonium acetate (TEAA) (pH 7.0) (Fluka); B) buffer A with 25% LC MS grade acetonitrile (v/v) (Fisher). crRNA is obtained by injecting purified intact Cascade at 75° C. using a linear gradient starting at 15% buffer B and extending to 60% B in 12.5 min, followed by a linear extension to 100% B over 2 min at a flow rate of 1.0 ml/min. Hydrolysis of the cyclic phosphate terminus was performed by incubating the HPLC-purified crRNA in a final concentration of 0.1 M HCl at 4° C. for 1 hour. The samples are concentrated to 5-10 μl on a vacuum concentrator (Eppendorf) prior to ESI-MS analysis.

Electrospray Ionization Mass spectrometry analysis of crRNA is performed in negative mode using an UHR-TOF mass spectrometer (maXis) or an HCT Ultra PTM Discovery instrument (both Bruker Daltonics), coupled to an online capillary liquid chromatography system (Ultimate 3000, Dionex, UK). RNA separations are performed using a monolithic (PS-DVB) capillary column (200 μm×50 mm I.D., Dionex, UK). The chromatography is performed using the following buffer conditions: C) 0.4 M 1,1,1,3,3,3,-Hexafluoro-2-propanol (HFIP, Sigma-Aldrich) adjusted with triethylamine (TEA) to pH 7.0 and 0.1 mM TEAA, and D) buffer C with 50% methanol (v/v) (Fisher). RNA analysis is performed at 50° C. with 20% buffer D, extending to 40% D in 5 min followed by a linear extension to 60% D over 8 min at a flow rate of 2 μl/min.

Cascade protein is analyzed by native mass spectrometry in 0.15 M ammonium acetate (pH 8.0) at a protein concentration of 5 M. The protein preparation is obtained by five sequential concentration and dilution steps at 4° C. using a centrifugal filter with a cut-off of 10 kDa (Millipore). Proteins are sprayed from borosilicate glass capillaries and analyzed on a LCT electrospray time-of-flight or modified quadrupole time-of-flight instruments (both Waters, UK) adjusted for optimal performance in high mass detection (see Tahallah N et al (2001) Rapid Commun Mass Spectrom 15: 596-601 (2001) and van den Heuvel, R. H. et al. Anal Chem 78: 7473-83 (2006). Exact mass measurements of the individual Cas proteins were acquired under denaturing conditions (50% acetonitrile, 50% MQ, 0.1% formic acid). Sub-complexes in solution were generated by the addition of 2-propanol to the spray solution to a final concentration of 5% (v/v). Instrument settings were as follows; needle voltage ~1.2 kV, cone voltage ~175 V, source pressure 9 mbar. Xenon was used as the collision gas for tandem mass spectrometric analysis at a pressure of 1.5 $10^{-2}$ mbar. The collision voltage varied between 10-200 V.

Electrophoretic mobility shift assays (EMSA) are used to demonstrate the functional activity of Cascade complexes for target nucleic acids. EMSA is performed by incubating Cascade, CasBCDE or CasCDE with 1 nM labelled nucleic acid in 50 mM Tris-Cl pH 7.5, 100 mM NaCl. Salmon sperm DNA (Invitrogen) is used as competitor. EMSA reactions are incubated at 37° C. for 20-30 min prior to electrophoresis on 5% polyacrylamide gels. The gels are dried and analyzed using phosphor storage screens and a PMI phosphor imager (Bio-Rad). Target DNA binding and cleavage activity of Cascade is tested in the presence of 1-10 mM Ca, Mg or Mn-ions.

DNA targets are gel-purified long oligonucleotides (Isogen Life Sciences or Biolegio), listed in Supplementary Table 3 of Jore et al (2011). The oligonucleotides are end-labeled using $\gamma^{32}$P-ATP (PerkinElmer) and T4 kinase (Fermentas). Double-stranded DNA targets are prepared by annealing complementary oligonucleotides and digesting remaining ssDNA with Exonuclease I (Fermentas). Labelled RNA targets are in vitro transcribed using T7 Maxiscript or T7 Mega Shortscript kits (Ambion) with $\alpha^{32}$P-CTP (PerkinElmer) and removing template by DNase I (Fermentas) digestion. Double stranded RNA targets are prepared by annealing complementary RNAs and digesting surplus ssRNA with RNase T1 (Fermentas), followed by phenol extraction.

Plasmid mobility shift assays are performed using plasmid pWUR613 containing the R44 protospacer. The fragment containing the protospacer is PCR-amplified from bacteriophage P7 genomic DNA using primers BG3297 and BG 3298 (see Supplementary Table 3 of Jore et al (2011). Plasmid (0.4 μg) and Cascade were mixed in a 1:10 molar ratio in a buffer containing 5 mM Tris-HCl (pH 7.5) and 20 mM NaCl and incubated at 37° C. for 30 minutes. Cascade proteins were then removed by proteinase K treatment (Fluka) (0.15 U, 15 min, 37° C.) followed by phenol/chloroform extraction. RNA-DNA complexes were then treated with RNaseH (Promega) (2 U, 1 h, 37° C.).

Strep-Tag-Cas protein subunit fusions which form Cascade protein complexes or active sub-complexes with the RNA component (equivalent to a crRNA), have the expected biological and functional activity of scanning and specific attachment and cleavage of nucleic acid targets. Fusions of the Cas subunits with the amino acid chains of fluorescent dyes also form Cascade complexes and sub-complexes with the RNA component (equivalent to crRNA) which retains biological and functional activity and allows visualisation of the location of a target nucleic acid sequence in ds DNA for example.

Example 7—a Cascade-Nuclease Pair and Test of Nuclease Activity In Vitro

Six mutations designated "Sharkey" have been introduced by random mutagenesis and screening to improve nuclease activity and stability of the non-specific nuclease domain from *Flavobacterium okeanokoites* restriction enzyme FokI (see Guo, J., et al. (2010) J. Mol. Biol. 400: 96-107). Other mutations have been introduced that reduce off-target cleavage activity. This is achieved by engineering electrostatic interactions at the FokI dimer interface of a ZFN pair, creating one FokI variant with a positively charged interface (KKR, E490K, I538K, H537R) and another with a negatively charged interface (ELD, Q486E, I499L, N496D) (see Doyon, Y., et al., (2011) Nature Methods 8: 74-9). Each of these variants is catalytically inactive as a homodimer, thereby reducing the frequency of off-target cleavage.

Cascade-Nuclease Design

We translationally fused improved FokI nucleases to the N-terminus of Cse1 to generate variants of Cse1 being FokI$^{KKR}$-Cse1 and FokI$^{ELD}$-Cse1, respectively. These two variants are co-expressed with Cascade subunits (Cse2, Cas7, Cas5 and Cas6e), and one of two distinct CRISPR plasmids with uniform spacers. This loads the Cascade$^{KKR}$ complex with uniform P7-crRNA, and the Cascade$^{ELD}$ complex with uniform M13 g8-crRNA. These complexes are purified using the N-terminally StrepII-tagged Cse2 as described in Jore, M. M., et al., (2011) Nat. Struct. Mol. Biol. 18(5): 529-536. Furthermore an additional purification step can be carried out using an N-terminally HIS-tagged FokI, to ensure purifying full length and intact Cascade-nuclease fusion complexes.

The nucleotide and amino acid sequences of the fusion proteins used in this example were as follows:

```
>nucleotide sequence of FokI-(Sharkey-ELD)-Cse1
                                              [SEQ ID NO: 18]
ATGGCTCAACTGGTTAAAAGCGAACTGGAAGAGAAAAAAAGTGAACTGCGCCACAAACTGAAA

TATGTGCCGCATGAATATATCGAGCTGATTGAAATTGCACGTAATCCGACCCAGGATCGTATT

CTGGAAATGAAAGTGATGGAATTTTTTATGAAAGTGTACGGCTATCGCGGTGAACATCTGGGT

GGTAGCCGTAAACCGGATGGTGCAATTTATACCGTTGGTAGCCCGATTGATTATGGTGTTATT

GTTGATACCAAAGCCTATAGCGGTGGTTATAATCTGCCGATTGGTCAGGCAGATGAAATGGAA

CGTTATGTGGAAGAAAATCAGACCCGTGATAAACATCTGAATCCGAATGAATGGTGGAAAGTT

TATCCGAGCAGCGTTACCGAGTTTAAATTCCTGTTTGTTAGCGGTCACTTCAAAGGCAACTAT

AAAGCACAGCTGACCCGTCTGAATCATATTACCAATTGTAATGGTGCAGTTCTGAGCGTTGAA

GAACTGCTGATTGGTGGTGAAATGATTAAAGCAGGCACCCTGACCCTGGAAGAAGTTCGTCGC

AAATTTAACAATGGCGAAATCAACTTTGCGGATCCCACCAACCGCGCGAAAGGCCTGGAAGCG

GTGAGCGTGGCGAGCatgaatttgcttattgataactggattcctgtacgcccgcgaaacggg

gggaaagtccaaatcataaatctgcaatcgctatactgcagtagagatcagtggcgattaagt

ttgccccgtgacgatatggaactggccgctttagcactgctggtttgcattgggcaaattatc

gccccggcaaaagatgacgttgaatttcgacatcgcataatgaatccgctcactgaagatgag

tttcaacaactcatcgcgccgtggatagatatgttctaccttaatcacgcagaacatccatta

tgcagaccaaaggtgtcaaagcaaatgatgtgactccaatggaaaaactgttggctggggtaa

gcggcgcgacgaattgtgcatttgtcaatcaaccggggcagggtgaagcattatgtggtggat

gcactgcgattgcgttattcaaccaggcgaatcaggcaccaggtfttggtggtggtfttaaaa

gcggtttacgtggaggaacacctgtaacaacgttcgtacgtgggatcgatcttcgttcaacgg

tgttactcaatgtcctcacattacctcgtcttcaaaaacaatttcctaatgaatcacatacgg

aaaaccaacctacctggattaaacctatcaagtccaatgagtctatacctgatcgtcaattgg

gtftgtccgtggtctattctggcaaccagcgcatattgaattatgcgatcccattgggattgg
```

-continued taaatgttatgctgtggacaggaaagcaatttgcgttataccggttftcttaaggaaaaattt acctttacagttaatgggctatggccccatccgcattcccatgtctggtaacagtcaagaaag gggaggttgaggaaaaatttcttgctttcaccacctccgcaccatcatggacacaaatcagcc gagttgtggtagataagattattcaaaatgaaaatggaaatcgcgtggcggcggttgtgaatc aattcagaaatattgcgccgcaaagtcctcttgaattgattatgggggatatcgtaataatc aagcatctattcttgaacggcgtcatgatgtgttgatgtttaatcaggggtggcaacaatacg gcaatgtgataaacgaaatagtgactgttggtttgggatataaaacagccttacgcaaggcgt tatatacctttgcagaagggfttaaaaataaagacttcaaaggggccggagtctctgttcatg agactgcagaaaggcatttctatcgacagagtgaattattaattcccgatgtactggcgaatg ttaatttttcccaggctgatgaggtaatagctgatttacgagacaaacttcatcaattgtgtg aaatgctatttaatcaatctgtagctccctatgcacatcatcctaaattaataagcacattag cgcttgcccgcgccacgctatacaaacatttacgggagttaaaaccgcaaggagggccatcaa atggctga >protein sequence of FokI-(Sharkey-ELD)-Cse1

[SEQ ID NO: 19]

MAQLVKSELEEKKSELRHKLKYVPHEYIELIEIARNPTQDRILEMKVMEFFMKVYGYRGEHLG

GSRKPDGAIYTVGSPIDYGVIVDTKAYSGGYNLPIGQADEMERYVEENQTRDKHLNPNEWWKV

YPSSVTEFKFLFVSGHFKGNYKAQLTRLNHITNCNGAVLSVEELLIGGEMIKAGTLTLEEVRR

KFNNGEINFADPTNRAKGLEAVSVASMNLLIDNWIPVRPRNGGKVQIINLQSLYCSRDQWRLS

LPRDDMELAALALLVCIGQIIAPAKDDVEFRHRIMNPLTEDEFQQLIAPWIDMFYLNHAEHPF

MQTKGVKANDVTPMEKLLAGVSGATNCAFVNQPGQGEALCGGCTAIALFNQANQAPGFGGGFK

SGLRGGTPVTTFVRGIDLRSTVLLNVLTLPRLQKQFPNESHTENQPTWIKPIKSNESIPASSI

GFVRGLFWQPAHIELCDPIGIGKCSCCGQESNLRYTGFLKEKFTFTVNGLWPHPHSPCLVTVK

KGEVEEKFLAFTTSAPSWTQISRVVVDKIIQNENGNRVAAVVNQFRNIAPQSPLELIMGGYRN

NQASILERRHDVLMFNQGWQQYGNVINEIVTVGLGYKTALRKALYTFAEGFKNKDFKGAGVSV

HETAERHFYRQSELLIPDVLANVNFSQADEVIADLRDKLHQLCEMLFNQSVAPYAHHPKLIST

LALARATLYKHLRELKPQGGPSNG*

>nucleotide sequence of FokI-(Sharkey-KKR)-Cse1

[SEQ ID NO: 20]

ATGGCTCAACTGGTTAAAAGCGAACTGGAAGAGAAAAAAAGTGAACTGCGCCACAAACTGAAA

TATGTGCCGCATGAATATATCGAGCTGATTGAAATTGCACGTAATCCGACCCAGGATCGTATT

CTGGAAATGAAAGTGATGGAATTTTTTATGAAAGTGTACGGCTATCGCGGTGAACATCTGGGT

GGTAGCCGTAAACCGGATGGTGCAATTTATACCGTTGGTAGCCCGATTGATTATGGTGTTATT

GTTGATACCAAAGCCTATAGCGGTGGTTATAATCTGCCGATTGGTCAGGCAGATGAAATGCAG

CGTTATGTGAAAGAAAATCAGACCCGCAACAAACATATTAACCCGAATGAATGGTGGAAAGTT

TATCCGAGCAGCGTTACCGAGTTTAAATTCCTGTTTGTTAGCGGTCACTTCAAAGGCAACTAT

AAAGCACAGCTGACCCGTCTGAATCGTAAAACCAATTGTAATGGTGCAGTTCTGAGCGTTGAA

GAACTGCTGATTGGTGGTGAAATGATTAAAGCAGGCACCCTGACCCTGGAAGAAGTTCGTCGC

AAATTTAACAATGGCGAAATCAACTTTGCGGATCCCACCAACCGCGCGAAAGGCCTGGAAGCG

GTGAGCGTGGCGAGCatgaatttgcttattgataactggattcctgtacgcccgcgaaacggg gggaaagtccaaatcataaatctgcaatcgctatactgcagtagagatcagtggcgattaagt ttgccccgtgacgatatggaactggccgctttagcactgctggtttgcattgggcaaattatc -continued gccccggcaaaagatgacgttgaatttcgacatcgcataatgaatccgctcactgaagatgag tttcaacaactcatcgcgccgtggatagatatgttctaccttaatcacgcagaacatccatta tgcagaccaaaggtgtcaaagcaaatgatgtgactccaatggaaaaactgttggctggggtaa gcggcgcgacgaattgtgcatttgtcaatcaaccggggcagggtgaagcattatgtggtggat gcactgcgattgcgttattcaaccaggcgaatcaggcaccaggtttftggtggtggttttaaaa gcggtttacgtggaggaacacctgtaacaacgttcgtacgtgggatcgatcttcgttcaacgg tgttactcaatgtcctcacattacctcgtcttcaaaaacaatttcctaatgaatcacatacgg aaaaccaacctacctggattaaacctatcaagtccaatgagtctatacctgcttcgtcaattg ggtttgtccgtggtctattctggcaaccagcgcatattgaattatgcgatcccattgggattg gtaaatgttcttgctgtggacaggaaagcaatttgcgttataccggttttcttaaggaaaaat ttacctttacagttaatgggctatggccccatccgcattccccttgtctggtaacagtcaaga aaggggaggttgaggaaaaatttcttgctttcaccacctccgcaccatcatggacacaaatca gccgagttgtggtagataagattattcaaaatgaaaatggaaatcgcgtggcggcggttgtga atcaattcagaaatattgcgccgcaaagtcctcttgaattgattatgggggatatcgtaata atcaagcatctattcttgaacggcgtcatgatgtgttgatgtttaatcaggggtggcaacaat acggcaatgtgataaacgaaatagtgactgttggtttgggatataaaacagccttacgcaagg cgttatataccttgcagaagggtttaaaaataaagacttcaaaggggccggagtctctgttc atgagactgcagaaaggcatttctatcgacagagtgaattattaattcccgatgtactggcga atgttaatttttcccaggctgatgaggtaatagctgatttacgagacaaacttcatcaattgt gtgaaatgctatttaatcaatctgtagctccctatgcacatcatcctaaattaataagcacat tagcgcttgcccgcgccacgctatacaaacatttacgggagttaaaaccgcaaggagggccat caaatggctga >protein sequence of FokI-(Sharkey-KKR)-Cse1

[SEQ ID NO: 21]

MAQLVKSELEEKKSELRHKLKYVPHEYIELIEIARNPTQDRILEMKVMEFFMKVYGYRGEHLG

GSRKPDGAIYTVGSPIDYGVIVDTKAYSGGYNLPIGQADEMQRYVKENQTRNKHINPNEWWKV

YPSSVTEFKFLFVSGHFKGNYKAQLTRLNRKTNCNGAVLSVEELLIGGEMIKAGTLTLEEVRR

KFNNGEINFADPTNRAKGLEAVSVASMNLLIDNWIPVRPRNGGKVQIINLQSLYCSRDQWRLS

LPRDDMELAALALLVCIGQIIAPAKDDVEFRHRIMNPLTEDEFQQLIAPWIDMFYLNHAEHPF

MQTKGVKANDVTPMEKLLAGVSGATNCAFVNQPGQGEALCGGCTAIALFNQANQAPGFGGGFK

SGLRGGTPVTTFVRGIDLRSTVLLNVLTLPRLQKQFPNESHTENQPTWIKPIKSNESIPASSI

GFVRGLFWQPAHIELCDPIGIGKCSCCGQESNLRYTGFLKEKFTFTVNGLWPHPHSPCLVTVK

KGEVEEKFLAFTTSAPSWTQISRVVVDKIIQNENGNRVAAVVNQFRNIAPQSPLELEVIGGYR

NNQASILERRHDVLMFNQGWQQYGNVINEIVTVGLGYKTALRKALYTFAEGFKNKDFKGAGVS

VHETAERHFYRQSELLIPDVLANVNFSQADEVIADLRDKLHQLCEMLFNQSVAPYAHHPKLIS

TLALARATLYKHLRELKPQGGPSNG*

>nuclotide sequence of $His_6$-Dual-monopartite NLS
SV40-FokI-(Sharkey-KKR)-Cse1

[SEQ ID NO: 22]

ATGcatcaccatcatcaccac*CCGAAAAAAAAGCGCAAAGTGGATCCGAAGAAAAAACGTAAA*

*GTTGAAG*ATCCGAAAGACATGGCTCAACTGGTTAAAAGCGAACTGGAAGAGAAAAAAAGTGAA

CTGCGCCACAAACTGAAATATGTGCCGCATGAATATATCGAGCTGATTGAAATTGCACGTAAT

CCGACCCAGGATCGTATTCTGGAAATGAAAGTGATGGAATTTTTTATGAAAGTGTACGGCTAT

-continued

CGCGGTGAACATCTGGGTGGTAGCCGTAAACCGGATGGTGCAATTTATACCGTTGGTAGCCCG

ATTGATTATGGTGTTATTGTTGATACCAAAGCCTATAGCGGTGGTTATAATCTGCCGATTGGT

CAGGCAGATGAAATGCAGCGTTATGTGAAAGAAAATCAGACCCGCAACAAACATATTAACCCG

AATGAATGGTGGAAAGTTTATCCGAGCAGCGTTACCGAGTTTAAATTCCTGTTTGTTAGCGGT

CACTTCAAAGGCAACTATAAAGCACAGCTGACCCGTCTGAATCGTAAAACCAATTGTAATGGT

GCAGTTCTGAGCGTTGAAGAACTGCTGATTGGTGGTGAAATGATTAAAGCAGGCACCCTGACC

CTGGAAGAAGTTCGTCGCAAATTTAACAATGGCGAAATCAACTTTGCGGATCCCACCAACCGC

GCGAAAGGCCTGGAAGCGGTGAGCGTGGCGAGCatgaatttgcttattgataactggattcct gtacgcccgcgaaacggggggaaagtccaaatcataaatctgcaatcgctatactgcagtaga gatcagtggcgattaagtttgccccgtgacgatatggaactggccgctttagcactgctggtt tgcattgggcaaattatcgccccggcaaaagatgacgttgaatttcgacatcgcataatgaat ccgctcactgaagatgagtttcaacaactcatcgcgccgtggatagatatgttctaccttaat cacgcagaacatccctttatgcagaccaaaggtgtcaaagcaaatgatgtgactccaatggaa aaactgttggctggggtaagcggcgcgacgaattgtgcatttgtcaatcaaccggggcagggt gaagcattatgtggtggatgcactgcgattgcgttattcaaccaggcgaatcaggcaccaggt tttggtggtggttttaaaagcggtttacgtggaggaacacctgtaacaacgttcgtacgtggg atcgatcttcgttcaacggtgttactcaatgtcctcacattacctcgtcttcaaaaacaattt cctaatgaatcacatacggaaaaccaacctacctggattaaacctatcaagtccaatgagtct atacctgcttcgtcaattgggtttgtccgtggtctattctggcaaccagcgcatattgaatta tgcgatcccattgggattggtaaatgttcttgctgtggacaggaaagcaatttgcgttatacc ggttftcttaaggaaaaatttacctttacagttaatgggctatggccccatccgcattcccct tgtctggtaacagtcaagaaaggggaggttgaggaaaaatttcttgctttcaccacctccgca ccatcatggacacaaatcagccgagttgtggtagataagattattcaaaatgaaaatggaaat cgcgtggcggcggttgtgaatcaattcagaaatattgcgccgcaaagtcctcttgaattgatt atggggggatatcgtaataatcaagcatctattatgaacggcgtcatgatgtgttgatgttta atcaggggtggcaacaatacggcaatgtgataaacgaaatagtgactgttggtttgggatata aaacagccttacgcaaggcgttatataccttgcagaagggtttaaaaataaagacttcaaag gggccggagtctctgttcatgagactgcagaaaggcatttctatcgacagagtgaattattaa ttcccgatgtactggcgaatgttaatttttcccaggctgatgaggtaatagctgatttacgag acaaacttcatcaattgtgtgaaatgctatttaatcaatctgtagctccctatgcacatcatc ctaaattaataagcacattagcgcttgcccgcgccacgctatacaaacatttacgggagttaa aaccgcaaggagggccatcaaatggctga >protein sequence of $His_6$-Dual-monopartite NLS
SV40-FokI-(Sharkey-KKR)-Cse1

[SEQ ID NO: 23]

MHHHHHHPKKKRKVDPKKKRKVEDPKDMAQLVKSELEEKKSELRHKLKYVPHEYIELIEIARN

PTQDRILEMKVMEFFMKVYGYRGEHLGGSRKPDGAIYTVGSPIDYGVIVDTKAYSGGYNLPIG

QADEMQRYVKENQTRNKHINPNEWWKVYPSSVTEFKFLFVSGHFKGNYKAQLTRLNRKTNCNG

AVLSVEELLIGGEMIKAGTLTLEEVRRKFNNGEINFADPTNRAKGLEAVSVASMNLLIDNWIP

VRPRNGGKVQIINLQSLYCSRDQWRLSLPRDDMELAALALLVCIGQIIAPAKDDVEFRHRIMN

PLTEDEFQQLIAPWIDMFYLNHAEHPFMQTKGVKANDVTPMEKLLAGVSGATNCAFVNQPGQG

EALCGGCTAIALFNQANQAPGFGGGFKSGLRGGTPVTTFVRGIDLRSTVLLNVLTLPRLQKQF

-continued

PNESHTENQPTWIKPIKSNESIPASSIGFVRGLFWQPAHIELCDPIGIGKCSCCGQESNLRYT

GFLKEKFTFTVNGLWPHPHSPCLVTVKKGEVEEKFLAFTTSAPSWTQISRVVVDKIIQNENGN

RVAAVVNQFRNIAPQSPLELIMGGYRNNQASILERRHDVLMFNQGWQQYGNVINEIVTVGLGY

KTALRKALYTFAEGFKNKDFKGAGVSVHETAERHFYRQSELLIPDVLANVNFSQADEVIADLR

DKLHQLCEMLFNQSVAPYAHHPKLISTLALARATLYKHLRELKPQGGPSNG*

>nucleotide sequence of $His_6$-Dual-monopartite NLS SV40-FokI (Sharkey-ELD)-Cse1

[SEQ ID NO: 24]

ATGcatcaccatcatcaccac*CCGAAAAAAAAGCGCAAAGTGGATCCGAAGAAAAAACGTAAA*

*GTTGAAGATCCGAAAGAC*ATGGCTCAACTGGTTAAAAGCGAACTGGAAGAGAAAAAAAGTGAA

CTGCGCCACAAACTGAAATATGTGCCGCATGAATATATCGAGCTGATTGAAATTGCACGTAAT

CCGACCCAGGATCGTATTCTGGAAATGAAAGTGATGGAATTTTTTATGAAAGTGTACGGCTAT

CGCGGTGAACATCTGGGTGGTAGCCGTAAACCGGATGGTGCAATTTATACCGTTGGTAGCCCG

ATTGATTATGGTGTTATTGTTGATACCAAAGCCTATAGCGGTGGTTATAATCTGCCGATTGGT

CAGGCAGATGAAATGGAACGTTATGTGGAAGAAAATCAGACCCGTGATAAACATCTGAATCCG

AATGAATGGTGGAAAGTTTATCCGAGCAGCGTTACCGAGTTTAAATTCCTGTTTGTTAGCGGT

CACTTCAAAGGCAACTATAAAGCACAGCTGACCCGTCTGAATCATATTACCAATTGTAATGGT

GCAGTTCTGAGCGTTGAAGAACTGCTGATTGGTGGTGAAATGATTAAAGCAGGCACCCTGACC

CTGGAAGAAGTTCGTCGCAAATTTAACAATGGCGAAATCAACTTTGCGGATCCCACCAACCGC

GCGAAAGGCCTGGAAGCGGTGAGCGTGGCGAGCatgaatttgcttattgataactggattcct gtacgcccgcgaaacgggggggaaagtccaaatcataaatctgcaatcgctatactgcagtaga gatcagtggcgattaagtttgccccgtgacgatatggaactggccgctttagcactgctggtt tgcattgggcaaattatcgccccggcaaaagatgacgttgaatttcgacatcgcataatgaat ccgctcactgaagatgagtttcaacaactcatcgcgccgtggatagatatgttctaccttaat cacgcagaacatccctttatgcagaccaaaggtgtcaaagcaaatgatgtgactccaatggaa aaactgttggctggggtaagcggcgcgacgaattgtgcatttgtcaatcaaccggggcagggt gaagcattatgtggtggatgcactgcgattgcgttattcaaccaggcgaatcaggcaccaggt tttggtggtggttttaaaagcggtttacgtggaggaacacctgtaacaacgttcgtacgtggg atcgatcttcgttcaacggtgttactcaatgtcctcacattacctcgtcttcaaaaacaattt cctaatgaatcacatacggaaaaccaacctacctggattaaacctatcaagtccaatgagtct atacctgcttcgtcaattgggtttgtccgtggtctattctggcaaccagcgcatattgaatta tgcgatcccattgggattggtaaatgttcttgctgtggacaggaaagcaatttgcgttatacc ggttttcttaaggaaaaatttacctttacagttaatgggctatggccccatccgcattcccct tgtctggtaacagtcaagaaaggggaggttgaggaaaaatttcttgctttcaccacctccgca ccatcatggacacaaatcagccgagttgtggtagataagattattcaaaatgaaaatggaaat cgcgtggcggcggttgtgaatcaattcagaaatattgcgccgcaaagtcctcttgaattgatt atggggggatatcgtaataatcaagcatctattcttgaacggcgtcatgatgtgttgatgttt aatcaggggtggcaacaatacggcaatgtgataaacgaaatagtgactgttggtttgggatat aaaacagccttacgcaaggcgttatatacctttgcagaagggtttaaaaataaagacttcaaa ggggccggagtctctgttcatgagactgcagaaaggcatttctatcgacagagtgaattatta attcccgatgtactggcgaatgttaatttttcccaggctgatgaggtaatagctgatttacga gacaaacttcatcaattgtgtgaaatgctatttaatcaatctgtagctccctatgcacatcat -continued cctaaattaataagcacattagcgcttgcccgcgccacgctatacaaacatttacgggagtta aaaccgcaaggagggccatcaaatggctga >protein sequence of His$_6$-Dual-monopartite NLS
SV40-FokI(Sharkey-ELD)-Cse1

[SEQ ID NO: 25]

MHHHHHHPKKKRKVDPKKKRKVEDPKDMAQLVKSELEEKKSELRHKLKYVPHEYIELIEIARN

PTQDRILEMKVMEFFMKVYGYRGEHLGGSRKPDGAIYTVGSPIDYGVIVDTKAYSGGYNLPIG

QADEMERYVEENQTRDKHLNPNEWWKVYPSSVTEFKFLFVSGHFKGNYKAQLTRLNHITNCNG

AVLSVEELLIGGEMIKAGTLTLEEVRRKFNNGEINFADPTNRAKGLEAVSVASMNLLIDNWIP

VRPRNGGKVQIINLQSLYCSRDQWRLSLPRDDMELAALALLVCIGQIIAPAKDDVEFRHRIMN

PLTEDEFQQLIAPWIDMFYLNHAEHPFMQTKGVKANDVTPMEKLLAGVSGATNCAFVNQPGQG

EALCGGCTAIALFNQANQAPGFGGGFKSGLRGGTPVTTFVRGIDLRSTVLLNVLTLPRLQKQF

PNESHTENQPTWIKPIKSNESIPASSIGFVRGLFWQPAHIELCDPIGIGKCSCCGQESNLRYT

GFLKEKFTFTVNGLWPHPHSPCLVTVKKGEVEEKFLAFTTSAPSWTQISRVVVDKIIQNENGN

RVAAVVNQFRNIAPQSPLELIMGGYRNNQASILERRHDVLMFNQGWQQYGNVINEIVTVGLGY

KTALRKALYTFAEGFKNKDFKGAGVSVHETAERHFYRQSELLIPDVLANVNFSQADEVIADL

RDKLHQLCEMLFNQSVAPYAHHPKLISTLALARATLYKHLRELKPQGGPSNG*

DNA Cleavage Assay

The specificity and activity of the complexes was tested using an artificially constructed target plasmid as a substrate. This plasmid contains M13 and P7 binding sites on opposing strands such that both FokI domains face each other (see FIG. 11). The distance between the Cascade binding sites varies between 25 and 50 basepairs with 5 bp increments. As the binding sites of Cascade need to be flanked by any of four known PAM sequences (5'-protospacer-CTT/CAT/CTC/CCT-3' this distance range gives sufficient flexibility to design such a pair for almost any given sequence.

The sequences of the target plasmids used are as follows. The number indicated the distance between the M13 and P7 target sites. Protospacers are shown in bold, PAMs underlined:

Sequences of the target plasmids. The number indicates the distance between the M13 and P7 target sites. (protospacers in bold, PAMs underlined)

>50 bp

[SEQ ID NO: 26]

gaattcACAACGGTGAGCAAGTCACTGTTGGCAAGCCAGGATCTGAACAA

TACCGTCTTGCTTTCGAGCGCTAGCTCTAGAACTAGTCCTCAGCCTAGGC

CTCGTTCCGAAGCTGTCTTTCGCTGCTGAGGGTGACGATCCCGCATAGGC

GGCCTTTAACTCggatcc

>45 bp

[SEQ ID NO: 27]

gaattcACAACGGTGAGCAAGTCACTGTTGGCAAGCCAGGATCTGAACAA

TACCGTCTTTTCGAGCGCTAGCTCTAGAACTAGTCCTCAGCCTAGGCCTC

GTTCAAGCTGTCTTTCGCTGCTGAGGGTGACGATCCCGCATAGGCGGCCT

TTAACTCggatcc

-continued

>40 bp

[SEQ ID NO: 28]

gaattcACAACGGTGAGCAAGTCACTGTTGGCAAGCCAGGATCTGAACAA

TACCGTCTTCGAGCGCTAGCTCTAGAACTAGTCCTCAGCCTAGGCCTCGA

AGCTGTCTTTCGCTGCTGAGGGTGACGATCCCGCATAGGCGGCCTTTAAC

TCggatcc

>35 bp

[SEQ ID NO: 29]

gaattcACAACGGTGAGCAAGTCACTGTTGGCAAGCCAGGATCTGAACAA

TACCGTCTTGCGCTAGCTCTAGAACTAGTCCTCAGCCTAGGCCTAAGCTG

TCTTTCGCTGCTGAGGGTGACGATCCCGCATAGGCGGCCTTTAACTCgga tcc

>30 bp

[SEQ ID NO: 30]

gaattcACAACGGTGAGCAAGTCACTGTTGGCAAGCCAGGATCTGAACAA

TACCGTCTTGCTAGCTCTAGAACTAGTCCTCAGCCTAGGAAGCTGTCTTT

CGCTGCTGAGGGTGACGATCCCGCATAGGCGGCCTTTAACTCggatcc

>25 bp

[SEQ ID NO: 31]

gaattcACAACGGTGAGCAAGTCACTGTTGGCAAGCCAGGATCTGAACAA

TACCGTCTTCTCTAGAACTAGTCCTCAGCCTAGGAAGCTGTCTTTCGCTG

CTGAGGGTGACGATCCCGCATAGGCGGCCTTTAACTCggatcc

Cleavage of the target plasmids was analysed on agarose gels, where negatively supercoiled (nSC) plasmid can be distinguished from linearized- or nicked plasmid. The cleavage site of the Cascade$^{KKR/ELD}$ pair in a target vector was determined by isolating linear cleavage products from an agarose gel and filling in the recessed 3' ends left by FokI cleavage with the Klenow fragment of *E. coli* DNA polymerase to create blunt ends. The linear vector was self-ligated, transformed, amplified, isolated and sequenced. Filling in of recessed 3' ends and re-ligation will lead to extra nucleotides in the sequence that represents the overhang left by FokI cleavage. By aligning the sequence reads to the original sequence, the cleavage sites can be found on a clonal level and mapped. Below, the additional bases incorporated into the sequence after filling in recessed 3' ends left by FokI cleavage are underlined:

FokI cleavage

5' CTTGCGCTAGCTCTAGAA CTAGTCCTCAGCCTAGGCCTAA

G 3'

3' GAACGCGATCGAGATCTTGATC AGGAGTCGGATCCGGATT

C 5'

3' fill in, ligation

5' CTTGCGCTAGCTCTAGAACTAG - CTAGTCCTCAGCCTAGGCCTAA

G 3'

3' GAACGCGATCGAGATCTTGATC - GATCAGGAGTCGGATCCGGATT

C 5'

Reading from top to bottom, the 5'-3' sequences above are SEQ ID NOs: 32-35, respectively.

Cleavage of a Target Locus in Human Cells

The human CCR5 gene encodes the C—C chemokine receptor type 5 protein, which serves as the receptor for the human immunodeficiency virus (HIV) on the surface of white blood cells. The CCR5 gene is targeted using a pair of Cascade$^{KKR/ELD}$ nucleases in addition to an artificial GFP locus. A suitable binding site pair is selected on the coding region of CCR5. Two separate CRISPR arrays containing uniform spacers targeting each of the binding sites are constructed using DNA synthesis (Geneart).

The human CCR5 target gene selection and CRISPR designs used are as follows:

>Part of genomic human CCR5 sequence, containing whole ORF (position 347-1446).

[SEQ ID NO: 36]

GGTGGAACAAGATGGATTATCAAGTGTCAAGTCCAATCTATGACATCAAT

TATTATACATCGGAGCCCTGCCAAAAAATCAATGTGAAGCAAATCGCAGC

CCGCCTCCTGCCTCCGCTCTACTCACTGGTGTTCATCTTTGGTTTTGTGG

GCAACATGCTGGTCATCCTCATCCTGATAAACTGCAAAAGGCTGAAGAGC

ATGACTGACATCTACCTGCTCAACCTGGCCATCTCTGACCTGTTTTTCCT

TCTTACTGTCCCCTTCTGGGCTCACTATGCTGCCGCCCAGTGGGACTTTG

GAAATACAATGTGTCAACTCTTGACAGGGCTCTATTTTATAGGCTTCTTC

TCTGGAATCTTCTTCATCATCCTCCTGACAATCGATAGGTACCTGGCTGT

CGTCCATGCTGTGTTTGCTTTAAAAGCCAGGACGGTCACCTTTGGGGTGG

TGACAAGTGTGATCACTTGGGTGGTGGCTGTGTTTGCGTCTCTCCCAGGA

ATCATCTTTACCAGATCTCAAAAAGAAGGTCTTCATTACACCTGCAGCTC

TCATTTTCCATACAGTCAGTATCAATTCTGGAAGAATTTCCAGACATTAA

AGATAGTCATCTTGGGGCTGGTCCTGCCGCTGCTTGTCATGGTCATCTGC

TACTCGGGAATCCTAAAAACTCTGCTTCGGTGTCGAAATGAGAAGAAGAG

GCACAGGGCTGTGAGGCTTATCTTCACCATCATGATTGTTTATTTTCTCT

TCTGGGCTCCCTACAACATTGTCCTTCTCCTGAACACCTTCCAGGAATTC

-continued

TTTGGCCTGAATAATTGCAGTAGCTCTAACAGGTTGGACCAAGCTATGCA

GGTGACAGAGACTCTTGGGATGACGCACTGCTGCATCAACCCCATCATCT

ATGCCTTTGTCGGGGAGAAGTTCAGAAACTACCTCTTAGTCTTCTTCCAA

AAGCACATTGCCAAACGCTTCTGCAAATGCTGTTCTATTTTCCAGCAAGA

GGCTCCCGAGCGAGCAAGCTCAGTTTACACCCGATCCACTGGGGAGCAGG

AAATATCTGTGGGCTTGTGACACGGACTCAAGTGGGCTGGTGACCCAGTC

Red1/2: chosen target sites (distance: 34 bp, PAM 5'-CTT-3'). “Red 1 is first appearing underlined sequence in the above. Red2 is the second underlined sequence.

>CRISPR array red1 (italics = spacers, bold = repeats)

[SEQ ID NO: 37]

ccatggTAATACGACTCACTATAGGGAGAATTAGCTGATCTTTAATAATA

AGGAAATGTTACATTAAGGTTGGTGGGTTGTTTTTATGGGAAAAAATGCT

TTAAGAACAAATGTATACTTTTAGAGAGTTCCCCGCGCCAGCGGGGATAA

ACCG*CAAACACAGCATGGACGACAGCCAGGTACCTA*GAGTTCCCCGCGCC

AGCGGGGATAAACCG*CAAACACAGCATGGACGACAGCCAGGTACCTA*GAG

TTCCCCGCGCCAGCGGGGATAAACCG*CAAACACAGCATGGACGACAGCCA*

*GGTACCTA*GAGTTCCCCGCGCCAGCGGGGATAAACCGAAAACAAAAGGCT

CAGTCGGAAGACTGGGCCTTTTGTTTTAACCCCTTGGGGCCTCTAAACGG

GTCTTGAGGGGTTTTTTGggtacc

>CRISPR array red2 (italics: spacers, bold: repeats)

[SEQ ID NO: 38]

ccatggTAATACGACTCACTATAGGGAGAATTAGCTGATCTTTAATAATA

AGGAAATGTTACATTAAGGTTGGTGGGTTGTTTTTATGGGAAAAAATGCT

TTAAGAACAAATGTATACTTTTAGAGAGTTCCCCGCGCCAGCGGGGATAA

ACCG*TGTGATCACTTGGGTGGTGGCTGTGTTTGCGT*GAGTTCCCCGCGCC

AGCGGGGATAAACCG*TGTGATCACTTGGGTGGTGGCTGTGTTTGCGT*GAG

TTCCCCGCGCCAGCGGGGATAAACCG*TGTGATCACTTGGGTGGTGGCTGT*

*GTTTGCGT*GAGTTCCCCGCGCCAGCGGGGATAAACCGAAAACAAAAGGCT

CAGTCGGAAGACTGGGCCTTTTGTTTTAACCCCTTGGGGCCTCTAAACGG

GTCTTGAGGGGTTTTTTGggtacc

Delivery of Cascade$^{KKR/ELD}$ into the Nucleus of Human Cells

Cascade is very stable as a multi-subunit protein-RNA complex and is easily produced in mg quantities in *E. coli*. Transfection or micro-injection of the complex in its intact form as purified from *E. coli* is used as methods of delivery (see FIG. 12). As shown in FIG. 12, Cascade-FokI nucleases are purified from *E. coli* and encapsulated in protein transfection vesicles. These are then fused with the cell membrane of human HepG2 cells releasing the nucleases in the cytoplasm (step 2). NLS sequences are then be recognized by importin proteins, which facilitate nucleopore passage (step 3). Cascade$^{KKR}$ (open rectangle) and Cascade$^{ELD}$. (filled rectangle) will then find and cleave their target site (step 4.), inducing DNA repair pathways that will alter the target site leading to desired changes. Cascade$^{KKR/ELD}$ nucleases need to act only once and require no permanent presence in the cell encoded on DNA.

To deliver Cascade into human cells, protein transfection reagents are used from various sources including Pierce, NEB, Fermentas and Clontech. These reagents have recently been developed for the delivery of antibodies, and are useful to transfect a broad range of human cell lines with efficiencies up to 90%. Human HepG2 cells are transfected. Also, other cell lines including CHO-K1, COS-7, HeLa, and non-embryonic stem cells, are transfected.

To import the Cascade$^{KKR/ELD}$ nuclease pair into the nucleus, a tandem monopartite nuclear localisation signal (NLS) from the large T-antigen of simian virus 40 (SV40) is fused to the N-terminus of FokI. This ensures import of only intact Cascade$^{ELD/KKR}$ into the nucleus. (The nuclear pore complex translocates RNA polymerases (550 kDa) and other large protein complexes). As a check prior to transformations, the nuclease activity of the Cascade$^{KKR/ELD}$ nuclease pair is checked in vitro using purified complexes and CCR5 PCR amplicons to exclude transfecting non-productive Cascade$^{KKR/ELD}$ nuclease pairs.

Surveyor Assay

Transfected cells are cultivated and passaged for several days. The efficiency of in vivo target DNA cleavage is then assessed by using the Surveyor assay of Guschin, D. Y., et al (2010) Methods Mol. Biol., 649: 247-256. Briefly, PCR amplicons of the target DNA locus will be mixed 1:1 with PCR amplicons from untreated cells. These are heated and allowed to anneal, giving rise to mismatches at target sites that have been erroneously repaired by NHEJ. A mismatch nuclease is then used to cleave only mismatched DNA molecules, giving a maximum of 50% of cleavage when target DNA cleavage by Cascade$^{KKR/ELD}$ is complete. This procedure was then followed up by sequencing of the target DNA amplicons of treated cells. The assay allows for rapid assessment and optimization of the delivery procedure.

Production of Cascade-Nuclease Pairs

The Cascade-nuclease complexes were constructed as explained above. Affinity purification from *E. coli* using the StrepII-tagged Cse2 subunit yields a complex with the expected stoichiometry when compared to native Cascade. Referring to FIG. 13, this shows the stoichiometry of native Cascade (1), Cascade$^{KKR}$ with P7 CrRNA and Cascade$^{ELD}$ with M13 CrRNA 24 h after purification using only Strep-tactin. Bands in native Cascade (1) are from top to bottom: Cse1, Cas7, Cas5, Cas6e, Cse2. Cascade$^{KKR/ELD}$ show the FokI-Cse1 fusion band and an additional band representing Cse1 with a small part of FokI as a result of proteolytic degradation.

Apart from an intact FokI-Cse1 fusion protein, we observed that a fraction of the FokI-Cse1-fusion protein is proteolytically cleaved, resulting in a Cse1 protein with only the linker and a small part of FokI attached to it (as confirmed by Mass Spectrometry, data not shown). In most protein isolations the fraction of degraded fusion protein is approximately 40%. The isolated protein is stably stored in the elution buffer (20 mM HEPES pH 7.5, 75 mM NaCl, 1 mM DTT, 4 mM desthiobiotin) with additional 0.1% Tween 20 and 50% glycerol at −20° C. Under these storage conditions, integrity and activity of the complex have been found stable for at least three weeks (data not shown).

Introduction of a His$_6$-Tag and NLS to the Cascade-Nuclease

The Cascade nuclease fusion design was modified to incorporate a Nucleolar Localization Signal (NLS) to enable transport into the nucleus of eukaryotic cells. For this a tandem monopartite NLS from the large T-antigen of Simian Virus SV40 (sequence: PKKKRKVDPKKKRKV) was translationally fused to the N-terminus of the FokI-Cse1 fusion protein, directly preceded by a His$_6$-tag at the N-terminus. The His$_6$-tag (sequence: MHHHHHH) allows for an additional $Ni^{2+}$-resin affinity purification step after StrepII purification. This additional step ensures the isolation of only full-length Cascade-nuclease fusion complex, and increases the efficiency of cleavage by eliminating the binding of non-intact Cascade complexes to the target site forming an unproductive nuclease pair.

In Vitro Cleavage Assay

Cascade$^{KKR/ELD}$ activity and specificity was assayed in vitro as described above. FIG. 14A shows plasmids with distances between protospacers of 25-50 bp (5 bp increments, lanes 1-6) incubated with Cascade$^{KKR/ELD}$ for 30 minutes at 37° C. Lane 10 contains the target plasmid in its three possible topologies: the lowest band represents the initial, negatively supercoiled (nSC) form of the plasmid, the middle band represents the linearized form (cleaved by XbaI), whilst the upper band represents the open circular (OC) form (after nicking with Nt.BbrCI).

Lane 7 shows incubation of a plasmid with both binding sites removed (negative control). Therefore FIG. 14A shows a typical cleavage assay using various target plasmids in which the binding sites are separated by 25 to 50 base pairs in 5 bp increments (lanes 1 to 6). These plasmids with distances of 25-50 bp were incubated with Cascade$^{KKR/ELD}$ carrying anti P7 and M13 crRNA respectively. A plasmid containing no binding sites served as a control (lane 7). The original plasmid exists in negatively supercoiled form (nSC, control lane 8), and nicked or linearized products are clearly distinguishable. Upon incubation a linear cleavage product is formed when binding sites were separated by 30, 35 and 40 base pairs (lanes 2, 3, 4). At 25, 45 and 50 base pairs distance (lanes 1, 5, 6), the target plasmid appeared to be incompletely cleaved leading to the nicked form (OC). These results show the best cleavage in plasmids with distances between 30 and 40 bp, giving sufficient flexibility when designing a crRNA pair for any given locus. Both shorter and longer distances result in increased nicking activity while creating less DSBs. There is very little activity on a plasmid where the two protospacers have been removed, showing target specificity (lane 7).

Cleavage Conditions

To assess the optimal buffer conditions for cleavage assays, and to estimate whether activity of the complex is expected at physiological conditions, the following two buffers were selected: (1) NEB4 (New England Biolabs, 50 mM potassium acetate, 20 mM Tris-acetate, 10 mM magnesium acetate, 1 mM dithiothreitol, pH 7.9) and (2) Buffer O (Fermentas, 50 mM Tris-HCl, 10 mM $MgCl_2$, 100 mM NaCl, 0.1 mg/mL BSA, pH 7.5). Of the two, NEB4 is recommended for optimal activity of the commercial intact FokI enzyme. Buffer O was chosen from a quick screen to give good activity and specificity (data not shown). FIG. 14B shows incubation with different buffers and different incubation times. Lanes 1-4 have been incubated with Fermentas Buffer O (lane 1, 2 for 15 minutes, lane 3, 4 for 30 minutes), lanes 5, 6 have been incubated with NEB4 (30 minutes). Lanes 1, 3, 5 used the target plasmid with 35 bp spacing, lanes 2, 4, 6 used the non-target plasmid (no binding sites). Lanes 7, 8 have been incubated with only Cascade$^{KKR}$ or Cascade$^{ELD}$ respectively (buffer O). Lane 9 is the topology marker as in (A). Lane 10 and 11 show the target and non-target plasmid incubated without addition of Cascade. Therefore in FIG. 14B, activity was tested on the target plasmid with 35 base pairs distance (lane 1, 3, 5) and a non-target control plasmid (lane 2, 4, 6). There was a high amount of unspecific nicking and less cleavage in NEB4

(lane 5,6), whilst buffer O shows only activity in the target plasmid with a high amount of specific cleavage and little nicking (lane 1-4). The difference is likely caused by the NaCl concentration in buffer O, higher ionic strength weakens protein-protein interactions, leading to less nonspecific activity. Incubation of 15 or 30 minutes shows little difference in both target and non-target plasmid (lane 1,2 or 3,4 respectively). Addition of only one type of Cascade (P7$^{KKR}$ or M13$^{ELD}$) does not result in cleavage activity (lane 7, 8) as expected. This experiment shows that specific Cascade nuclease activity by a designed pair occurs when the NaCl concentration is at least 100 mM, which is near the physiological saline concentration inside cells (137 mM NaCl). The Cascade nuclease pair is expected to be fully active in vivo, in eukaryotic cells, while displaying negligible off-target cleavage activity.

Cleavage Site

The site of cleavage in the target plasmid with a spacing of 35 bp (pTarget35) was determined. FIG. 15 shows how sequencing reveals up- and downstream cleavage sites by Cascade$^{KKR/ELD}$ in the target plasmid with 35 base pair spacing. In FIG. 15A is shown the target region within pTarget35 with annotated potential cleavage sites. Parts of the protospacers are indicated in grey, with the upstream protospacer on the left side and the downstream protospacer on the right side of FIG. 15A. FIG. 15B shows a bar chart of four different cleavage patterns and their relative abundance within sequenced clones. The grey bars represent the generated overhang, while the left and right border of each bar represents the left and right cleavage site (see FIG. 15B for annotation).

FIG. 15A shows the original sequence of pTarget35, with numbered cleavage sites from −7 to +7 where 0 lies in the middle between the two protospacers (indicated in grey). Seventeen clones were sequenced and these all show cleavage around position 0, creating varying overhangs between 3 and 5 bp (see FIG. 15B). Overhangs of 4 are most abundant (cumulatively 88%), while overhangs of 3 and 5 occur only once (6% each). The cleavage occurred exactly as expected with no clones showing off target cleavage.

Cleaving a Target Locus in Human Cells.

Cascade$^{KKR/ELD}$ nucleases were successfully modified to contain an N-terminal $His_6$-tag followed by a dual monopartite Nucleolar Localisation Signal. These modified Cascade nuclease fusion proteins were co-expressed with either one of two synthetically constructed CRISPR arrays, each targeting a binding site in the human CCR5 gene. First the activity of this new nuclease pair is validated in vitro by testing the activity on a plasmid containing this region of the CCR5 gene. The nuclease pair is transfected to a human cell line, e.g. HeLa cell line. Efficiency of target cleavage is assessed using the Surveyor assay as described above.

SEQUENCE LISTING

```
Sequence total quantity: 50
SEQ ID NO: 1            moltype = AA  length = 502
FEATURE                 Location/Qualifiers
source                  1..502
                        mol_type = protein
                        organism = Escherichia coli
SEQUENCE: 1
MNLLIDNWIP VRPRNGGKVQ IINLQSLYCS RDQWRLSLPR DDMELAALAL LVCIGQIIAP  60
AKDDVEFRHR IMNPLTEDEF QQLIAPWIDM FYLNHAEHPF MQTKGVKAND VTPMEKLLAG  120
VSGATNCAFV NQPGQGEALC GGCTAIALFN QANQAPGFGG GFKSGLRGGT PVTTFVRGID  180
LRSTVLLNVL TLPRLQKQFP NESHTENQPT WIKPIKSNES IPASSIGFVR GLFWQPAHIE  240
LCDPIGIGKC SCCGQESNLR YTGFLKEKFT FTVNGLWPHP HSPCLVTVKK GEVEEKFLAF  300
TTSAPSWTQI SRVVVDKIIQ NENGNRVAAV VNQFRNIAPQ SPLELIMGGY RNNQASILER  360
RHDVLMFNQG WQQYGNVINE IVTVGLGYKT ALRKALYTFA EGFKNKDFKG AGVSVHETAE  420
RHFYRQSELL IPDVLANVNF SQADEVIADL RDKLHQLCEM LFNQSVAPYA HHPKLISTLA  480
LARATLYKHL RELKPQGGPS NG                                          502

SEQ ID NO: 2            moltype = AA  length = 160
FEATURE                 Location/Qualifiers
source                  1..160
                        mol_type = protein
                        organism = Escherichia coli
SEQUENCE: 2
MADEIDAMAL YRAWQQLDNG SCAQIRRVSE PDELRDIPAF YRLVQPFGWE NPRHQQALLR  60
MVFCLSAGKN VIRHQDKKSE QTTGISLGRA LANSGRINER RIFQLIRADR TADMVQLRRL  120
LTHAEPVLDW PLMARMLTWW GKRERQQLLE DFVLTTNKNA                        160

SEQ ID NO: 3            moltype = AA  length = 363
FEATURE                 Location/Qualifiers
source                  1..363
                        mol_type = protein
                        organism = Escherichia coli
SEQUENCE: 3
MSNFINIHVL ISHSPSCLNR DDMNMQKDAI FGGKRRVRIS SQSLKRAMRK SGYYAQNIGE  60
SSLRTIHLAQ LRDVLRQKLG ERFDQKIIDK TLALLSGKSV DEAEKISADA VTPWVVGEIA  120
WFCEQVAKAE ADNLDDKKLL KVLKEDIAAI RVNLQQGVDI ALSGRMATSG MMTELGKVDG  180
AMSIAHAITT HQVDSDIDWF TAVDDLQEQG SAHLGTQEFS SGVFYRYANI NLAQLQENLG  240
GASREQALEI ATHVVHMLAT EVPGAKQRTY AAFNPADMVM VNFSDMPLSM ANAFEKAVKA  300
KDGFLQPSIQ AFNQYWDRVA NGYGLNGAAA QFSLSDVDPI TAQVKQMPTL EQLKSWVRNN  360
GEA                                                               363

SEQ ID NO: 4            moltype = AA  length = 224
FEATURE                 Location/Qualifiers
source                  1..224
                        mol_type = protein
```

```
                          organism = Escherichia coli
SEQUENCE: 4
MRSYLILRLA GPMQAWGQPT FEGTRPTGRF PTRSGLLGLL GACLGIQRDD TSSLQALSES  60
VQFAVRCDEL ILDDRRVSVT GLRDYHTVLG AREDYRGLKS HETIQTWREY LCDASFTVAL  120
WLTPHATMVI SELEKAVLKP RYTPYLGRRS CPLTHPLFLG TCQASDPQKA LLNYEPVGGD  180
IYSEESVTGH HLKFTARDEP MITLPRQFAS REWYVIKGGM DVSQ                  224

SEQ ID NO: 5              moltype = AA  length = 199
FEATURE                   Location/Qualifiers
source                    1..199
                          mol_type = protein
                          organism = Escherichia coli
SEQUENCE: 5
MYLSKVIIAR AWSRDLYQLH QGLWHLFPNR PDAARDFLFH VEKRNTPEGC HVLLQSAQMP  60
VSTAVATVIK TKQVEFQLQV GVPLYFRLRA NPIKTILDNQ KRLDSKGNIK RCRVPLIKEA  120
EQIAWLQRKL GNAARVEDVH PISERPQYFS GDGKSGKIQT VCFEGVLTIN DAPALIDLVQ  180
QGIGPAKSMG CGLLSLAPL                                               199

SEQ ID NO: 6              moltype = DNA  length = 392
FEATURE                   Location/Qualifiers
misc_feature              1..392
                          note = Description of Artificial Sequence: Synthetic
                           polynucleotide
source                    1..392
                          mol_type = other DNA
                          organism = synthetic construct
SEQUENCE: 6
actggaaagc gggcagtgaa aggaaggccc atgaggccag ttaattaagc ggatcctggc  60
ggcggcagcg gcggcggcag cgacaagcag aagaacggca tcaaggcgaa cttcaagatc  120
cgccacaaca tcgaggacgg cggcgtgcag ctcgccgacc actaccagca gaacaccccc  180
atcggcgacg gccccgtgct gctgcccgac aaccactacc tgagctacca gtccgccctg  240
agcaaagacc ccaacgagaa gcgcgatcac atggtcctgc tggagttcgt gaccgccgcc  300
gggatcactc tcggcatgga cgagctgtac aagtaagcgg ccgcggcgcg cctaggcctt  360
gacggccttc cttcaattcg ccctatagtg ag                                392

SEQ ID NO: 7              moltype = DNA  length = 603
FEATURE                   Location/Qualifiers
misc_feature              1..603
                          note = Description of Artificial Sequence: Synthetic
                           polynucleotide
source                    1..603
                          mol_type = other DNA
                          organism = synthetic construct
SEQUENCE: 7
cactataggg cgaattggcg gaaggccgtc aaggccgcat ttaattaagc ggccgcaggc  60
ggcggcagcg gcggcggcag catggtgagc aagggcgagg agctgttcac cggggtggtg  120
cccatcctgg tcgagctgga cggcgacgta aacggccaca agttcagcgt gtccggcgag  180
ggcgagggcg atgccaccta cggcaagctg accctgaagc tcatctgcac caccggcaag  240
ctgcccgtgc cctggcccac cctcgtgacc accctcggct acggcctgca gtgcttcgcc  300
cgctaccccg accacatgaa gcagcacgac ttcttcaagt ccgccatgcc cgaaggctac  360
gtccaggagc gcaccatctt cttcaaggac gacggcaact acaagacccg cgccgaggtg  420
aagttcgagg gcgacaccct ggtgaaccgc atcgagctga agggcatcga cttcaaggag  480
gacggcaaca tcctggggca caagctggag tacaactaca acagccacaa cgtctatatc  540
acggcctaac tcgagggcgc gccctgggcc tcatgggcct tccgctcact gcccgctttc  600
cag                                                                603

SEQ ID NO: 8              moltype = DNA  length = 679
FEATURE                   Location/Qualifiers
misc_feature              1..679
                          note = Description of Artificial Sequence: Synthetic
                           polynucleotide
source                    1..679
                          mol_type = other DNA
                          organism = synthetic construct
SEQUENCE: 8
cactataggg cgaattggcg gaaggccgtc aaggccgcat gagctccatg gaaacaaaga  60
attagctgat ctttaataat aaggaaatgt tacattaagg ttggtgggtt gtttttatgg  120
gaaaaaatgc tttaagaaca aatgtatact tttagagagt tccccgcgcc agcggggata  180
aaccgggccg attgaaggtc cggtggatgg cttaaaagag ttccccgcgc cagcggggat  240
aaaccgccgc aggtacagca ggtagcgcag atcatcaaga gttccccgcg ccagcgggga  300
taaaccgact tctctccgaa aagtcaggac gctgtggcag agttccccgc gccagcgggg  360
ataaaccgcc tacgcgctga acgccagcgg tgtggtgaat gagttccccg cgccagcggg  420
gataaaccgg tgtggccatg cacgccttta acggtgaact ggagttcccc gcgccagcgg  480
ggataaaccg cacgaactca gccagaacga caaacaaaag gcgagttccc cgcgccagcg  540
gggataaacc ggcaccagta cgcgccccac gctgacggtt tctgagttcc ccgcgccagc  600
ggggataaac cgcagctccc attttcaaac ccaggtaccc tgggcctcat gggccttccg  660
ctcactgccc gctttccag                                               679

SEQ ID NO: 9              moltype = DNA  length = 685
```

```
FEATURE                Location/Qualifiers
misc_feature           1..685
                       note = Description of Artificial Sequence: Synthetic
                        polynucleotide
source                 1..685
                       mol_type = other DNA
                       organism = synthetic construct
SEQUENCE: 9
gagctcccgg gctgacggta atagaggcac ctacaggctc cggtaaaacg gaaacagcgc  60
tggcctatgc ttggaaactt attgatcaac aaattgcgga tagtgttatt tttgccctcc  120
caacacaagc taccgcgaat gctatgctta cgagaatgga agcgagcgcg agccacttat  180
tttcatcccc aaatcttatt cttgctcatg gcaattcacg gtttaaccac ctctttcaat  240
caataaaatc acgcgcgatt actgaacagg ggcaagaaga agcgtgggtt cagtgttgtc  300
agtggttgtc acaaagcaat aagaaagtgt ttcttgggca aatcggcgtt tgcacgattg  360
atcaggtgtt gatttcggta ttgccagtta aacaccgctt tatccgtggt ttgggaattg  420
gtagatctgt tttaattgtt aatgaagttc atgcttacga cacctatatg aacggcttgc  480
tcgaggcagt gctcaaggct caggctgatg tgggagggag tgttattctt ctttccgcaa  540
ccctaccaat gaaacaaaaa cagaagcttc tggatactta tggtctgcat acagatccag  600
tggaaaataa ctccgcatat ccactcatta actggcgagg tgtgaatggt gcgcaacgtt  660
ttgatctgct agcggatccg gtacc                                        685

SEQ ID NO: 10          moltype = DNA  length = 37
FEATURE                Location/Qualifiers
misc_feature           1..37
                       note = Description of Artificial Sequence: Synthetic primer
source                 1..37
                       mol_type = other DNA
                       organism = synthetic construct
SEQUENCE: 10
atagcgccat ggaacctttt aaatatatat gccatta                           37

SEQ ID NO: 11          moltype = DNA  length = 41
FEATURE                Location/Qualifiers
misc_feature           1..41
                       note = Description of Artificial Sequence: Synthetic primer
source                 1..41
                       mol_type = other DNA
                       organism = synthetic construct
SEQUENCE: 11
acagtgggat ccgctttggg atttgcaggg atgactctgg t                      41

SEQ ID NO: 12          moltype = DNA  length = 43
FEATURE                Location/Qualifiers
misc_feature           1..43
                       note = Description of Artificial Sequence: Synthetic primer
source                 1..43
                       mol_type = other DNA
                       organism = synthetic construct
SEQUENCE: 12
atagcgtcat gaatttgctt attgataact ggattcctgt acg                    43

SEQ ID NO: 13          moltype = DNA  length = 44
FEATURE                Location/Qualifiers
misc_feature           1..44
                       note = Description of Artificial Sequence: Synthetic primer
source                 1..44
                       mol_type = other DNA
                       organism = synthetic construct
SEQUENCE: 13
acagtggcgg ccgcgccatt tgatggccct ccttgcggtt ttaa                   44

SEQ ID NO: 14          moltype = DNA  length = 45
FEATURE                Location/Qualifiers
misc_feature           1..45
                       note = Description of Artificial Sequence: Synthetic primer
source                 1..45
                       mol_type = other DNA
                       organism = synthetic construct
SEQUENCE: 14
cgtatatcaa actttccaat agcatgaaga gcaatgaaaa ataac                  45

SEQ ID NO: 15          moltype = DNA  length = 23
FEATURE                Location/Qualifiers
misc_feature           1..23
                       note = Description of Artificial Sequence: Synthetic primer
source                 1..23
                       mol_type = other DNA
                       organism = synthetic construct
SEQUENCE: 15
```

```
atgataccgc gagacccacg ctc                                         23

SEQ ID NO: 16          moltype = DNA  length = 24
FEATURE                Location/Qualifiers
misc_feature           1..24
                       note = Description of Artificial Sequence: Synthetic primer
source                 1..24
                       mol_type = other DNA
                       organism = synthetic construct
SEQUENCE: 16
cggataaagt tgcaggacca cttc                                        24

SEQ ID NO: 17          moltype = AA  length = 199
FEATURE                Location/Qualifiers
source                 1..199
                       mol_type = protein
                       organism = Escherichia coli
SEQUENCE: 17
MYLSKVIIAR AWSRDLYQLH QGLWHLFPNR PDAARDFLFH VEKRNTPEGC HVLLQSAQMP  60
VSTAVATVIK TKQVEFQLQV GVPLYFRLRA NPIKTILDNQ KRLDSKGNIK RCRVPLIKEA  120
EQIAWLQRKL GNAARVEDVH PISERPQYFS GDGKSGKIQT VCFEGVLTIN DAPALIDLVQ  180
QGIGPAKSMG CGLLSLAPL                                              199

SEQ ID NO: 18          moltype = DNA  length = 2154
FEATURE                Location/Qualifiers
misc_feature           1..2154
                       note = Description of Artificial Sequence: Synthetic
                        polynucleotide
source                 1..2154
                       mol_type = other DNA
                       organism = synthetic construct
SEQUENCE: 18
atggctcaac tggttaaaag cgaactggaa gagaaaaaaa gtgaactgcg ccacaaactg  60
aaatatgtgc cgcatgaata tatcgagctg attgaaattg cacgtaatcc gacccaggat  120
cgtattctgg aaatgaaagt gatggaattt tttatgaaag tgtacggcta tcgcggtgaa  180
catctgggtg gtagccgtaa accggatggt gcaatttata ccgttggtag cccgattgat  240
tatggtgtta ttgttgatac caaagcctat agcggtggtt ataatctgcc gattggtcag  300
gcagatgaaa tggaacgtta tgtggaagaa aatcagaccc gtgataaaca tctgaatccg  360
aatgaatggt ggaaagttta tccgagcagc gttaccgagt ttaaattcct gtttgttagc  420
ggtcacttca aaggcaacta taaagcacag ctgacccgtc tgaatcatat taccaattgt  480
aatggtgcag ttctgagcgt tgaagaactg ctgattggtg gtgaaatgat taaagcaggc  540
accctgaccc tggaagaagt tcgtcgcaaa tttaacaatg gcgaaatcaa ctttgcggat  600
cccaccaacc gcgcgaaagg cctggaagcg gtgagcgtgg cgagcatgaa tttgcttatt  660
gataactgga ttcctgtacg cccgcgaaac ggggggaaag tccaaatcat aaatctgcaa  720
tcgctatact gcagtagaga tcagtggcga ttaagtttgc cccgtgacga tatggaactg  780
gccgctttag cactgctggt ttgcattggg caaattatcg ccccggcaaa agatgacgtt  840
gaatttcgac atcgcataat gaatccgctc actgaagatg agtttcaaca actcatcgcg  900
ccgtggatag atatgttcta ccttaatcac gcagaacatc cctttatgca gaccaaaggt  960
gtcaaagcaa atgatgtgac tccaatggaa aaactgttgg ctggggtaag cggcgcgacg  1020
aattgtgcat ttgtcaatca accggggcag ggtgaagcat tatgtggtgg atgcactgcg  1080
attgcgttat tcaaccaggc gaatcaggca ccaggttttg gtggtggttt taaaagcggt  1140
ttacgtggag gaacacctgt aacaacgttc gtacgtggga tcgatcttcg ttcaacggtg  1200
ttactcaatg tcctcacatt acctcgtctt caaaaacaat ttcctaatga atcacatacg  1260
gaaaaccaac ctacctggat taaacctatc aagtccaatg agtctatacc tgcttcgtca  1320
attgggtttg tccgtggtct attctggcaa ccagcgcata ttgaattatg cgatcccatt  1380
gggattggta aatgttcttg ctgtggacag gaaagcaatt tgcgttatac cggttttctt  1440
aaggaaaaat ttacctttac agttaatggg ctatggcccc atccgcattc cccttgtctg  1500
gtaacagtca agaaagggga ggttgaggaa aaatttcttg ctttcaccac ctccgcacca  1560
tcatggacac aaatcagccg agttgtggta gataagatta ttcaaaatga aaatggaaat  1620
cgcgtggcgg cggttgtgaa tcaattcaga aatattgcgc cgcaaagtcc tcttgaattg  1680
attatggggg gatatcgtaa taatcaagca tctattcttg aacggcgtca tgatgtgttg  1740
atgtttaatc aggggtggca acaatacggc aatgtgataa acgaaatagt gactgttggt  1800
ttgggatata aaacagcctt acgcaaggcg ttatatacct ttgcagaagg gtttaaaaat  1860
aaagacttca aggggccgg agtctctgtt catgagactg cagaaaggca tttctatcga  1920
cagagtgaat tattaattcc cgatgtactg gcgaatgtta atttttccca ggctgatgag  1980
gtaatagctg atttacgaga caaacttcat caattgtgtg aaatgctatt taatcaatct  2040
gtagctccct atgcacatca tcctaaatta ataagcacat tagcgcttgc ccgcgccacg  2100
ctatacaaac atttacggga gttaaaaccg caaggagggc catcaaatgg ctga       2154

SEQ ID NO: 19          moltype = AA  length = 717
FEATURE                Location/Qualifiers
REGION                 1..717
                       note = Description of Artificial Sequence: Synthetic
                        polypeptide
source                 1..717
                       mol_type = protein
                       organism = synthetic construct
SEQUENCE: 19
MAQLVKSELE EKKSELRHKL KYVPHEYIEL IEIARNPTQD RILEMKVMEF FMKVYGYRGE  60
```

-continued

```
HLGGSRKPDG AIYTVGSPID YGVIVDTKAY SGGYNLPIGQ ADEMERYVEE NQTRDKHLNP  120
NEWWKVYPSS VTEFKFLFVS GHFKGNYKAQ LTRLNHITNC NGAVLSVEEL LIGGEMIKAG  180
TLTLEEVRRK FNNGEINFAD PTNRAKGLEA VSVASMNLLI DNWIPVRPRN GGKVQIINLQ  240
SLYCSRDQWR LSLPRDDMEL AALALLVCIG QIIAPAKDDV EFRHRIMNPL TEDEFQQLIA  300
PWIDMFYLNH AEHPFMQTKG VKANDVTPME KLLAGVSGAT NCAFVNQPGQ GEALCGGCTA  360
IALFNQANQA PGFGGGFKSG LRGGTPVTTF VRGIDLRSTV LLNVLTLPRL QKQFPNESHT  420
ENQPTWIKPI KSNESIPASS IGFVRGLFWQ PAHIELCDPI GIGKCSCCGQ ESNLRYTGFL  480
KEKFTFTVNG LWPHPHSPCL VTVKKGEVEE KFLAFTTSAP SWTQISRVVV DKIIQNENGN  540
RVAAVVNQFR NIAPQSPLEL IMGGYRNNQA SILERRHDVL MFNQGWQQYG NVINEIVTVG  600
LGYKTALRKA LYTFAEGFKN KDFKGAGVSV HETAERHFYR QSELLIPDVL ANVNFSQADE  660
VIADLRDKLH QLCEMLFNQS VAPYAHHPKL ISTLALARAT LYKHLRELKP QGGPSNG     717

SEQ ID NO: 20          moltype = DNA  length = 2154
FEATURE                Location/Qualifiers
misc_feature           1..2154
                       note = Description of Artificial Sequence: Synthetic
                        polynucleotide
source                 1..2154
                       mol_type = other DNA
                       organism = synthetic construct
SEQUENCE: 20
atggctcaac tggttaaaag cgaactggaa gagaaaaaaa gtgaactgcg ccacaaactg  60
aaatatgtgc cgcatgaata tatcgagctg attgaaattg cacgtaatcc gacccaggat  120
cgtattctgg aaatgaaagt gatggaattt tttatgaaag tgtacggcta tcgcggtgaa  180
catctgggtg gtagccgtaa accggatggt gcaatttata ccgttggtag cccgattgat  240
tatggtgtta ttgttgatac caaagcctat agcggtggtt ataatctgcc gattggtcag  300
gcagatgaaa tgcagcgtta tgtgaaagaa aatcagaccc gcaacaaaca tattaacccg  360
aatgaatggt ggaaagttta tccgagcagc gttaccgagt ttaaattcct gtttgttagc  420
ggtcacttca aaggcaacta taaagcacag ctgacccgtc tgaatcgtaa aaccaattgt  480
aatggtgcag ttctgagcgt tgaagaactg ctgattggtg gtgaaatgat taaagcaggc  540
accctgaccc tggaagaagt tcgtcgcaaa tttaacaatg gcgaaatcaa ctttgcggat  600
cccaccaacc gcgcgaaagg cctggaagcg gtgagcgtgg cgagcatgaa tttgcttatt  660
gataactgga ttcctgtacg cccgcgaaac ggggggaaag tccaaatcat aaatctgcaa  720
tcgctatact gcagtagaga tcagtggcga ttaagtttgc cccgtgacga tatggaactg  780
gccgctttag cactgctggt ttgcattggg caaattatcg ccccggcaaa agatgacgtt  840
gaatttcgac atcgcataat gaatccgctc actgaagatg agtttcaaca actcatcgcg  900
ccgtggatag atatgttcta ccttaatcac gcagaacatc cctttatgca gaccaaaggt  960
gtcaaagcaa atgatgtgac tccaatggaa aaactgttgg ctggggtaag cggcgcgacg  1020
aattgtgcat ttgtcaatca accggggcag ggtgaagcat tatgtggtgg atgcactgcg  1080
attgcgttat tcaaccaggc gaatcaggca ccaggttttg gtggtggttt taaaagcggt  1140
ttacgtggag gaacacctgt aacaacgttc gtacgtggga tcgatcttcg ttcaacggtg  1200
ttactcaatg tcctcacatt acctcgtctt caaaaacaat ttcctaatga atcacatacg  1260
gaaaaccaac ctacctggat taaacctatc aagtccaatg agtctatacc tgcttcgtca  1320
attgggtttg tccgtggtct attctggcaa ccagcgcata ttgaattatg cgatcccatt  1380
gggattggta aatgttcttg ctgtggacag gaaagcaatt tgcgttatac cggtttttctt  1440
aaggaaaaat ttacctttac agttaatggg ctatggcccc atccgcattc cccttgtctg  1500
gtaacagtca agaaagggga ggttgaggaa aaatttcttg ctttcaccac ctccgcacca  1560
tcatggacac aaatcagccg agttgtggta gataagatta ttcaaaatga aaatggaaat  1620
cgcgtggcgg cggttgtgaa tcaattcaga aatattgcgc cgcaaagtcc tcttgaattg  1680
attatggggg gatatcgtaa taatcaagca tctattcttg aacggcgtca tgatgtgttg  1740
atgtttaatc aggggtggca acaatacggc aatgtgataa acgaaatagt gactgttggt  1800
ttgggatata aaacagcctt acgcaaggcg ttatataacct ttgcagaagg gtttaaaaat  1860
aaagacttca aggggccgg agtctctgtt catgagactg cagaaaggca tttctatcga  1920
cagagtgaat tattaattcc cgatgtactg gcgaatgtta atttttccca ggctgatgag  1980
gtaatagctg atttacgaga caaacttcat caattgtgtg aaatgctatt taatcaatct  2040
gtagctccct atgcacatca tcctaaatta ataagcacat tagcgcttgc ccgcgccacg  2100
ctatacaaac atttacggga gttaaaaccg caaggagggc catcaaatgg ctga        2154

SEQ ID NO: 21          moltype = AA  length = 717
FEATURE                Location/Qualifiers
REGION                 1..717
                       note = Description of Artificial Sequence: Synthetic
                        polypeptide
source                 1..717
                       mol_type = protein
                       organism = synthetic construct
SEQUENCE: 21
MAQLVKSELE EKKSELRHKL KYVPHEYIEL IEIARNPTQD RILEMKVMEF FMKVYGYRGE  60
HLGGSRKPDG AIYTVGSPID YGVIVDTKAY SGGYNLPIGQ ADEMQRYVKE NQTRNKHINP  120
NEWWKVYPSS VTEFKFLFVS GHFKGNYKAQ LTRLNRKTNC NGAVLSVEEL LIGGEMIKAG  180
TLTLEEVRRK FNNGEINFAD PTNRAKGLEA VSVASMNLLI DNWIPVRPRN GGKVQIINLQ  240
SLYCSRDQWR LSLPRDDMEL AALALLVCIG QIIAPAKDDV EFRHRIMNPL TEDEFQQLIA  300
PWIDMFYLNH AEHPFMQTKG VKANDVTPME KLLAGVSGAT NCAFVNQPGQ GEALCGGCTA  360
IALFNQANQA PGFGGGFKSG LRGGTPVTTF VRGIDLRSTV LLNVLTLPRL QKQFPNESHT  420
ENQPTWIKPI KSNESIPASS IGFVRGLFWQ PAHIELCDPI GIGKCSCCGQ ESNLRYTGFL  480
KEKFTFTVNG LWPHPHSPCL VTVKKGEVEE KFLAFTTSAP SWTQISRVVV DKIIQNENGN  540
RVAAVVNQFR NIAPQSPLEL IMGGYRNNQA SILERRHDVL MFNQGWQQYG NVINEIVTVG  600
LGYKTALRKA LYTFAEGFKN KDFKGAGVSV HETAERHFYR QSELLIPDVL ANVNFSQADE  660
VIADLRDKLH QLCEMLFNQS VAPYAHHPKL ISTLALARAT LYKHLRELKP QGGPSNG     717
```

```
SEQ ID NO: 22          moltype = DNA  length = 2235
FEATURE                Location/Qualifiers
misc_feature           1..2235
                       note = Description of Artificial Sequence: Synthetic
                        polynucleotide
source                 1..2235
                       mol_type = other DNA
                       organism = synthetic construct
SEQUENCE: 22
atgcatcacc atcatcacca cccgaaaaaa aagcgcaaag tggatccgaa gaaaaaacgt  60
aaagttgaag atccgaaaga catggctcaa ctggttaaaa gcgaactgga agagaaaaaa  120
agtgaactgc gccacaaact gaaatatgtg ccgcatgaat atatcgagct gattgaaatt  180
gcacgtaatc cgacccagga tcgtattctg gaaatgaaag tgatggaatt ttttatgaaa  240
gtgtacggct atcgcggtga acatctgggt ggtagccgta aaccggatgg tgcaatttat  300
accgttggta gcccgattga ttatggtgtt attgttgata ccaaagccta tagcggtggt  360
tataatctgc cgattggtca ggcagatgaa atgcagcgtt atgtgaaaga aaatcagacc  420
cgcaacaaac atattaaccc gaatgaatgg tggaaagttt atccgagcag cgttaccgag  480
tttaaattcc tgtttgttag cggtcacttc aaaggcaact ataaagcaca gctgacccgt  540
ctgaatcgta aaaccaattg taatggtgca gttctgagcg ttgaagaact gctgattggt  600
ggtgaaatga ttaaagcagg caccctgacc ctggaagaag ttcgtcgcaa atttaacaat  660
ggcgaaatca actttgcgga tcccaccaac cgcgcgaaag gcctggaagc ggtgagcgtg  720
gcgagcatga atttgcttat tgataactgg attcctgtac gcccgcgaaa cgggggggaaa  780
gtccaaatca taaatctgca atcgctatac tgcagtagag atcagtggcg attaagtttg  840
ccccgtgacg atatggaact ggccgcttta gcactgctgg tttgcattgg gcaaattatc  900
gccccggcaa aagatgacgt tgaatttcga catcgcataa tgaatccgct cactgaagat  960
gagtttcaac aactcatcgc gccgtggata gatatgttct accttaatca cgcagaacat  1020
ccctttatgc agaccaaagg tgtcaaagca aatgatgtga ctccaatgga aaaactgttg  1080
gctggggtaa gcggcgcgac gaattgtgca tttgtcaatc aaccggggca gggtgaagca  1140
ttatgtggtg gatgcactgc gattgcgtta ttcaaccagg cgaatcaggc accaggtttt  1200
ggtggtggtt ttaaaagcgg tttacgtgga ggaacacctg taacaacgtt cgtacgtggg  1260
atcgatcttc gttcaacggt gttactcaat gtcctcacat tacctcgtct tcaaaaacaa  1320
tttcctaatg aatcacatac ggaaaaccaa cctacctgga ttaaacctat caagtccaat  1380
gagtctatac ctgcttcgtc aattgggttt gtccgtggtc tattctggca accagcgcat  1440
attgaattat gcgatcccat tggattggt aaatgttctt gctgtggaca ggaaagcaat  1500
ttgcgttata ccggttttct taaggaaaaa tttacctttta cagttaatgg gctatggccc  1560
catccgcatt ccccttgtct ggtaacagtc aagaaagggg aggttgagga aaaatttctt  1620
gctttcacca cctccgcacc atcatggaca caaatcagcc gagttgtggt agataagatt  1680
attcaaaatg aaaatggaaa tcgcgtggcg gcggttgtga atcaattcag aaatattgcg  1740
ccgcaaagtc ctcttgaatt gattatgggg ggatatcgta ataatcaagc atctattctt  1800
gaacggcgtc atgatgtgtt gatgtttaat caggggtggc aacaatacgg caatgtgata  1860
aacgaaatag tgactgttgg tttgggatat aaaacagcct tacgcaaggc gttatatacc  1920
tttgcagaag ggtttaaaaa taaagacttc aaaggggccg gagtctctgt tcatgagact  1980
gcagaaaggc atttctatcg acagagtgaa ttattaattc ccgatgtact ggcgaatgtt  2040
aatttttccc aggctgatga ggtaatagct gatttacgag acaaacttca tcaattgtgt  2100
gaaatgctat ttaatcaatc tgtagctccc tatgcacatc atcctaaatt aataagcaca  2160
ttagcgcttg cccgcgccac gctatacaaa catttacggg agttaaaacc gcaaggaggg  2220
ccatcaaatg gctga                                                   2235

SEQ ID NO: 23          moltype = AA  length = 744
FEATURE                Location/Qualifiers
REGION                 1..744
                       note = Description of Artificial Sequence: Synthetic
                        polypeptide
source                 1..744
                       mol_type = protein
                       organism = synthetic construct
SEQUENCE: 23
MHHHHHHPKK KRKVDPKKKR KVEDPKDMAQ LVKSELEEKK SELRHKLKYV PHEYIELIEI  60
ARNPTQDRIL EMKVMEFFMK VYGYRGEHLG GSRKPDGAIY TVGSPIDYGV IVDTKAYSGG  120
YNLPIGQADE MQRYVKENQT RNKHINPNEW WKVYPSSVTE FKFLFVSGHF KGNYKAQLTR  180
LNRKTNCNGA VLSVEELLIG GEMIKAGTLT LEEVRRKFNN GEINFADPTN RAKGLEAVSV  240
ASMNLLIDNW IPVRPRNGGK VQIINLQSLY CSRDQWRLSL PRDDMELAAL ALLVCIGQII  300
APAKDDVEFR HRIMNPLTED EFQQLIAPWI DMFYLNHAEH PFMQTKGVKA NDVTPMEKLL  360
AGVSGATNCA FVNQPGQGEA LCGGCTAIAL FNQANQAPGF GGGFKSGLRG GTPVTTFVRG  420
IDLRSTVLLN VLTLPRLQKQ FPNESHTENQ PTWIKPIKSN ESIPASSIGF VRGLFWQPAH  480
IELCDPIGIG KCSCCGQESN LRYTGFLKEK FTFTVNGLWP HPHSPCLVTV KKGEVEEKFL  540
AFTTSAPSWT QISRVVVDKI IQNENGNRVA AVVNQFRNIA PQSPLELIMG GYRNNQASIL  600
ERRHDVLMFN QGWQQYGNVI NEIVTVGLGY KTALRKALYT FAEGFKNKDF KGAGVSVHET  660
AERHFYRQSE LLIPDVLANV NFSQADEVIA DLRDKLHQLC EMLFNQSVAP YAHHPKLIST  720
LALARATLYK HLRELKPQGG PSNG                                         744

SEQ ID NO: 24          moltype = DNA  length = 2235
FEATURE                Location/Qualifiers
misc_feature           1..2235
                       note = Description of Artificial Sequence: Synthetic
                        polynucleotide
source                 1..2235
                       mol_type = other DNA
```

```
                         organism = synthetic construct
SEQUENCE: 24
atgcatcacc atcatcacca cccgaaaaaa aagcgcaaag tggatccgaa gaaaaaacgt  60
aaagttgaag atccgaaaga catggctcaa ctggttaaaa gcgaactgga agagaaaaaa  120
agtgaactgc gccacaaact gaaatatgtg ccgcatgaat atatcgagct gattgaaatt  180
gcacgtaatc cgacccagga tcgtattctg gaaatgaaag tgatggaatt ttttatgaaa  240
gtgtacggct atcgcggtga acatctgggt ggtagccgta aaccggatgg tgcaatttat  300
accgttggta gcccgattga ttatggtgtt attgttgata ccaaagccta tagcggtggt  360
tataatctgc cgattggtca ggcagatgaa atggaacgtt atgtggaaga aaatcagacc  420
cgtgataaac atctgaatcc gaatgaatgg tggaaagttt atccgagcag cgttaccgag  480
tttaaattcc tgtttgttag cggtcacttc aaaggcaact ataaagcaca gctgacccgt  540
ctgaatcata ttaccaattg taatggtgca gttctgagcg ttgaagaact gctgattggt  600
ggtgaaatga ttaaagcagg caccctgacc ctggaagaag ttcgtcgcaa atttaacaat  660
ggcgaaatca actttgcgga tcccaccaac cgcgcgaaag gcctggaagc ggtgagcgtg  720
gcgagcatga atttgcttat tgataactgg attcctgtac gcccgcgaaa cggggggaaa  780
gtccaaatca taaatctgca atcgctatac tgcagtagag atcagtggcg attaagtttg  840
ccccgtgacg atatggaact ggccgcttta gcactgctgg tttgcattgg gcaaattatc  900
gccccggcaa aagatgacgt tgaatttcga catcgcataa tgaatccgct cactgaagat  960
gagtttcaac aactcatcgc gccgtggata gatatgttct accttaatca cgcagaacat  1020
ccctttatgc agaccaaagg tgtcaaagca aatgatgtga ctccaatgga aaaactgttg  1080
gctggggtaa gcggcgcgac gaattgtgca tttgtcaatc aaccggggca gggtgaagca  1140
ttatgtggtg gatgcactgc gattgcgtta ttcaaccagg cgaatcaggc accaggtttt  1200
ggtggtggtt ttaaaagcgg tttacgtgga ggaacacctg taacaacgtt cgtacgtggg  1260
atcgatcttc gttcaacggt gttactcaat gtcctcacat tacctcgtct tcaaaaacaa  1320
tttcctaatg aatcacatac ggaaaaccaa cctacctgga ttaaacctat caagtccaat  1380
gagtctatac ctgcttcgtc aattgggttt gtccgtggtc tattctggca accagcgcat  1440
attgaattat gcgatcccat tgggattggt aaatgttctt gctgtggaca ggaaagcaat  1500
ttgcgttata ccggttttct taaggaaaaa tttaccttta cagttaatgg gctatggccc  1560
catccgcatt ccccttgtct ggtaacagtc aagaaagggg aggttgagga aaaatttctt  1620
gctttcacca cctccgcacc atcatggaca caaatcagcc gagttgtggt agataagatt  1680
attcaaaatg aaaatggaaa tcgcgtggcg gcggttgtga atcaattcag aaatattgcg  1740
ccgcaaagtc ctcttgaatt gattatgggg ggatatcgta ataatcaagc atctattctt  1800
gaacggcgtc atgatgtgtt gatgtttaat caggggtggc aacaatacgg caatgtgata  1860
aacgaaatag tgactgttgg tttgggatat aaaacagcct tacgcaaggc gttatatacc  1920
tttgcagaag ggtttaaaaa taaagacttc aaaggggccg gagtctctgt tcatgagact  1980
gcagaaaggc atttctatcg acagagtgaa ttattaattc ccgatgtact ggcgaatgtt  2040
aatttttccc aggctgatga ggtaatagct gatttacgag acaaacttca tcaattgtgt  2100
gaaatgctat ttaatcaatc tgtagctccc tatgcacatc atcctaaatt aataagcaca  2160
ttagcgcttg cccgcgccac gctatacaaa catttacggg agttaaaacc gcaaggaggg  2220
ccatcaaatg gctga                                                  2235

SEQ ID NO: 25            moltype = AA  length = 744
FEATURE                  Location/Qualifiers
REGION                   1..744
                         note = Description of Artificial Sequence: Synthetic
                          polypeptide
source                   1..744
                         mol_type = protein
                         organism = synthetic construct
SEQUENCE: 25
MHHHHHHPKK KRKVDPKKKR KVEDPKDMAQ LVKSELEEKK SELRHKLKYV PHEYIELIEI  60
ARNPTQDRIL EMKVMEFFMK VYGYRGEHLG GSRKPDGAIY TVGSPIDYGV IVDTKAYSGG  120
YNLPIGQADE MERYVEENQT RDKHLNPNEW WKVYPSSVTE FKFLFVSGHF KGNYKAQLTR  180
LNHITNCNGA VLSVEELLIG GEMIKAGTLT LEEVRRKFNN GEINFADPTN RAKGLEAVSV  240
ASMNLLIDNW IPVRPRNGGK VQIINLQSLY CSRDQWRLSL PRDDMELAAL ALLVCIGQII  300
APAKDDVEFR HRIMNPLTED EFQQLIAPWI DMFYLNHAEH PFMQTKGVKA NDVTPMEKLL  360
AGVSGATNCA FVNQPGQGEA LCGGCTAIAL FNQANQAPGF GGGFKSGLRG GTPVTTFVRG  420
IDLRSTVLLN VLTLPRLQKQ FPNESHTENQ PTWIKPIKSN ESIPASSIGF VRGLFWQPAH  480
IELCDPIGIG KCSCCGQESN LRYTGFLKEK FTFTVNGLWP HPHSPCLVTV KKGEVEEKFL  540
AFTTSAPSWT QISRVVVDKI IQNENGNRVA AVVNQFRNIA PQSPLELIMG GYRNNQASIL  600
ERRHDVLMFN QGWQQYGNVI NEIVTVGLGY KTALRKALYT FAEGFKNKDF KGAGVSVHET  660
AERHFYRQSE LLIPDVLANV NFSQADEVIA DLRDKLHQLC EMLFNQSVAP YAHHPKLIST  720
LALARATLYK HLRELKPQGG PSNG                                        744

SEQ ID NO: 26            moltype = DNA  length = 168
FEATURE                  Location/Qualifiers
misc_feature             1..168
                         note = Description of Artificial Sequence: Synthetic
                          polynucleotide
source                   1..168
                         mol_type = other DNA
                         organism = synthetic construct
SEQUENCE: 26
gaattcacaa cggtgagcaa gtcactgttg gcaagccagg atctgaacaa taccgtcttg  60
ctttcgagcg ctagctctag aactagtcct cagcctaggc ctcgttccga agctgtcttt  120
cgctgctgag ggtgacgatc ccgcataggc ggcctttaac tcggatcc              168

SEQ ID NO: 27            moltype = DNA  length = 163
FEATURE                  Location/Qualifiers
```

```
misc_feature          1..163
                      note = Description of Artificial Sequence: Synthetic
                       polynucleotide
source                1..163
                      mol_type = other DNA
                      organism = synthetic construct
SEQUENCE: 27
gaattcacaa cggtgagcaa gtcactgttg gcaagccagg atctgaacaa taccgtcttt  60
tcgagcgcta gctctagaac tagtcctcag cctaggcctc gttcaagctg tctttcgctg  120
ctgagggtga cgatcccgca taggcggcct ttaactcgga tcc                    163

SEQ ID NO: 28         moltype = DNA  length = 158
FEATURE               Location/Qualifiers
misc_feature          1..158
                      note = Description of Artificial Sequence: Synthetic
                       polynucleotide
source                1..158
                      mol_type = other DNA
                      organism = synthetic construct
SEQUENCE: 28
gaattcacaa cggtgagcaa gtcactgttg gcaagccagg atctgaacaa taccgtcttc  60
gagcgctagc tctagaacta gtcctcagcc taggcctcga agctgtcttt cgctgctgag  120
ggtgacgatc ccgcataggc ggcctttaac tcggatcc                          158

SEQ ID NO: 29         moltype = DNA  length = 153
FEATURE               Location/Qualifiers
misc_feature          1..153
                      note = Description of Artificial Sequence: Synthetic
                       polynucleotide
source                1..153
                      mol_type = other DNA
                      organism = synthetic construct
SEQUENCE: 29
gaattcacaa cggtgagcaa gtcactgttg gcaagccagg atctgaacaa taccgtcttg  60
cgctagctct agaactagtc ctcagcctag gcctaagctg tctttcgctg ctgagggtga  120
cgatcccgca taggcggcct ttaactcgga tcc                               153

SEQ ID NO: 30         moltype = DNA  length = 148
FEATURE               Location/Qualifiers
misc_feature          1..148
                      note = Description of Artificial Sequence: Synthetic
                       polynucleotide
source                1..148
                      mol_type = other DNA
                      organism = synthetic construct
SEQUENCE: 30
gaattcacaa cggtgagcaa gtcactgttg gcaagccagg atctgaacaa taccgtcttg  60
ctagctctag aactagtcct cagcctagga agctgtcttt cgctgctgag ggtgacgatc  120
ccgcataggc ggcctttaac tcggatcc                                     148

SEQ ID NO: 31         moltype = DNA  length = 143
FEATURE               Location/Qualifiers
misc_feature          1..143
                      note = Description of Artificial Sequence: Synthetic
                       polynucleotide
source                1..143
                      mol_type = other DNA
                      organism = synthetic construct
SEQUENCE: 31
gaattcacaa cggtgagcaa gtcactgttg gcaagccagg atctgaacaa taccgtcttc  60
tctagaacta gtcctcagcc taggaagctg tctttcgctg ctgagggtga cgatcccgca  120
taggcggcct ttaactcgga tcc                                          143

SEQ ID NO: 32         moltype = DNA  length = 41
FEATURE               Location/Qualifiers
misc_feature          1..41
                      note = Description of Artificial Sequence: Synthetic
                       oligonucleotide
source                1..41
                      mol_type = other DNA
                      organism = synthetic construct
SEQUENCE: 32
cttgcgctag ctctagaact agtcctcagc ctaggcctaa g                      41

SEQ ID NO: 33         moltype = DNA  length = 41
FEATURE               Location/Qualifiers
misc_feature          1..41
                      note = Description of Artificial Sequence: Synthetic
                       oligonucleotide
```

```
source                  1..41
                        mol_type = other DNA
                        organism = synthetic construct
SEQUENCE: 33
cttaggccta ggctgaggac tagttctaga gctagcgcaa g                    41

SEQ ID NO: 34           moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 34
cttgcgctag ctctagaact agctagtcct cagcctaggc ctaag                45

SEQ ID NO: 35           moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 35
cttaggccta ggctgaggac tagctagttc tagagctagc gcaag                45

SEQ ID NO: 36           moltype = DNA  length = 1100
FEATURE                 Location/Qualifiers
source                  1..1100
                        mol_type = genomic DNA
                        organism = Homo sapiens
SEQUENCE: 36
ggtggaacaa gatggattat caagtgtcaa gtccaatcta tgacatcaat tattatacat  60
cggagccctg ccaaaaaatc aatgtgaagc aaatcgcagc ccgcctcctg cctccgctct  120
actcactggt gttcatcttt ggttttgtgg gcaacatgct ggtcatcctc atcctgataa  180
actgcaaaag gctgaagagc atgactgaca tctacctgct caacctggcc atctctgacc  240
tgtttttcct tcttactgtc cccttctggg ctcactatgc tgccgcccag tgggactttg  300
gaaatacaat gtgtcaactc ttgacagggc tctattttat aggcttcttc tctggaatct  360
tcttcatcat cctcctgaca atcgataggt acctggctgt cgtccatgct gtgtttgctt  420
taaaagccag gacggtcacc tttggggtgg tgacaagtgt gatcacttgg gtggtggctg  480
tgtttgcgtc tctcccagga atcatcttta ccagatctca aaaagaaggt cttcattaca  540
cctgcagctc tcattttcca tacagtcagt atcaattctg gaagaatttc cagacattaa  600
agatagtcat cttggggctg gtcctgccgc tgcttgtcat ggtcatctgc tactcgggaa  660
tcctaaaaac tctgcttcgg tgtcgaaatg agaagaagag gcacagggct gtgaggctta  720
tcttcaccat catgattgtt tattttctct tctgggctcc ctacaacatt gtccttctcc  780
tgaacacctt ccaggaattc tttggcctga ataattgcag tagctctaac aggttggacc  840
aagctatgca ggtgacagag actcttggga tgacgcactg ctgcatcaac cccatcatct  900
atgcctttgt cggggagaag ttcagaaact acctcttagt cttcttccaa aagcacattg  960
ccaaacgctt ctgcaaatgc tgttctattt tccagcaaga ggctcccgag cgagcaagct  1020
cagtttacac ccgatccact ggggagcagg aaatatctgt gggcttgtga cacggactca  1080
agtgggctgg tgacccagtc                                            1100

SEQ ID NO: 37           moltype = DNA  length = 424
FEATURE                 Location/Qualifiers
misc_feature            1..424
                        note = Description of Artificial Sequence: Synthetic
                         polynucleotide
source                  1..424
                        mol_type = other DNA
                        organism = synthetic construct
SEQUENCE: 37
ccatggtaat acgactcact atagggagaa ttagctgatc tttaataata aggaaatgtt  60
acattaaggt tggtgggttg tttttatggg aaaaaatgct ttaagaacaa atgtatactt  120
ttagagagtt ccccgcgcca gcggggataa accgcaaaca cagcatggac gacagccagg  180
tacctagagt tccccgcgcc agcggggata aaccgcaaac acagcatgga cgacagccag  240
gtacctagag ttccccgcgc cagcggggat aaaccgcaaa cacagcatgg acgacagcca  300
ggtacctaga gttccccgcg ccagcgggga taaaccgaaa acaaaaggct cagtcggaag  360
actgggcctt ttgttttaac cccttggggc ctctaaacgg gtcttgaggg gtttttggg  420
tacc                                                             424

SEQ ID NO: 38           moltype = DNA  length = 424
FEATURE                 Location/Qualifiers
misc_feature            1..424
                        note = Description of Artificial Sequence: Synthetic
                         polynucleotide
source                  1..424
                        mol_type = other DNA
```

```
                        organism = synthetic construct
SEQUENCE: 38
ccatggtaat acgactcact atagggagaa ttagctgatc tttaataata aggaaatgtt  60
acattaaggt tggtgggttg tttttatggg aaaaaatgct ttaagaacaa atgtatactt  120
ttagagagtt ccccgcgcca gcggggataa accgtgtgat cacttgggtg gtggctgtgt  180
ttgcgtgagt tccccgcgcc agcggggata aaccgtgtga tcacttgggt ggtggctgtg  240
tttgcgtgag ttccccgcgc cagcggggat aaaccgtgtg atcacttggg tggtggctgt  300
gtttgcgtga gttccccgcg ccagcgggga taaaccgaaa acaaaaggct cagtcggaag  360
actgggcctt ttgttttaac cccttggggc ctctaaacgg gtcttgaggg gtttttttggg  420
tacc                                                               424

SEQ ID NO: 39           moltype = DNA  length = 43
FEATURE                 Location/Qualifiers
misc_feature            1..43
                        note = Description of Artificial Sequence: Synthetic
                         oligonucleotide
source                  1..43
                        mol_type = other DNA
                        organism = synthetic construct
SEQUENCE: 39
aaggatgcca gtgataagtg gaatgccatg tgggctgtca aaa                    43

SEQ ID NO: 40           moltype = DNA  length = 43
FEATURE                 Location/Qualifiers
misc_feature            1..43
                        note = Description of Artificial Sequence: Synthetic
                         oligonucleotide
source                  1..43
                        mol_type = other DNA
                        organism = synthetic construct
SEQUENCE: 40
aaggatgcga gtgataagtg gaatgccatg tgggctgtca aaa                    43

SEQ ID NO: 41           moltype = DNA  length = 19
FEATURE                 Location/Qualifiers
misc_feature            1..19
                        note = Description of Artificial Sequence: Synthetic
                         oligonucleotide
source                  1..19
                        mol_type = other DNA
                        organism = synthetic construct
SEQUENCE: 41
gccatgtggg ctgtcaaaa                                               19

SEQ ID NO: 42           moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 42
gaatgccatg tgggctgtca aaa                                          23

SEQ ID NO: 43           moltype = AA  length = 1604
FEATURE                 Location/Qualifiers
source                  1..1604
                        mol_type = protein
                        organism = Streptomyces sp.
SEQUENCE: 43
MPDQLNAPTP LGDRLTGAVR TVWAKHDRDT GKWLPLWRHM TDSAAVAGLL WDHWLPRNIK  60
DLIAEPLPGG VADARSLCVW LAGTHDIGKA TPAFACQVDE LAGVMTAAGL DMRTSKQLGE  120
DRRMAPHGLA GQVLLQEWLE ERRGWTHRAS AQFAVVAGGH HGVPPDHMQL HNLDAHPELL  180
RTQGLAEAQW RAVQDELLDA CALVFGVEER LDAWRTVKLP QTVQVLLTAT VIVSDWIASN  240
PDLFPYFPEE HPREEAERVA AAWQGLLLPA PWEPEEPSAP AAEFYASRFA LPPGAVVRPV  300
QEQALAMARD MERPGMLIIE APMGEGKTEA ALAVAEVFAA RSGAGGCYVA LPTMATSNAM  360
FPRLLRWLDR LPRADVSGGR DHEQRSVLLA HAKSALQEDY ATLMRESHRT IAAVDAYGDD  420
SRPRKGRPAA DGVRRKAPAE LVAHQWLRGR KKGLLASFAV GTIDQLLMAG LKSRHLALRH  480
LAMAGKVVVI DEVHAYDTYM NAYLDRVLAW LGEYRVPVVV LSATLPARRR GELAAAYTGE  540
DAQALTEATG YPLLTAVVPG REAVQFVAAA SGRGSDVLLE KLDDDDEALA DRLDTDLADG  600
GCALVVRNTV DRVMDTASVL RERFGADHVT VAHARFVDLD RARKDSELLA RFGPPDPDGG  660
SPQRPRNAHI VVASQVAEQS LDVDFDLLVS DLCPVDLLLQ RMGRLHRHPR GRDQERRPAR  720
LRQARCLVTG VGWDTSPAPE ADEGSRAIYG AYSLLRSLAV LAPHLGTAGA AGHPLRLPED  780
ISPLVRRAYG EEDPCPPEWE PVLAPARDKY RTARERQSQK AEVFRLDEVR KAGRPLIGWI  840
DAGVGDADDT PVGRAQVRDT KEGLEVLVVR RRADGSLCTL PWLDKGRGGL ELPVDAVPSA  900
LAARAVAASG LRLPYHFTSS PQTLDRTLAE LEELYVPAWQ EKESHWIAGE LILALDEEGR  960
AALAGQQLVY NPEEGLLVAS ADANTEATSG RVMDGKPSSA GDGKPGHAAD GNRARTTVGQ  1020
SPADRQTHQP PEGERHPVPP SAAPPPARPS FDLTSRPWLP VLLKDGSERE LSLPEVFDQA  1080
```

-continued

```
RDIRRLVGDL PTQDFALTRM LLALLYDALS EPGGDMAPAD TDAWEELWLS QSAYAAPVAA  1140
YLHRYRERFD LLHPESPFFQ TPGLRTAKNE VFSLNRLVAD VPNGDPFFSM RRPGVDRLGF  1200
AEAARWLVHA QAYDTSGIKT GAVGDPRVKA GKGYPQGPAW AGNLGGVLLE GDNLHETLLL  1260
NLIAGDTPGV HAAEVDRPAW RAEPSGPAPA PDLGLRPYGL RDLYTWQSRR IRLHHDADGV  1320
HGVVLAYGDS LEPHNRHGHE PMTSWRRSPT QEKKRQENLV YLPREHDPSR LAWRGMDGLL  1380
AGRETGSAQG PDGADRLAPK VVQWAAQLTT EGLLPRGYLI RTRVIGARYG TQQSVIDEVV  1440
DDGVLMPAVL LHEADRRYGD KAVDALHDAE KAVGALAQLA ADLALAVGTD PEPGRNTARD  1500
LGFGTLDTHY RRWLRELGGT SDPEEHRDRW KQEVRRLVAE LGERLLDGAG PAAWEGRLVE  1560
TGKGTRWLND AAAELRFRTR LREFLTTAPD TPTSPRPAPV ESPA                  1604

SEQ ID NO: 44          moltype = AA  length = 1559
FEATURE                Location/Qualifiers
source                 1..1559
                       mol_type = protein
                       organism = Streptomyces griseus
SEQUENCE: 44
MSNTPMSRDH PESLSAYARL SPVSRTAWGK HDRQTEQWLP LWRHMADSAA VAERLWDQWV  60
PDNVKALIAD AFPQGAQDAR RVAVFLACVH DIGKATPAFA CQVDGLADRM RAAGLSMPYL  120
KQFGLDRRMA PHGLAGQLLL QEWLAERFGW SERASGQFAV VAGGHHGTPP DHQHIHDLGL  180
RPHLLRTAGE SQDTWRSVQD ELMDACAVRA GVGGRFGAWR SVRLPQPVQV VLTAIVIVSD  240
WIASSSELFP YDPASWSPVG PEGEGRRLTA AWGGLDLPGP WRADQPDCTA AELFGKRFDL  300
PEGAGVRPVQ EEAVRVAQEL PGPGLLIIEA PMGEGKTEAA FAAAEILAAR TGAGGCLVAL  360
PTRATGDAMF PRLLRWLERL PSDGPRSVVL AHAKAALNEV WAGMTKADRR KITAVDLDSQ  420
VEDVSSAGGA RRANPASLHA HQWLRGRKKA LLSSFAVGTV DQVLFAGLKS RHLALRHLAV  480
AGKVVIVDEV HAYDAYMSAY LDRVLEWLAA YRVPVVMLSA TLPAHRRREL AAAYAGEETP  540
ELADALALPD DAYPLITAVA PGGLVLTARP EPASGRRTEV VLERLGDGPA LLAARLDEEL  600
RDGGCALVVR NTVDRVLEAA EHLRAHFGAE AVTVAHSRFV AADRARNDTV LRERFGPGGD  660
RPAGPHIVVA SQVVEQSLDI DFDLLVTDLA PVDLVLQRMG RLHRHPRTRP PRLSRARCLI  720
TGVEDWHAER PVPVRGSLAV YQGPHTLLRA LAVLGPHLDG VPLVLPDHIS PLVQAAYDER  780
PVGPAHWAPV LDEARRQYLT RLAEKRERAD VFRLGPVRRP GRPLFGWLDG NAGDADDSRT  840
GRAQVRDSEE SLEVLVVQRR ADGRLTTVSW LDGGRGGLDL PEHAPPPPRA AEVVAACALT  900
LPRSLTHPGV IDRTIAELER FVVPAWQVKE CPWLAGELLL VLDEDCQTRL SGLEVHYSTD  960
QGLRVGSVGT RSTNRAKGLE AVSVASFDLV SRPWLPVQYE DGATGELSLR EVFARAGEVR  1020
RLVGDLPTQE LALLRLLLAI LYDAYDEAPG RSGGAPAQLE DWEALWDEPD SFAVVAGYLD  1080
RHRDRFDLLH PERPFFQVAG LHTQKHEVAS LNRIVADVPN GEAFFSMRRP GVHRLGLAEA  1140
ARWLVHTHAY DASGIKSGME GDARVKGGKV YPQGVGWVGG LGGVFAEGAS LRETLLLNLI  1200
PTDEDILTSE PKADLPVWRR ETPPGPGVVE GDPSAPRPAG PRDLYTWQSR RLLLHTEGSD  1260
AIGVVLGYGD PLSPANRQKT EPMTGWRRSP AQEKKLGRPL VYLPRQHDPG RAAWRGLASL  1320
LYPQGEDGDT TGRGTDRSRP AGIVRWLALL STEGVLPKGS LIRTRLVGAV YGTQQSVVDD  1380
VVDDSIALPV VLLHQDRRLH GAVAVDAVAD AERAVSALGH LAGNLARASG SEAGPATATA  1440
RDQGFGALDG PYRRWLVDLA EDTDLERARA AWRDTVRLVV LGIGRELLDA AGRAAAEGRV  1500
IELPGVGKRW IDSSRADLWF RTRINRVLPR PLPEAHAPTA DIHAGHAVRA DEALSEETV   1559

SEQ ID NO: 45          moltype = AA  length = 1540
FEATURE                Location/Qualifiers
source                 1..1540
                       mol_type = protein
                       organism = Catenulispora acidiphila
SEQUENCE: 45
MFNVGSTRCW GDGGLRNAAE DLSAATRSAW AKSDPDSGQS LSLIRHLADS AAIAEHLWDQ  60
WLPDHVKSLI AEGLPEGLVD GRTLAVWLAG THDIGKLTPA FACQCEPLAQ AMRECGLDMP  120
TRTQFGDDRR VAPHGLAGQV LLREWLMERH GWSGRSADAF TVIAGGHHGV PPSYSQLHDL  180
DAYPELLRTP GASEGIWKSS QHELLDACAV MTGASSRLAH WRGLRLSQQA QVLLTGLVIV  240
ADWIASNTDL FPYPALGTGE AAIDPGKRVE LAWRGLELPA PWAPKYLMPG MQGLLASRFG  300
LPADAQLRPV QQMAVQLASA NAAPGLLVIE APMGEGKTEA ALLAAEILAA RSGAGGVFLA  360
LPTQATSNAM FARVVNWLRQ VPREGVASVH LAHGKAALDD AFASFLRAAP RLTSIDADGY  420
AGEANVRRDR RAGSADMVAH QWLRGRKKGI LSPFVVGTID QLLFTGLKSR HLALRHLAVA  480
GKVVVIDEVH AYDAYMSVYL ERVLSWLGAY RVPVVLLSAT LPADRRQALV EAYGGITSEA  540
LRDAREAYPV LTAVTIGAPA QAVGTEPAEG RRVDVNVEAF DDDLGRLADR LEAELVDGGC  600
ALIIRNTVGR VLQTAQQLRE RFGAGQVTVA HSRFIDLDRA RKDADLLARF GHDGARPRRH  660
IVVASQVAEQ SLDIDFDLLV TDLAPIDLVL QRMGRVHRHH RGGPEQSERP PSLRTARCLV  720
TGVDWAGIPS APIAGSVAVY GLHPLLRSLA VLQPYLTGSA LTLPGDINPL VQCAYAQSFV  780
APTGWGEAMD AAQAEHMAHI VQQREGAMAF CLDEVRGPGR SLIGWIDGGV GDADDTRAGR  840
AQVRDSPETI EVLVVQRGSD GVLRTLPWLD RGRGGLELPT EAVPPPRAAR AAAASALRLP  900
GLFAKPWMFD RVLRELEREY HEAWQAKESS WLQGELLLVL DEECRTVLAG YELSYNPDDG  960
LEMVMPGEPH AAVVRDKEAS DDKTASFDLT SAPWLPVLYA DGMQGVLSLR DVFAQSNLIR  1020
RLVGDLPTQD FALLRLLLAV LYDAVDGPRD GQDWEDLWTS DDPFAAVPAY LDSHRERFDL  1080
LHPATPFYQV PGLQTAKGEV GPLNKIVADV PDGDPFLTMR MPGVEQLSFA EAARWLVHTQ  1140
AFDTSGIKSG VVGDPKAVNG KRYPQGVAWL GNLGGVFAEG DTLRQTLLLN LIPADTTNLQ  1200
VTSAQDVPAW RGTNGRAGSD HADAEPRVPA GLRDLYTWQS RRIRLEYDTR GVTGAVLTYG  1260
DELTAHNKHG VEPMTGWRRS KPQEKKLGLS TVYMPQQHDP TRAAWRGIES LLAGSAGSGS  1320
SQTGEPASHY RPKIVDWLGE LAHHGNLPSR GLIRVRTSGA VYGTQQSIID EVVSDELTMA  1380
VVLLHEDDPR FGKAAVTAVK DADSAVAALG DLASDLARAA GLDPEPERVT ARDRAFGALD  1440
GPYRRWLLDL GNSTDPAAMR AVWQGRVYDI IAVQGQMLLD SAGSAAAQGR MVKTTRGERW  1500
MDDSLADLYF KGRIAKALSS RLGKKPTDPG EPVGIQEDPA                        1540

SEQ ID NO: 46          moltype = AA  length = 1407
FEATURE                Location/Qualifiers
REGION                 1..1407
```

```
                       note = Description of Artificial Sequence: Synthetic
                        polypeptide
source                 1..1407
                       mol_type = protein
                       organism = synthetic construct
SEQUENCE: 46
MEPFKYICHY WGKSSKSLTK GNDIHLLIYH CLDVAAVADC WWDQSVVLQN TFCRNEMLSK  60
QRVKAWLLFF IALHDIGKFD IRFQYKSAES WLKLNPATPS LNGPSTQMCR KFNHGAAGLY  120
WFNQDSLSEQ SLGDFFSFFD AAPHPYESWF PWVEAVTGHH GFILHSQDQD KSRWEMPASL  180
ASYAAQDKQA REEWISVLEA LFLTPAGLSI NDIPPDCSSL LAGFCSLADW LGSWTTTNTF  240
LFNEDAPSDI NALRTYFQDR QQDASRVLEL SGLVSNKRCY EGVHALLDNG YQPRQLQVLV  300
DALPVAPGLT VIEAPTGSGK TETALAYAWK LIDQQIADSV IFALPTQATA NAMLTRMEAS  360
ASHLFSSPNL ILAHGNSRFN HLFQSIKSRA ITEQGQEEAW VQCCQWLSQS NKKVFLGQIG  420
VCTIDQVLIS VLPVKHRFIR GLGIGRSVLI VDEVHAYDTY MNGLLEAVLK AQADVGGSVI  480
LLSATLPMKQ KQKLLDTYGL HTDPVENNSA YPLINWRGVN GAQRFDLLAH PEQLPPRFSI  540
QPEPICLADM LPDLTMLERM IAAANAGAQV CLICNLVDVA QVCYQRLKEL NNTQVDIDLF  600
HARFTLNDRR EKENRVISNF GKNGKRNVGR ILVATQVVEQ SLDVDFDWLI TQHCPADLLF  660
QRLGRLHRHH RKYRPAGFEI PVATILLPDG EGYGRHEHIY SNVRVMWRTQ QHIEELNGAS  720
LFFPDAYRQW LDSIYDDAEM DEPEWVGNGM DKFESAECEK RFKARKVLQW AEEYSLQDND  780
ETILAVTRDG EMSLPLLPYV QTSSGKQLLD GQVYEDLSHE QQYEALALNR VNVPFTWKRS  840
FSEVVDEDGL LWLEGKQNLD GWVWQGNSIV ITYTGDEGMT RVIPANPKGD PTNRAKGLEA  900
VSVASMNLLI DNWIPVRPRN GGKVQIINLQ SLYCSRDQWR LSLPRDDMEL AALALLVCIG  960
QIIAPAKDDV EFRHRIMNPL TEDEFQQLIA PWIDMFYLNH AEHPFMQTKG VKANDVTPME  1020
KLLAGVSGAT NCAFVNQPGQ GEALCGGCTA IALFNQANQA PGFGGGFKSG LRGGTPVTTF  1080
VRGIDLRSTV LLNVLTLPRL QKQFPNESHT ENQPTWIKPI KSNESIPASS IGFVRGLFWQ  1140
PAHIELCDPI GIGKCSCCGQ ESNLRYTGFL KEKFTFTVNG LWPHPHSPCL VTVKKGEVEE  1200
KFLAFTTSAP SWTQISRVVV DKIIQNENGN RVAAVVNQFR NIAPQSPLEL IMGGYRNNQA  1260
SILERRHDVL MFNQGWQQYG NVINEIVTVG LGYKTALRKA LYTFAEGFKN KDFKGAGVSV  1320
HETAERHFYR QSELLIPDVL ANVNFSQADE VIADLRDKLH QLCEMLFNQS VAPYAHHPKL  1380
ISTLALARAT LYKHLRELKP QGGPSNG                                    1407

SEQ ID NO: 47          moltype = DNA  length = 49
FEATURE                Location/Qualifiers
misc_feature           1..49
                       note = Description of Artificial Sequence: Synthetic
                        oligonucleotide
source                 1..49
                       mol_type = other DNA
                       organism = synthetic construct
SEQUENCE: 47
ccgtcttgcg ctagctctag aactagtcct cagcctaggc ctaagctgt            49

SEQ ID NO: 48          moltype = AA  length = 6
FEATURE                Location/Qualifiers
REGION                 1..6
                       note = Description of Artificial Sequence: Synthetic 6xHis
                        tag
source                 1..6
                       mol_type = protein
                       organism = synthetic construct
SEQUENCE: 48
HHHHHH                                                           6

SEQ ID NO: 49          moltype = AA  length = 15
FEATURE                Location/Qualifiers
REGION                 1..15
                       note = Simian virus 40
source                 1..15
                       mol_type = protein
                       organism = unidentified
SEQUENCE: 49
PKKKRKVDPK KKRKV                                                 15

SEQ ID NO: 50          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 50
MHHHHHH                                                          7
```

The invention claimed is:

1. A Type I CRISPR composition comprising:

a first Type I CASCADE protein complex comprising a first Cse1 subunit protein, having an N-terminus and a C-terminus; a first *Escherichia coli* (*E. coli*) Cas3 mutant protein fused to the N-terminus of the first Cse1 subunit protein by a first linker polypeptide; and a first CRISPR-derived RNA (crRNA) molecule comprising a spacer sequence complementary to a first target nucleic acid, and a second Type I CASCADE protein complex comprising a second Cse1 subunit protein, having an N-terminus and a C-terminus; a second *E. coli* Cas3 mutant protein fused to the N-terminus of the second Cse1 subunit protein by a second linker polypeptide; and a second CRISPR-derived RNA (crRNA) molecule comprising a spacer sequence complementary to a second target nucleic acid;

wherein the first *E. coli* Cas3 mutant protein and the second *E. coli* Cas3 mutant protein independently has a mutation selected from K320N, D452N, and S483A/T485A; and wherein the first Type I CASCADE protein complex and the second Type I CASCADE protein complex further comprises at least a Cas7 subunit protein, a Cas5 subunit protein, and a Cas6 subunit protein.

2. The composition of claim 1, wherein the first Type I CASCADE protein complex and the second Type I CASCADE protein complex form a heterodimer.

3. The Type I CRISPR composition of claim 1, wherein the first and the second linker polypeptides comprise a *Streptomyces griseus* linker polypeptide.

4. The Type I CRISPR composition of claim 1, wherein the first and the second Type I CASCADE protein complexes further comprise a Type I CRISPR associated Cse2 subunit protein.

5. The Type I CRISPR composition of claim 1, wherein each of the first and the second CRISPR-derived RNA (crRNA) molecules has a length between 35 and 75 nucleotides.

6. The Type I CRISPR composition of claim 5, wherein each of the first and the second CRISPR-derived RNA (crRNA) molecules has a length of 61 nucleotides.

7. The Type I CRISPR composition of claim 1, wherein each of the first and the second Type I CASCADE protein complexes further comprises a nuclear localization signal.

8. An in vitro or ex vivo cell comprising the Type I CRISPR composition of claim 1.

9. The cell of claim 8, wherein the cell is a prokaryotic cell.

10. The cell of claim 8, wherein the cell is selected from the group consisting of a plant cell, a fungal cell, an animal cell, a yeast cell, an insect cell, a mammalian cell, and a human cell.

11. The cell of claim 8, wherein the cell is an isolated cell.

12. The cell of claim 8, wherein the cell is a human stem cell.

13. The Type I CRISPR composition of claim 1, wherein the first and the second *E. coli* Cas3 mutant proteins are Cas3 D452N.

14. The Type I CRISPR composition of claim 1, wherein the first and the second Type I CASCADE protein complexes comprise the following stoichiometries:

$Cse1_1Cse2_2Cas7_6Cas5_1Cas6_1$ or $Cse1_1Cse2_2Cas7_6Cas5_1Cas6e_1$.

15. A method of cleaving a double-stranded target DNA sequence, the method comprising contacting the double-stranded target DNA sequence with the Type I CRISPR composition of claim 1, wherein the first strand of the double-stranded target DNA sequence comprises a first target nucleic acid and a first cleavage site, and the second strand of the double-stranded target DNA sequence comprises a second target nucleic acid and a second cleavage site, and wherein the first Type I CASCADE protein complex binds the first target nucleic acid and cleaves the first cleavage site, and the second Type I CASCADE protein complex binds the second target nucleic acid and cleaves the second cleavage site.

16. The method of claim 15, wherein the double-stranded target DNA sequence is in genomic DNA.

* * * * *